US012653687B2

(12) United States Patent
Sayger et al.

(10) Patent No.: US 12,653,687 B2
(45) Date of Patent: Jun. 16, 2026

(54) BONE REPOSITIONING GUIDE SYSTEM AND PROCEDURE

(71) Applicant: Crossroads Extremity Systems, LLC, Memphis, TN (US)

(72) Inventors: Daniel Sayger, Hernando, MS (US); Michael Chad Hollis, Collierville, TN (US); Vernon Hartdegen, Collierville, TN (US)

(73) Assignee: Crossroads Extremity Systems, LLC, Memphis, TN (US)

( * ) Notice: Subject to any disclaimer, the term of this patent is extended or adjusted under 35 U.S.C. 154(b) by 626 days.

(21) Appl. No.: 18/049,761

(22) Filed: Oct. 26, 2022

(65) Prior Publication Data

US 2023/0149045 A1 May 18, 2023

Related U.S. Application Data

(60) Continuation-in-part of application No. 17/938,289, filed on Oct. 5, 2022, which is a continuation-in-part (Continued)

(51) Int. Cl.
*A61F 2/42* (2006.01)
*A61B 17/064* (2006.01)
(Continued)

(52) U.S. Cl.
CPC .......... *A61F 2/4225* (2013.01); *A61B 17/151* (2013.01); *A61B 17/1697* (2013.01);
(Continued)

(58) Field of Classification Search
CPC ........ A61B 2017/564; A61B 2017/565; A61B 2017/568; A61B 2017/681; A61B 17/17;
(Continued)

(56) References Cited

U.S. PATENT DOCUMENTS

| | | | |
|---|---|---|---|
| 4,069,824 | A | 1/1978 | Weinstock |
| 4,335,715 | A | 6/1982 | Kirkley |

(Continued)

FOREIGN PATENT DOCUMENTS

| | | | |
|---|---|---|---|
| EP | 0570187 | A1 | 11/1993 |
| FR | 3117762 | A1 | 6/2022 |
| JP | 2006-346447 | A | 12/2006 |
| JP | 2017-047167 | A | 3/2017 |
| JP | 2019-024741 | A | 2/2019 |
| JP | 2019-080918 | A | 5/2019 |
| WO | 00/06036 | A1 | 2/2000 |
| WO | 2004/075775 | A2 | 9/2004 |

(Continued)

OTHER PUBLICATIONS

Arthrex Hallux Valgus Solutions, Arthrex, Inc., www.arthrex.com 2009, 2 pp.

(Continued)

*Primary Examiner* — Marcela I. Shirsat

(57) ABSTRACT

A surgical system and procedure are provided for correcting a deformity between first and second bones using an alignment guide based on a correction factor. The alignment guide is used to insert one or more k-wires into each of the first and second bones in a deformed configuration. A correction guide is passed along the k-wires to rotate and/or translate the first bone relative to the second bone into the corrected configuration. An auxiliary correction guide can be passed along the k-wires to further rotate and/or translate the first bone relative to the second bone from the corrected configuration to an adjusted configuration.

16 Claims, 47 Drawing Sheets

Related U.S. Application Data of application No. 17/305,644, filed on Jul. 12, 2021, now Pat. No. 12,514,713, which is a division of application No. 16/938,375, filed on Jul. 24, 2020, now Pat. No. 11,058,546.

(60) Provisional application No. 63/263,076, filed on Oct. 26, 2021, provisional application No. 62/879,340, filed on Jul. 26, 2019.

(51) Int. Cl.

| | |
|---|---|
| *A61B 17/15* | (2006.01) |
| *A61B 17/16* | (2006.01) |
| *A61B 17/17* | (2006.01) |
| *A61B 17/56* | (2006.01) |
| *A61B 17/68* | (2006.01) |
| *A61B 17/80* | (2006.01) |
| *A61B 17/84* | (2006.01) |
| *A61F 2/46* | (2006.01) |
| *A61F 5/01* | (2006.01) |

(52) U.S. Cl.
CPC .......... *A61B 17/1775* (2016.11); *A61B 17/56* (2013.01); *A61B 17/8061* (2013.01); *A61B 17/808* (2013.01); *A61B 17/848* (2013.01); *A61B 17/0642* (2013.01); *A61B 17/1728* (2013.01); *A61B 17/1739* (2013.01); *A61B 2017/564* (2013.01); *A61B 2017/565* (2013.01); *A61B 2017/681* (2013.01); *A61B 17/8004* (2013.01); *A61F 2002/4228* (2013.01); *A61F 2002/4233* (2013.01); *A61F 2002/4238* (2013.01); *A61F 2/4606* (2013.01); *A61F 5/019* (2013.01)

(58) Field of Classification Search
CPC ............ A61B 17/1775; A61B 17/1728; A61B 17/1739; A61B 17/15; A61B 17/151; A61B 17/152; A61B 17/1697; A61B 17/56; A61B 17/80; A61B 17/8061; A61B 17/808; A61B 17/848; A61B 17/68; A61B 17/0642; A61B 17/8004; A61B 17/1659; A61B 17/1682; A61F 2002/4228; A61F 2002/4233; A61F 2002/4238; A61F 5/019; A61F 2/4225; A61F 2/4606; A61F 2/4603
USPC ......... 606/281, 280, 86 R, 87, 98, 103, 104, 606/86 A, 86 B, 914, 915
See application file for complete search history.

(56) References Cited

U.S. PATENT DOCUMENTS

| | | |
|---|---|---|
| 4,349,018 A | 9/1982 | Chambers |
| 4,409,973 A | 10/1983 | Neufeld |
| 4,440,168 A | 4/1984 | Warren |
| 4,501,268 A | 2/1985 | Comparetto |
| 4,502,474 A | 3/1985 | Comparetto |
| 4,509,511 A | 4/1985 | Neufeld |
| 4,565,191 A | 1/1986 | Slocum |
| 4,627,425 A | 12/1986 | Reese |
| 4,632,102 A | 12/1986 | Comparetto |
| 4,664,102 A | 5/1987 | Comparetto |
| 4,708,133 A | 11/1987 | Comparetto |
| 4,736,737 A | 4/1988 | Fargie et al. |
| 4,750,481 A | 6/1988 | Reese |
| 4,757,810 A | 7/1988 | Reese |
| 4,852,558 A | 8/1989 | Outerbridge |
| 4,913,144 A | 4/1990 | Del Medico |
| 4,952,214 A | 8/1990 | Comparetto |
| 4,959,066 A | 9/1990 | Dunn et al. |

| | | |
|---|---|---|
| 5,035,698 A | 7/1991 | Comparetto |
| 5,042,983 A | 8/1991 | Rayhack |
| 5,049,149 A | 9/1991 | Schmidt |
| 5,053,039 A | 10/1991 | Hofmann et al. |
| 5,078,719 A | 1/1992 | Schreiber |
| 5,112,334 A | 5/1992 | Alchermes et al. |
| 5,147,364 A | 9/1992 | Comparetto |
| 5,176,685 A | 1/1993 | Rayhack |
| 5,246,444 A | 9/1993 | Schreiber |
| D357,534 S | 4/1995 | Hayes |
| 5,413,579 A | 5/1995 | Tom Du Toit |
| 5,449,360 A | 9/1995 | Schreiber |
| 5,470,335 A | 11/1995 | Du Toit |
| 5,540,695 A | 7/1996 | Levy |
| 5,578,038 A | 11/1996 | Slocum |
| 5,601,565 A | 2/1997 | Huebner |
| 5,613,969 A | 3/1997 | Jenkins, Jr. |
| 5,620,448 A | 4/1997 | Puddu |
| 5,643,270 A | 7/1997 | Combs |
| 5,667,510 A | 9/1997 | Combs |
| H1706 H | 1/1998 | Mason |
| 5,722,978 A | 3/1998 | Jenkins, Jr. |
| 5,749,875 A | 5/1998 | Puddu |
| 5,779,709 A | 7/1998 | Harris et al. |
| 5,843,085 A | 12/1998 | Graser |
| 5,911,724 A | 6/1999 | Wehrli |
| 5,980,526 A | 11/1999 | Johnson et al. |
| 5,984,931 A | 11/1999 | Greenfield |
| 6,007,535 A | 12/1999 | Rayhack et al. |
| 6,027,504 A | 2/2000 | McGuire |
| 6,030,391 A | 2/2000 | Brainard et al. |
| 6,203,545 B1 | 3/2001 | Stoffella |
| 6,248,109 B1 | 6/2001 | Stoffella |
| 6,391,031 B1 | 5/2002 | Toomey |
| 6,547,793 B1 | 4/2003 | McGuire |
| 6,676,662 B1 | 1/2004 | Bagga et al. |
| 6,755,838 B2 | 6/2004 | Trnka |
| 6,796,986 B2 | 9/2004 | Duffner |
| 7,018,383 B2 | 3/2006 | McGuire |
| 7,112,204 B2 | 9/2006 | Justin et al. |
| 7,182,766 B1 | 2/2007 | Mogul |
| 7,540,874 B2 | 6/2009 | Trumble et al. |
| 7,572,258 B2 | 8/2009 | Stiernborg |
| 7,691,108 B2 | 4/2010 | Lavallee |
| 7,763,026 B2 | 7/2010 | Egger et al. |
| D630,746 S | 1/2011 | Richter et al. |
| 7,967,823 B2 | 6/2011 | Ammann et al. |
| 7,972,338 B2 | 7/2011 | Todd |
| 8,062,301 B2 | 11/2011 | Ammann et al. |
| 8,083,746 B2 | 12/2011 | Novak |
| 8,137,406 B2 | 3/2012 | Novak et al. |
| 8,236,000 B2 | 8/2012 | Ammann et al. |
| 8,262,664 B2 | 9/2012 | Justin et al. |
| 8,277,459 B2 | 10/2012 | Sand et al. |
| 8,282,645 B2 | 10/2012 | Lawrence et al. |
| 8,313,492 B2 | 11/2012 | Wong et al. |
| 8,409,209 B2 | 4/2013 | Ammann et al. |
| 8,496,662 B2 | 7/2013 | Novak et al. |
| 8,529,571 B2 | 9/2013 | Horan et al. |
| 8,540,777 B2 | 9/2013 | Ammann et al. |
| 8,545,508 B2 | 10/2013 | Collazo |
| D695,402 S | 12/2013 | Dacosta et al. |
| 8,652,142 B2 | 2/2014 | Geissler |
| 8,657,820 B2 | 2/2014 | Kubiak et al. |
| 8,702,715 B2 | 4/2014 | Ammann et al. |
| 8,771,279 B2 | 7/2014 | Philippon et al. |
| 8,777,948 B2 | 7/2014 | Bernsteiner |
| 8,888,785 B2 | 11/2014 | Ammann et al. |
| 8,900,247 B2 | 12/2014 | Tseng et al. |
| 8,906,026 B2 | 12/2014 | Ammann et al. |
| 9,060,822 B2 | 6/2015 | Lewis et al. |
| 9,113,920 B2 | 8/2015 | Ammann et al. |
| 9,622,805 B2 | 4/2017 | Santrock et al. |
| 9,687,250 B2 | 6/2017 | Dayton et al. |
| 9,814,474 B2 | 11/2017 | Montoya et al. |
| 9,907,558 B2 | 3/2018 | Fallin et al. |
| 9,936,994 B2 | 4/2018 | Smith et al. |
| 10,045,807 B2 | 8/2018 | Santrock et al. |
| 10,245,086 B2 | 4/2019 | Treace et al. |

(56) References Cited

U.S. PATENT DOCUMENTS

| | | | |
|---|---|---|---|
| 10,245,088 B2 | 4/2019 | Dayton et al. | |
| 10,292,713 B2 | 5/2019 | Fallin et al. | |
| 10,299,842 B2 | 5/2019 | Hollis et al. | |
| 10,335,220 B2 | 7/2019 | Smith et al. | |
| 10,342,590 B2 | 7/2019 | Bays et al. | |
| 10,376,268 B2 | 8/2019 | Fallin et al. | |
| 10,470,779 B2 | 11/2019 | Fallin et al. | |
| 10,512,470 B1 | 12/2019 | Bays et al. | |
| 10,555,757 B2 | 2/2020 | Dayton | |
| 10,561,426 B1 | 2/2020 | Dayton et al. | |
| 10,575,862 B2 | 3/2020 | Bays et al. | |
| 10,743,995 B2 | 8/2020 | Fallin et al. | |
| 10,898,211 B2 | 1/2021 | Fallin et al. | |
| 11,058,546 B2 | 7/2021 | Hollis et al. | |
| 11,116,558 B2 | 9/2021 | Smith et al. | |
| 11,147,590 B2 | 10/2021 | Dayton et al. | |
| 11,160,567 B2 | 11/2021 | Fallin et al. | |
| 11,304,735 B2 | 4/2022 | Sayger et al. | |
| 12,133,655 B2 | 11/2024 | Gazonnet et al. | |
| 2002/0165552 A1 | 11/2002 | Duffner | |
| 2004/0097946 A1 | 5/2004 | Dietzel et al. | |
| 2004/0138669 A1 | 7/2004 | Horn | |
| 2005/0070909 A1 | 3/2005 | Egger et al. | |
| 2005/0149042 A1 | 7/2005 | Metzger | |
| 2005/0228389 A1 | 10/2005 | Stiernborg | |
| 2005/0251147 A1 | 11/2005 | Novak | |
| 2005/0273112 A1 | 12/2005 | McNamara | |
| 2006/0129163 A1 | 6/2006 | McGuire | |
| 2006/0241637 A1 | 10/2006 | Hodorek et al. | |
| 2006/0264961 A1 | 11/2006 | Murray-Brown | |
| 2006/0276795 A1 | 12/2006 | Orbay et al. | |
| 2007/0010818 A1 | 1/2007 | Stone et al. | |
| 2007/0265634 A1 | 11/2007 | Weinstein | |
| 2007/0276383 A1 | 11/2007 | Rayhack | |
| 2008/0015603 A1 | 1/2008 | Collazo | |
| 2008/0039850 A1 | 2/2008 | Rowley et al. | |
| 2008/0147073 A1 | 6/2008 | Ammann et al. | |
| 2008/0172056 A1* | 7/2008 | Edwards | A61B 90/92 606/104 |
| 2008/0195215 A1 | 8/2008 | Morton | |
| 2008/0269908 A1 | 10/2008 | Warburton | |
| 2009/0036931 A1 | 2/2009 | Pech et al. | |
| 2009/0054899 A1 | 2/2009 | Ammann et al. | |
| 2009/0210010 A1 | 8/2009 | Strnad et al. | |
| 2009/0222047 A1 | 9/2009 | Graham | |
| 2010/0125300 A1 | 5/2010 | Blitz et al. | |
| 2010/0130981 A1 | 5/2010 | Richards | |
| 2010/0152782 A1 | 6/2010 | Stone et al. | |
| 2011/0178524 A1 | 7/2011 | Lawrence et al. | |
| 2011/0188550 A1 | 8/2011 | Wajcer et al. | |
| 2011/0213376 A1 | 9/2011 | Maxson et al. | |
| 2011/0224734 A1 | 9/2011 | Schelling | |
| 2011/0245835 A1* | 10/2011 | Dodds | A61B 17/155 606/87 |
| 2012/0016426 A1 | 1/2012 | Robinson | |
| 2012/0095465 A1 | 4/2012 | Graham | |
| 2012/0185056 A1 | 7/2012 | Warburton | |
| 2012/0191199 A1 | 7/2012 | Raemisch | |
| 2012/0303033 A1 | 11/2012 | Weiner et al. | |
| 2013/0012949 A1 | 1/2013 | Fallin et al. | |
| 2013/0090662 A1 | 4/2013 | Hanson et al. | |
| 2013/0172942 A1 | 7/2013 | Lewis et al. | |
| 2013/0184708 A1 | 7/2013 | Robinson et al. | |
| 2013/0226248 A1 | 8/2013 | Hatch et al. | |
| 2013/0226252 A1 | 8/2013 | Mayer | |
| 2013/0231668 A1 | 9/2013 | Olsen et al. | |
| 2013/0317559 A1 | 11/2013 | Leavitt et al. | |
| 2013/0331845 A1 | 12/2013 | Horan et al. | |
| 2014/0188139 A1 | 7/2014 | Fallin et al. | |
| 2014/0194999 A1 | 7/2014 | Orbay et al. | |
| 2014/0343555 A1 | 11/2014 | Russi et al. | |
| 2015/0057667 A1 | 2/2015 | Ammann et al. | |
| 2015/0245858 A1 | 9/2015 | Weiner et al. | |
| 2016/0015426 A1 | 1/2016 | Dayton | |
| 2016/0135858 A1 | 5/2016 | Dacosta et al. | |
| 2016/0192950 A1 | 7/2016 | Dayton et al. | |
| 2016/0192970 A1 | 7/2016 | Dayton et al. | |
| 2016/0213384 A1 | 7/2016 | Fallin et al. | |
| 2016/0235414 A1 | 8/2016 | Hatch et al. | |
| 2016/0235454 A1 | 8/2016 | Treace et al. | |
| 2016/0324532 A1 | 11/2016 | Montoya et al. | |
| 2016/0324555 A1 | 11/2016 | Brumfield et al. | |
| 2016/0354127 A1 | 12/2016 | Lundquist et al. | |
| 2017/0007305 A1 | 1/2017 | Hollis et al. | |
| 2017/0014143 A1 | 1/2017 | Dayton et al. | |
| 2017/0014173 A1* | 1/2017 | Smith | A61B 17/1739 |
| 2017/0042598 A1 | 2/2017 | Santrock et al. | |
| 2017/0042599 A1 | 2/2017 | Bays et al. | |
| 2017/0049576 A1 | 2/2017 | Guilford et al. | |
| 2017/0056031 A1 | 3/2017 | Awtrey et al. | |
| 2017/0079669 A1 | 3/2017 | Bays et al. | |
| 2017/0156717 A1 | 6/2017 | Triplett et al. | |
| 2017/0164989 A1 | 6/2017 | Weiner et al. | |
| 2017/0172638 A1 | 6/2017 | Santrock et al. | |
| 2017/0196602 A1 | 7/2017 | Lundquist et al. | |
| 2018/0110530 A1 | 4/2018 | Wagner et al. | |
| 2018/0125504 A1 | 5/2018 | Dayton et al. | |
| 2018/0168746 A1 | 6/2018 | Swayze et al. | |
| 2018/0296257 A1 | 10/2018 | Penzimer et al. | |
| 2018/0317906 A1 | 11/2018 | Hollis et al. | |
| 2018/0317992 A1 | 11/2018 | Santrock et al. | |
| 2018/0353172 A1 | 12/2018 | Hartdegen et al. | |
| 2019/0125418 A1 | 5/2019 | Muller et al. | |
| 2019/0175238 A1 | 6/2019 | Dayton et al. | |
| 2019/0274745 A1 | 9/2019 | Smith et al. | |
| 2019/0328435 A1 | 10/2019 | Bays et al. | |
| 2019/0328436 A1 | 10/2019 | Bays et al. | |
| 2019/0336140 A1 | 11/2019 | Dacosta et al. | |
| 2019/0357919 A1 | 11/2019 | Fallin et al. | |
| 2020/0000464 A1 | 1/2020 | Gaston et al. | |
| 2020/0015856 A1 | 1/2020 | Treace et al. | |
| 2020/0078025 A1 | 3/2020 | Fallin et al. | |
| 2020/0138491 A1 | 5/2020 | Brigido et al. | |
| 2020/0197021 A1 | 6/2020 | Dayton et al. | |
| 2020/0375644 A1 | 12/2020 | Smith et al. | |
| 2021/0022879 A1 | 1/2021 | Hollis et al. | |
| 2021/0026357 A1 | 1/2021 | Okubi et al. | |
| 2021/0077162 A1 | 3/2021 | Muller et al. | |
| 2021/0077192 A1 | 3/2021 | Perler et al. | |
| 2021/0251670 A1 | 8/2021 | Sayger et al. | |
| 2021/0282823 A1 | 9/2021 | Day et al. | |
| 2021/0307763 A1 | 10/2021 | Fallin et al. | |
| 2021/0338450 A1 | 11/2021 | Hollis et al. | |
| 2022/0323085 A1* | 10/2022 | Hales | A61B 17/15 |
| 2023/0043795 A1 | 2/2023 | Hollis et al. | |

FOREIGN PATENT DOCUMENTS

| | | | | |
|---|---|---|---|---|
| WO | 2004/089227 A2 | 10/2004 | | |
| WO | 2005/041785 A1 | 5/2005 | | |
| WO | 2007/008348 A2 | 1/2007 | | |
| WO | 2008/097781 A1 | 8/2008 | | |
| WO | 2016/134154 A1 | 8/2016 | | |
| WO | 2016/134160 A1 | 8/2016 | | |
| WO | 2017/011589 A1 | 1/2017 | | |
| WO | 2017/031000 A1 | 2/2017 | | |
| WO | 2017/049056 A1 | 3/2017 | | |
| WO | 2018/081185 A1 | 5/2018 | | |
| WO | WO-2019113394 A1 * | 6/2019 | | A61B 17/15 |
| WO | 2021/021640 A1 | 2/2021 | | |
| WO | 2021/026357 A1 | 2/2021 | | |
| WO | 2021/167992 A1 | 8/2021 | | |

OTHER PUBLICATIONS

Comprehensive Solutions for Forefoot and Midfood Sungery using the Mini TightRope System, Arthrex, Inc., www arthrex com 2012, 15 pp.

Didomenico, Lawrence A., et al. "Lapidus Bunionectomy: First Metatarsal-Cuneiform Arthrodesis," Souhterland, Chapter 31, Aug. 18, 2012.

Distal Extremities Orthopaedic Update, Arthrex, Inc., www.arthrex. com, 2014, 24 pp.

(56)                References Cited

OTHER PUBLICATIONS

Dobbe, et al., "Computer-Assisted and Patent-Specific 3-D Planning and Evaluation of a Single-Cut Rotational Osteotomy for Complex long-Bone Deformities". Med Biol Eng Comput (2011) 49:1363-1370.

Foot & Ankle Repair and Reconstruction Technology Brochure, Arthrex, Inc., www.athrex.com, 2016, 86 pp.

Gregg, Julie, et al., "Plantar Plate Repair and Weil Osteotomy for Meteatarsophalangeal Joint Instability", Foot and Ankle Surgery 13(2007) 116-121.

International Search Report and Written Opinion dated Jul. 22, 2021 in application No. PCT/US21/18398.

International Search Report and Written Opinion for PCT Application No. PCT/US2020/043525 dated Dec. 7, 2020 in 22 pages.

Meyer, D.C., et al., "A New Methodology for the Planning of Single Cut Corrective Osteotornles of Mai-Aligned Long Bones", Clinical Blornechanics 20(2005) 223-227.

Oscillating Saw Attachment fo, EPD/APD, Colibri II and Small Electric Drive, Synthes GmbH, www.synthes.com, 2012, 2 pp.

Scarf Osteotomy Technical Information Sheet, TALUS group of GECO, www.geco-medical.org, 2004, 2 pp.

Shurnas, Paul S., M.D., et al., Proximal Metatarsal Opening Wedge Osteotomy: PMOW-Arthrex LPS System, Arthrex, Inc., www.arthrex.com, 2008, 1 pp.

Speed Triad Medial Technique, BioMedical Enterprises, www.bme-tx.com, 2015, 2 pp.

The Accu-Cut Osteotomy Guide System, BioPro Implants, www.bioproimpiants.com, Brochure No. 16932 Rev07, 2 pp.

The Accu-Cut Osteotomy Guide System, BioProimplants. www.bioproimplants.com, Brochure No. 17136, Rev4, 2 pp.

The Next Generation in Foot & Ankle Repair and Reconstruction Technology 2016, Arthrex, Inc., www.arthrex.com, 2016, 76 pp.

Weil, Lowell Jr., el al., "Anatomic Plantar Plate Repair Using the Weil Metatarsal Osteotomy Approach", Foot & Ankle Specialist, http://fas.sagepub.com/, 2011, 7 pp.

International Search Report and Written Opinion dated Dec. 20, 2023, PCT Application PCT/IB2023/059538, 15 pages.

Supplementary European Search Report and Search Opinion dated Apr. 8, 2024, Application No. EP 21757520.8, 14 pages.

Supplementary European Search Report dated Jul. 5, 2023, Application No. EP20846870.2, 8 pages.

* cited by examiner

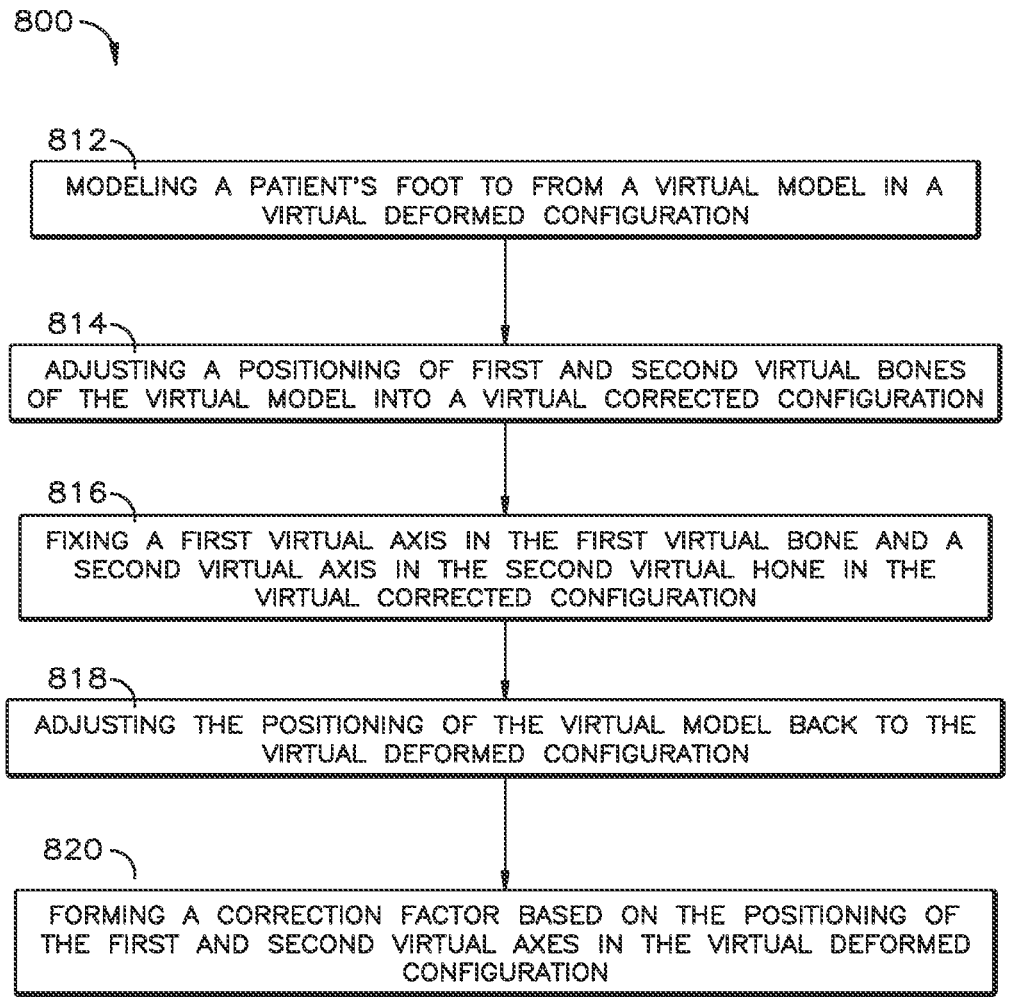

800

812
MODELING A PATIENT'S FOOT TO FROM A VIRTUAL MODEL IN A VIRTUAL DEFORMED CONFIGURATION

814
ADJUSTING A POSITIONING OF FIRST AND SECOND VIRTUAL BONES OF THE VIRTUAL MODEL INTO A VIRTUAL CORRECTED CONFIGURATION

816
FIXING A FIRST VIRTUAL AXIS IN THE FIRST VIRTUAL BONE AND A SECOND VIRTUAL AXIS IN THE SECOND VIRTUAL HONE IN THE VIRTUAL CORRECTED CONFIGURATION

818
ADJUSTING THE POSITIONING OF THE VIRTUAL MODEL BACK TO THE VIRTUAL DEFORMED CONFIGURATION

820
FORMING A CORRECTION FACTOR BASED ON THE POSITIONING OF THE FIRST AND SECOND VIRTUAL AXES IN THE VIRTUAL DEFORMED CONFIGURATION

Fig.27

BONE REPOSITIONING GUIDE SYSTEM AND PROCEDURE

CROSS REFERENCE TO RELATED APPLICATIONS

This claims priority to U.S. Patent Application Ser. No. 63/263,076 filed Oct. 26, 2021, and is a continuation-in-part of U.S. patent application Ser. No. 17/938,289 filed Oct. 5, 2022, which is a continuation-in-part of U.S. patent application Ser. No. 17/305,644 filed Jul. 12, 2021, which is a divisional of U.S. patent application Ser. No. 16/938,375 filed Jul. 24, 2020 (issued as U.S. Pat. No. 11,058,546), which claims priority to U.S. Patent Application Ser. No. 62/879,340 filed Jul. 26, 2019, the disclosure of each of which is hereby incorporated by reference as if set forth in its entirety herein.

FIELD

The present invention generally relates to surgical systems and procedures for correcting alignment between two bones or bone segments spanning a joint or an osteotomy, and particularly relates to surgical systems and procedures for correcting a bunion in a patient's foot.

BACKGROUND

Bone misalignment and/or deformation can be a source of discomfort and reduced mobility in patients, particularly in a patient's feet. One particularly common foot disorder is a bunion. Bunions are a progressive disorder, typically beginning with a leaning of the great toe. The leaning of the great toe may gradually change an angle of the bones and produce a characteristic bump on the medial side of the metatarsal near the joint of the metatarsal with the proximal phalanx. Specifically, the bunion is the prominence made of bone and at times an inflamed bursa. Hallux valgus is the condition in which the great toe deviates from the normal position toward the direction of the second toe. Accordingly, the present invention is directed to surgical systems and procedures for correction of bunions, Hallux valgus, and for bone realignments more generally.

SUMMARY

The foregoing summary is illustrative only and is not intended to be limiting. Other aspects, features, and advantages of the systems, devices, and methods and/or other subject matter described in this application will become apparent in the teachings set forth below. The summary is provided to introduce a selection of some of the concepts of this disclosure. The summary is not intended to identify key or essential features of any subject matter described herein.

According to one aspect of the disclosure, a method for correcting alignment between a first bone and a second bone by fusing a joint between the first bone and the second bone includes providing a first guide. The first guide includes a first end portion with a first cannula aligned along a first axis. A second end portion has a second cannula aligned along a second axis. The first axis is non-parallel with the second axis. The first axis is configured to intersect the first bone and the second axis is configured to intersect the second bone when the first and second bones are in a deformed configuration. A first k-wire is inserted through the first cannula and into the first bone. A second k-wire is inserted through the second cannula and into the second bone. The first guide is removed from the first and second k-wires. A second guide includes a first end portion with a first cannula. A second end portion has a second cannula. The first cannula is parallel with the second cannula. The second guide slides over the first and second k-wires. The first k-wire is received within the first cannula of the second guide and the second k-wire is received within the second cannula of the second guide. The second guide acts on the first and second k-wires to re-align the first and second bones into a corrected configuration.

In another aspect, the method includes fixing the first and second bones in the corrected configuration and removing the second guide and the first and second k-wires from the first and second bones.

In another aspect, the method includes fixing the first and second bones in the corrected configuration includes inserting a first stabilizing wire into the first and second bones.

In another aspect, the method includes attaching a first end of a bone plate with the first bone and a second end of the bone plate with the second bone such that the first and second bones are retained in the corrected configuration.

In another aspect, the method includes inserting a bone plate clip into the first and second bones.

In another aspect, the method includes resecting a first end of the first bone.

In another aspect, the first end portion of the first guide includes a third cannula aligned parallel with the first axis.

In another aspect, the method includes inserting a third k-wire into the first bone through the third cannula and resecting the first end of the first bone includes inserting a first resecting guide over the first and third k-wires to align the first resecting guide with the first end of the first bone.

In another aspect, the method includes resecting a first end of the second bone.

In another aspect, the second end of the first guide includes a fourth cannula aligned parallel with the second axis.

In another aspect, the method includes resecting the first end of the second bone.

In another aspect, the method includes inserting a second resecting guide over the second k-wire and a fourth k-wire inserted in the second bone to align the second resecting guide with the first end of the second bone.

In another aspect, the first bone is a metatarsal, the second bone is a medial cuneiform bone, the deformed configuration of the first and second bones includes a bunion and the corrected configuration of the first and second bones corrects the bunion.

In another aspect, the second guide adjusts an angle of the first bone in three orthogonal planes between the deformed configuration and the corrected configuration.

In another aspect, the second guide adjusts a position of the first bone in three orthogonal planes between the deformed configuration and the corrected configuration.

In another aspect, the method includes centering the first guide between the first bone and the second bone by inserting a centering k-wire through a centering cannula on the first guide.

In another aspect, the method includes removing the first guide from the first and second k-wires includes at least partially disassembling the first guide.

In another aspect, the method includes scanning the first bone and the second bone in the deformed configuration to render a 3D model thereof including a first virtual bone and a second virtual bone in a virtual deformed configuration, adjusting the first virtual bone and the second virtual bone in the 3D model to align the first virtual bone and the second virtual bone in a virtual corrected configuration, fixing a first virtual axis relative to the first virtual bone and fixing a second virtual axis relative to the second virtual bone in the virtual corrected configuration, the first virtual axis is parallel with the second virtual axis, and returning the first and second virtual bones to the virtual deformed configuration, the first and second virtual axes defining a correction factor therebetween in the virtual deformed configuration.

In another aspect, the method includes identifying a virtual resection plane where the first virtual bone and the second virtual bone overlap in the virtual corrected configuration, and fixing the first virtual axis relative to the first virtual bone includes aligning the first virtual axis parallel with the virtual resection plane.

In another aspect, the method includes forming the first guide based on the correction factor.

In another aspect, the correction factor includes a first virtual vector passing through a first virtual point in a virtual coordinate plane and a second virtual vector passing through a second virtual point in the virtual coordinate plane.

In another aspect, forming the first guide includes correlating the virtual coordinate plane with a coordinate plane of the first guide such that the first axis corresponds with the first virtual vector and the first virtual point and the second axis aligned corresponds with the second virtual vector and the second virtual point.

In another aspect, each of the correction factors includes a position vector and two direction vectors corresponding to the first and second axis of the respective guides within the plurality of guides.

In another aspect, the first guide is selected from a plurality of guides, each of the plurality of guides has a different angle between the first and second axes.

According to another aspect, a method of manufacturing a kit for correcting alignment between a first bone and a second bone includes receiving a correction factor, the correction factor including a first virtual vector passing through a first virtual point in a virtual coordinate plane and a second virtual vector passing through a second virtual point in the virtual coordinate plane.

A first guide is formed based on the correction factor, the first guide including a first end portion having a first cannula aligned along a first axis and a second end portion having a second cannula aligned along a second axis. The first axis corresponds to the first virtual vector and the first virtual point and the second axis corresponds to the second virtual vector and the second virtual point, the first and second axes is non-parallel. The first guide is configured such that a first k-wire inserted through the first cannula intersects the first bone and a second k-wire inserted through the second cannula intersects the second bone in a deformed configuration.

In another aspect, the method includes receiving dimensions of a second guide, the second guide including a first end portion with a first cannula and a second end portion with a second cannula. The first cannula is parallel with the second cannula. The first guide is configured such that when sliding the second guide over the first and second k-wires, the first and second k-wires are received within the respective first and second cannula of the second guide and the second guide re-aligns the first and second bones into a corrected configuration.

In another aspect, the method includes receiving a scan of the first bone and the second bone in the deformed configuration to render a 3D model thereof including a first virtual bone and a second virtual bone in a virtual deformed configuration. The first virtual bone and the second virtual bone are adjusted in the 3D model to align the first virtual bone and the second virtual bone in a virtual corrected configuration. A first virtual axis is fixed relative to the first virtual bone and a second virtual axis is fixed relative to the second virtual bone in the virtual corrected configuration. The first virtual axis is parallel with the second virtual axis. The first and second virtual bones are returned to the virtual deformed configuration along with the first and second virtual axes defining the first and second virtual vectors and the first and second virtual points, respectively, of the correction factor.

In another aspect, the method includes identifying a virtual resection plane where the first virtual bone and the second virtual bone overlap in the virtual corrected configuration and fixing the first virtual axis relative to the first virtual bone includes aligning the first virtual axis parallel with the virtual resection plane.

According to another aspect of the disclosure, a kit for correcting alignment between a first bone and a second bone by fusing a joint between the first bone and the second bone includes a first guide. The first guide includes a first end portion with a first cannula aligned along a first axis and a second end portion with a second cannula aligned along a second axis. The first axis is non-parallel with the second axis. The first guide is configured such that inserting a first k-wire through the first cannula intersects the first bone and inserting a second k-wire through the second cannula intersects the second bone when the first and second bones are in a deformed configuration. A second guide includes a first end portion with a first cannula and a second end portion with a second cannula. The first cannula can be parallel with the second cannula. The second guide is configured such that when the first k-wire is fixed within the first bone and the second k-wire is fixed within the second bone in the deformed configuration, sliding the second guide over first and second k-wires, with the first and second k-wires is received within the respective first and second cannula of the second guide, re-aligns the first and second bones into a corrected configuration.

In another aspect, a stabilizing wire fixes the first and second bones in the corrected configuration by insertion into the first and second bones.

In another aspect, a bone plate with a first end configure[d to be attached with the first bone and a second end of the bone plate configured to be attached with the second bone retains the first and second bones in the corrected configuration.

In another aspect, a bone plate clip inserts into the first and second bones in the corrected configuration.

In another aspect, a first resecting guide aligns a resecting tool with a resection location on the first bone.

In another aspect, the first resecting guide includes first and second cannulas configured to be advanced over the first k-wire and a third k-wire, the third k-wire is parallel with the first k-wire.

In another aspect, a second resecting guide aligns the resecting tool with a resection location on the second bone.

According to another aspect, a method for correcting alignment between a first bone and a second bone by fusing a joint between the first bone and the second bone includes aligning a first end portion of a first guide with the first bone. The first end portion has a first cannula and a second cannula aligned in a first direction. A first k-wire is inserted through the first cannula and into the first bone and a second k-wire through the second cannula and into the first bone. A first end of the first bone is resected through a slot to form a first resected face. The slot aligns with the first end of the first bone by the first and second k-wires. A third k-wire and a fourth k-wire insert through the first guide into the second bone. A first end of the second bone is resected to form a second resected face. A second guide slides over the first, second, third and fourth k-wires to adjust a position of the first and second bones such that the first and second resected faces abut in a corrected configuration. The first and second bones are fixed in the corrected configuration.

In another aspect, the method includes fixing the first and second bones in the corrected configuration by inserting a stabilizing wire into the first and second bones.

In another aspect, the method includes fixing the first and second bones in the corrected configuration by attaching a first end of a bone plate with the first bone and a second end of the bone plate with the second bone such that the first and second bones are retained in the corrected configuration.

In another aspect, the method includes sliding the second guide over the first, second, third and fourth k-wires to translate the first resected face towards the second resected face.

In another aspect, the method includes sliding the second guide over the first, second, third and fourth k-wires to rotate alignment between the first bone and the second bone.

In another aspect, the third k-wire and the fourth k-wire are inserted into the second bone through a second end portion of the first guide including a third cannula and a fourth cannula. The third and fourth cannula are aligned in a second direction.

In another aspect, the first end of the second bone is resected through the slot. The slot is aligned with the first end of the second bone by the third and fourth k-wires.

In another aspect, the slot is on a resection guide including first and second apertures configured to align with the first and second k-wires.

In another aspect, the first bone is a metatarsal, the second bone is a medial cuneiform bone and the corrected configuration of the first and second bones corrects a bunion.

In another aspect, the second guide adjusts an angle of the first bone in three orthogonal planes between a deformed configuration and the corrected configuration.

In another aspect, the method includes removing the first guide from the first and second k-wires after resecting the first end of the second bone to form the second resected face.

In another aspect, the method includes removing the second guide and the first, second, third, and fourth k-wires from the first and second bones after fixing the first and second bones in the corrected configuration.

According to another aspect, a method for correcting alignment between a first bone and a second bone by fusing a joint between the first bone and the second bone includes positioning a cutting guide in a first position proximate to a first end of the first bone, the cutting guide including a cutting slot and a first and second cannula through the cutting guide. The cutting guide in the first position includes a first and second k-wire positioned through the first and second cannula and into the first bone. A first end of the first bone is resected through the cutting slot to form a first resected face. The cutting guide is removed from the first and second k-wires. The cutting guide is positioned in a second position proximate to a first end of the second bone. The cutting guide in the second position includes a third and fourth k-wires positioned through the first and second cannula and into the second bone. A first end of the second bone is resected through the cutting slot to form a second resected face. The cutting guide is removed from the third and fourth k-wires. A second guide slides over the first, second, third and fourth k-wires. The second guide adjusts a position of the first and second bones such that the first and second resected faces abut in a corrected configuration. The first and second bones are fixed in the corrected configuration.

In another aspect, positioning a first end portion of a first guide with the first bone, the first end portion having a third cannula and a fourth cannula, the third and fourth cannula aligned in a first direction and inserting the first k-wire through the third cannula and into the first bone and the second k-wire through the fourth cannula and into the first bone.

In another aspect, positioning a second end portion of the first guide with the second bone, the second end portion having a fifth cannula and a sixth cannula, the fifth and sixth cannula aligned in a second direction and inserting the third k-wire through the fifth cannula and into the second bone and the fourth k-wire through the sixth cannula and into the second bone.

In another aspect, fixing the first and second bones in the corrected configuration includes inserting a stabilizing wire into the first and second bones.

In another aspect, fixing the first and second bones in the corrected configuration includes attaching a first end of a bone plate with the first bone and a second end of the bone plate with the second bone such that the first and second bones are retained in the corrected configuration.

In another aspect, sliding the second guide over the first, second, third and fourth k-wires translates the first resected face towards the second resected face.

In another aspect, sliding the second guide over the first, second, third and fourth k-wires rotates the first bone relative to the second bone to adjust an alignment therebetween.

BRIEF DESCRIPTION OF THE DRAWINGS

Various examples are depicted in the accompanying drawings for illustrative purposes, and should in no way be interpreted as limiting the scope of the examples. Various features of different disclosed examples can be combined to form additional examples, which are part of this disclosure.

FIG. 27 shows a method of calculating a correction factor using a virtual model;

DETAILED DESCRIPTION

Overview

Bunion correction or repair is a common surgery with over 100,000 surgeries performed annually in the US. Many surgical procedures for bunion repair are invasive and painful, requiring an incision of several inches and a long period of convalescence, of up to 10-12 weeks. Minimally invasive surgery has been performed in orthopedics for decades. One common procedure is known as a Lapidus bunionectomy. In a Lapidus bunionectomy, the bunion is corrected at the great toe by adjusting alignment at the first tarsometatarsal joint.

The metatarsal can also be stabilized using bone screws and/or a plate to facilitate fusion between the metatarsal and the medial cuneiform bone.

However, existing Lapidus bunionectomy procedures have various drawbacks and risks. These drawbacks include requiring more than minimally invasive surgery, the use of a realignment apparatus that exhibits little control over rotation and relative angles of the metatarsal bone, procedures that rely on in-surgery trial-and-error to identify the best alignment of the patient's foot bones and in-surgery judgment to identify locations for performing resections, lack of customization to account for individual patient foot conditions, and/or a lack of usable guides for performing pre-planned resections of the foot bones. Various aspects of the bone repositioning systems and procedures described herein overcome and improve upon these existing procedures, leading to better patient outcomes.

The various features and advantages of the systems, devices, and methods for bone repositioning described herein will become more fully apparent from the following description of the examples illustrated in the figures. These examples are intended to illustrate the principles of this disclosure, and this disclosure should not be limited to merely the illustrated examples. The features of the illustrated examples can be modified, combined, removed, and/or substituted as will be apparent to those of ordinary skill in the art upon consideration of the principles disclosed herein.

Deformation Correction Procedures

Figure 1:
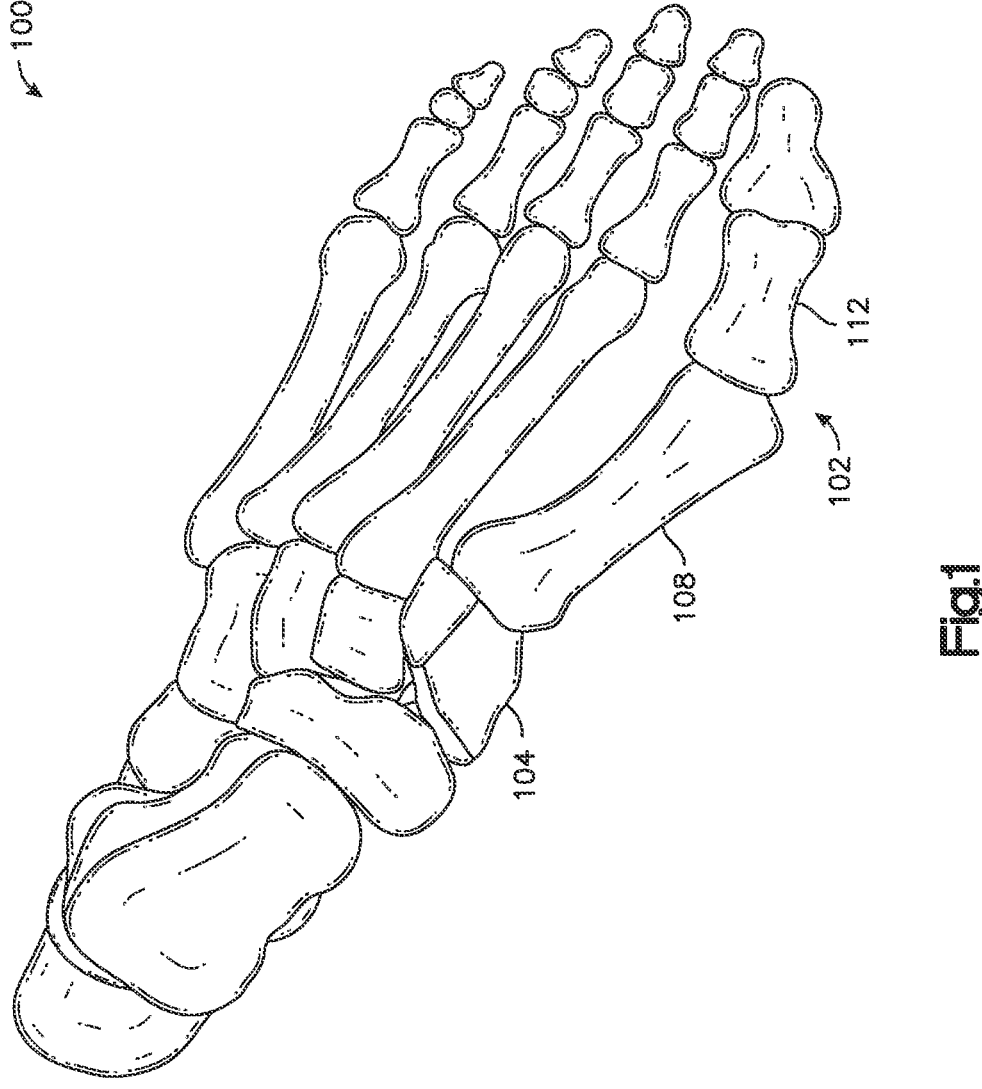
FIG. 1 shows a top view of a patient's foot in a deformed configuration.
Figure 2B:
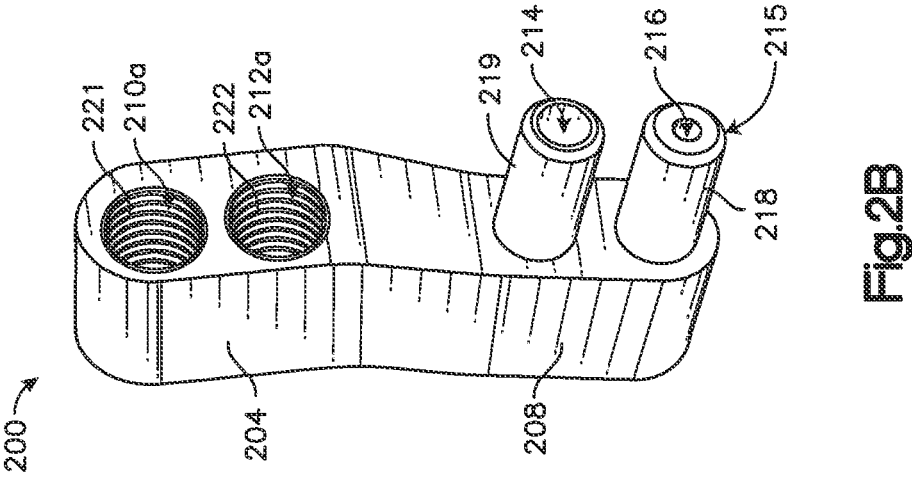
FIG. 2B shows a rear perspective view of the alignment guide.
Figure 2A:
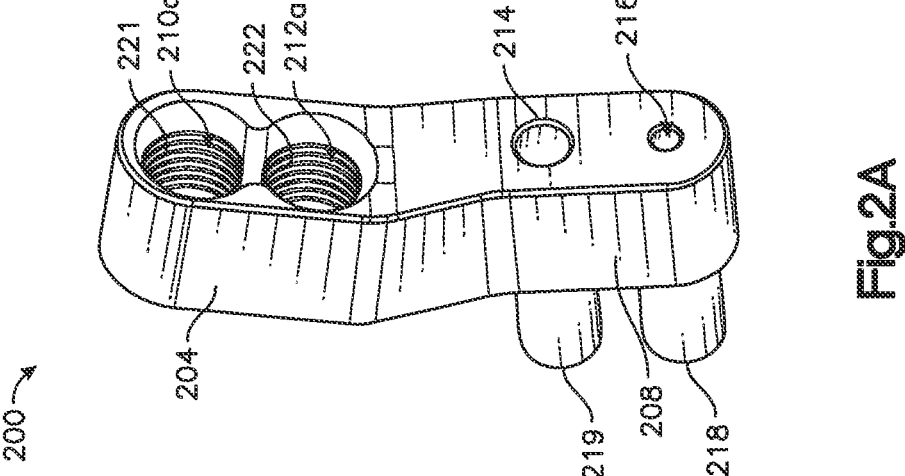
FIG. 2A shows a front perspective view of the alignment guide.
Figure 3B:
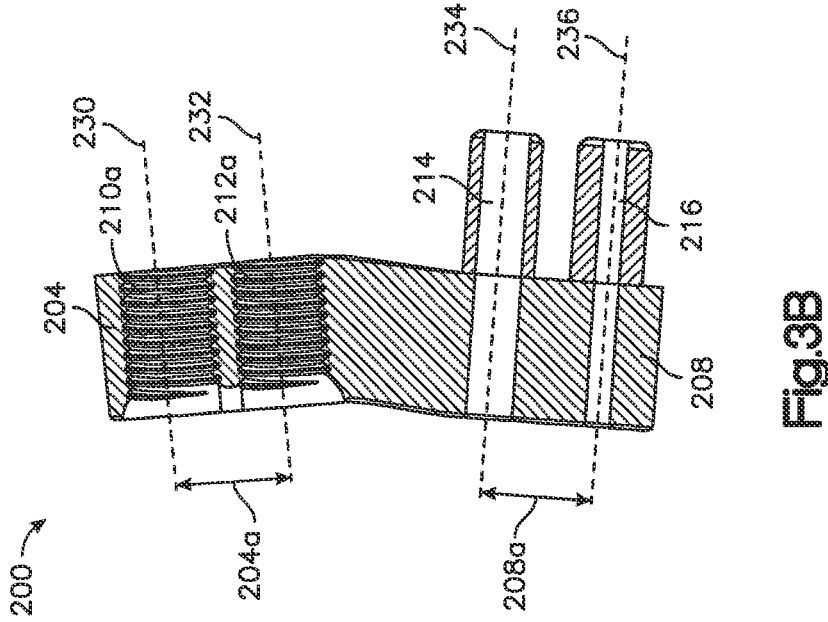
FIG. 3B shows a section view taken along the line 3B-3B of FIG. 3A.
Figure 3A:
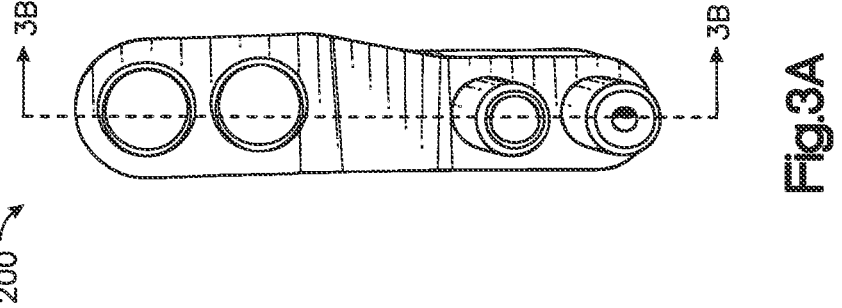
FIG. 3A shows a front view of the alignment guide.

FIG. 1 shows a skeletal view of a patient's foot 100 having one or more bones in an initial or deformed configuration 102. The deformed configuration 102 can be a bunion, as illustrated. In other examples, the deformed configuration can be a post-traumatic malunion of a fracture, or other single bone deformity that can be corrected across an osteotomy. The deformed configuration 102 can be a misalignment between a metatarsal 108 and a phalanx 112 of the patient's great toe. The metatarsal 108 can be at an angle with respect to the phalanx at 112. A high degree of misalignment between the metatarsal 108 and the phalanx 112 can lead to severe pain and rubbing and discomfort and other problems in the patient's foot 100. Accordingly, it can be beneficial to correct the alignment between the metatarsal 108 and the phalanx 112 of the great toe.

The patient's foot 100 can further include a medial cuneiform bone 104. The medial cuneiform bone 104 can be connected with a proximal end of the first metatarsal 108 (e.g., by one or more ligaments). A tarsometatarsal (TMT) joint joins the medial cuneiform bone 104 to the first metatarsal 108. Thus, reference below is made to the TMT joint. Therefore, while the medial cuneiform bone 104 and the first metatarsal 108 can define first and second bones, respectively, it should be appreciated that first and second bones can apply to any alternative anatomical bones or bone segments that are separated by any suitable joint or, alternatively, an osteotomy. Accordingly, description below to the TMT joint can apply to other joints or, alternatively, an osteotomy. A distal direction is defined from the medial cuneiform bone 104 toward the metatarsal 108. Conversely, a proximal direction is defined from the metatarsal 108 toward the medial cuneiform bone 104. FIGS. 1-22 illustrate systems and methods of correcting alignment between the medial cuneiform bone 104 and the metatarsal 108. In turn, proper alignment between the medial cuneiform bone 104 and the metatarsal 108 can correct alignment between the metatarsal 108 and the phalanx 112. Accordingly, the deformed configuration 102 of the patient's foot 100 can be corrected. The present disclosure relates to systems and methods for correcting the deformed configuration 102. Moreover, the systems and methods described herein can be used more generally for correcting alignment between any two bones a patient's body.

As shown in FIGS. 2A-4, the system for correcting alignment in the patient's foot 100 can include an alignment guide 200. The alignment guide 200 can be formed of a rigid material. The alignment guide 200 can include a first end portion 204. The first end portion 204 can include one or more apertures 210a, 212a. Although two apertures are described and illustrated, more or fewer apertures can be included on the first end portion 204. The apertures 210a, 212a can include internal threads 221, 222, respectively. The apertures 210a, 212a can be chamfered on one or both sides of the alignment guide 200. The apertures 210a, 212a can extend all the way through the alignment guide 200. The apertures 210a, 212a can be aligned along respective axes 230, 232. The axes 230, 232 can be parallel. Alternatively, the axes 230, 232 can be converging. The axes 230, 232 can be spaced apart a distance 204a. The distance 204a can be based on a length of the medial cuneiform bone 104.

Figure 4:
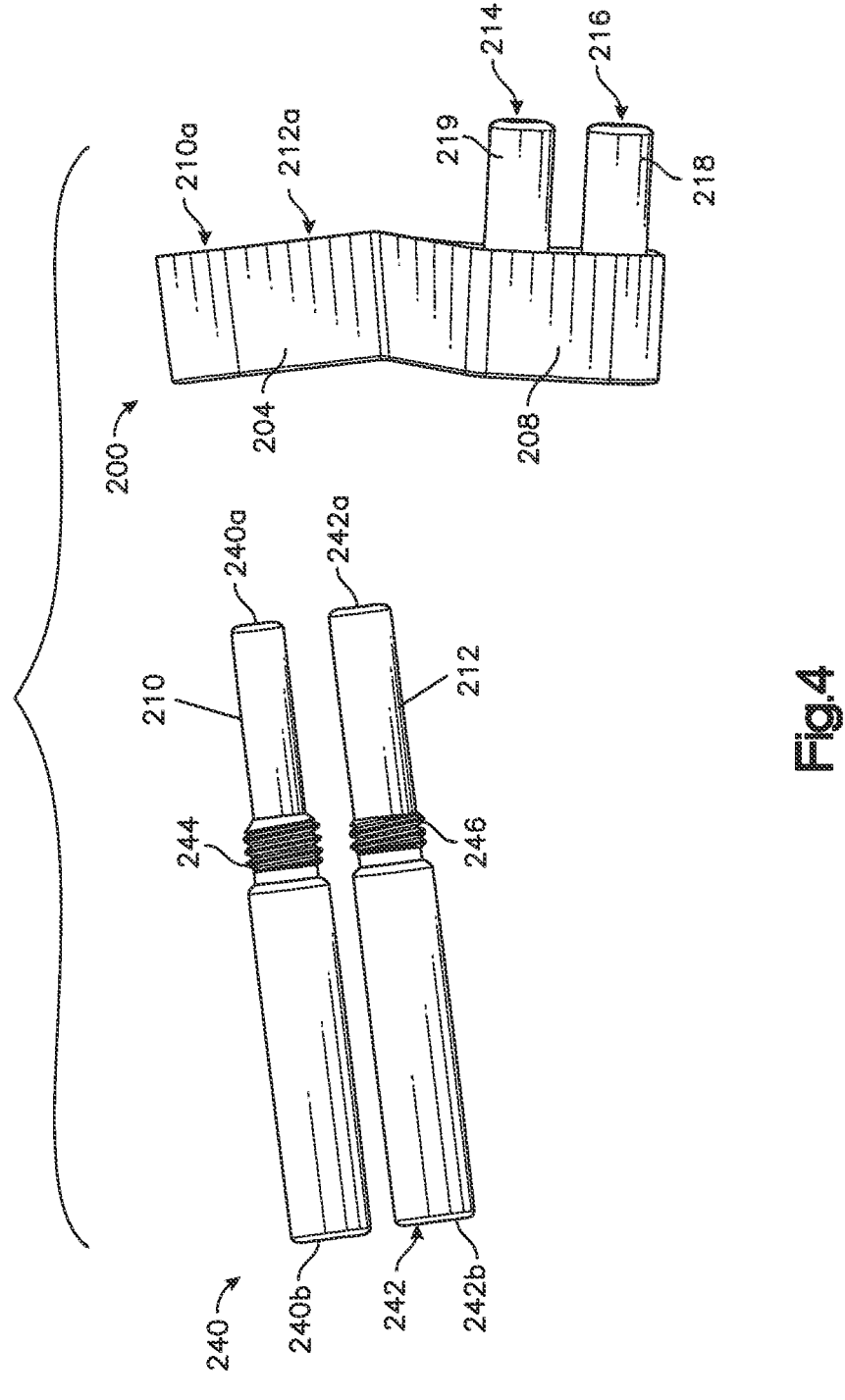
FIG. 4 shows an exploded view of the alignment guide.

As shown in FIG. 4, the alignment guide 200 can define at least one proximal cannula 213 (see FIG. 5), such as first and second proximal cannulas 210 and 212. The first and second cannulas 210 and 212 can be referred to as first and second proximal cannulas, respectively. In particular, the alignment guide 200 can include one or more removable tubes 240, 242. The removable tubes 240 can include a first end 240a and a second end 240b. The first end 240a can be received within the aperture 210a. The removable tube 240 can include a threaded portion 244. The threaded portion 244 can engage with the internal threads 221 of the aperture 210a. The removable tubes 242 can include a first end 242a and a second end 242b. The first end 242a can be received within the aperture 212a. The removable tube 240 can include a threaded portion 246. The threaded portion 246 can engage with the internal threads 222 of the aperture 212a.

The removable tube 240 can define the first cannula 210. When installed within the aperture 210a, the first cannula 210 can be aligned along the axis 230 of the aperture 210a. The removable tube 242 can define the second cannula 212. When installed within the aperture 212a, the second cannula 212 can be aligned along the axis 232 of the aperture 212a. The first and second cannulas 210 and 212 can define different diameters therethrough. The cannula 212 can have a greater diameter than the cannula 210 (or vice-versa). In other implementations, the first and second cannulas 210 and 212 can define the same different diameters therethrough. In other implementations, the first and second cannulas 210 and 212 can define varying diameters therethrough.

The alignment guide 200 can include a second portion 208. The second end portion 208 can include at least one distal cannula 215 such as third and fourth cannulas 214 and 216. The second portion 208 can define a distal end portion of the alignment guide 200, and the at least one cannula can define at least one distal cannula. The third and fourth cannulas 214 and 216 can be defined through a body of the alignment guide 200 and/or through respect extensions 219, 218 thereof. Although two cannula are described and illustrated, more or fewer cannulas can be included on the second end portion 208. Moreover, the second end portion 208 can include removable inserts or removable portions (e.g., removable tubes) around the third and fourth cannula 214 and 216. The third and fourth cannulas 214 and 216 can also be referred to as first and second distal cannulas 214 and 216 respectively.

The third and fourth cannulas 214 and 216 can extend all the way through the alignment guide 200 (e.g., including the extensions 218, 219). The third and fourth cannulas 214 and 216 can define different diameters therethrough. The third cannula 214 can have a greater diameter than the fourth cannula 216 (or vice-versa). In other implementations, the third and fourth cannulas 214 and 216 can define the same different diameters therethrough. In other implementations, the third and fourth cannulas 214 and 216 can define varying diameters therethrough.

The third and fourth cannula 214 and 216 can be aligned along respective parallel axes 234, 236. The axes 234, 236 can be spaced apart a distance 208a. The distance 204a can be based on a length of the metatarsal bone 108.

Figure 5:
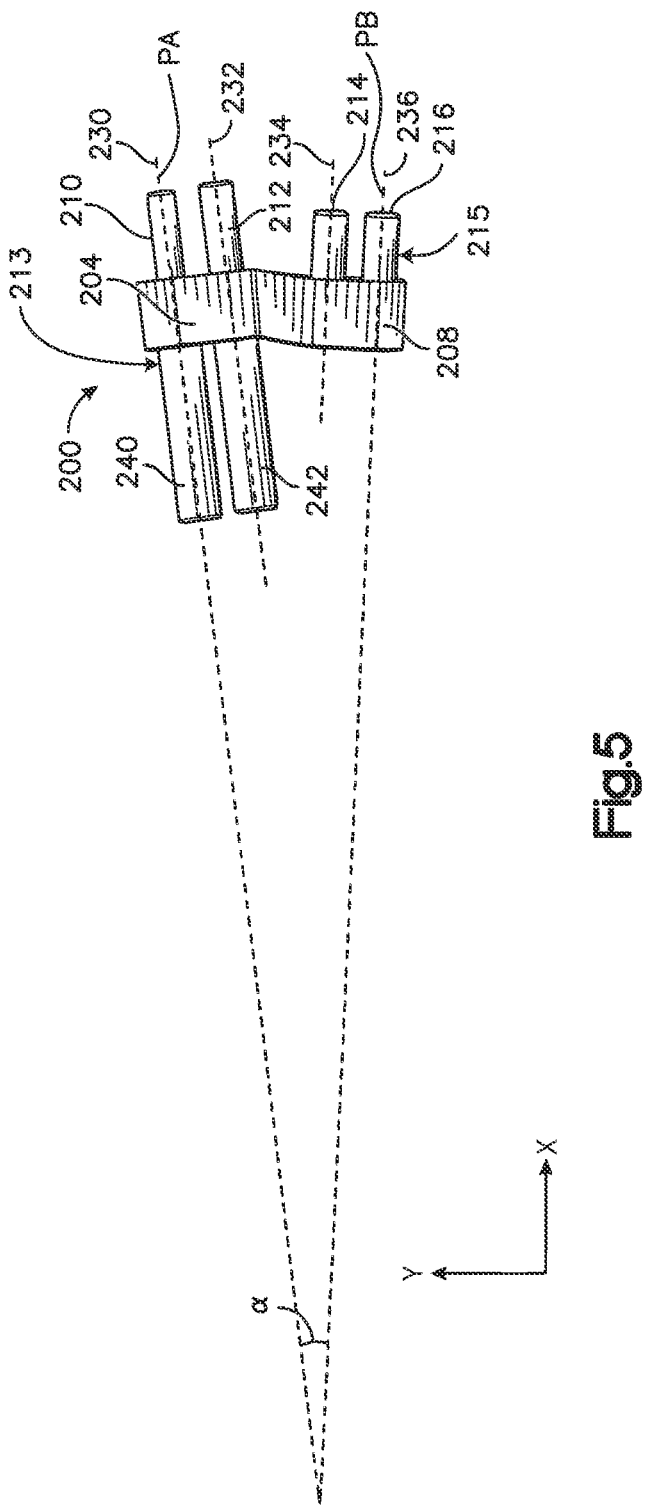
FIG. 5 shows an angle between cannula of the alignment guide.
Figure 6:
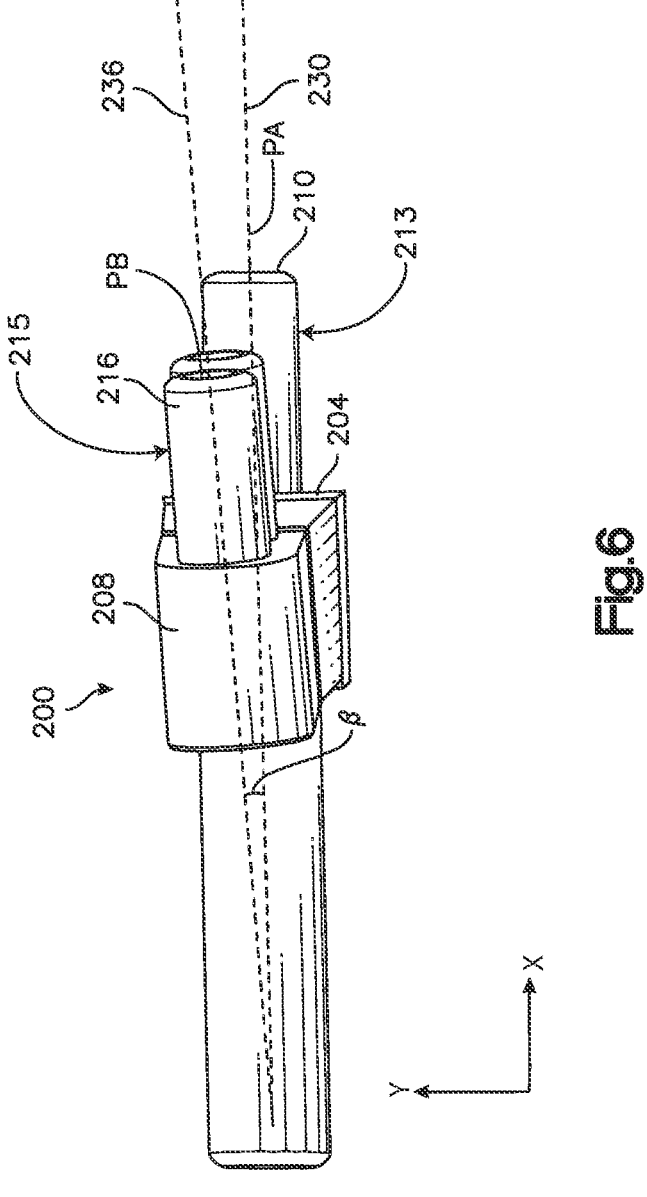
FIG. 6 shows a second angle between cannula of the alignment guide.
Figure 7:
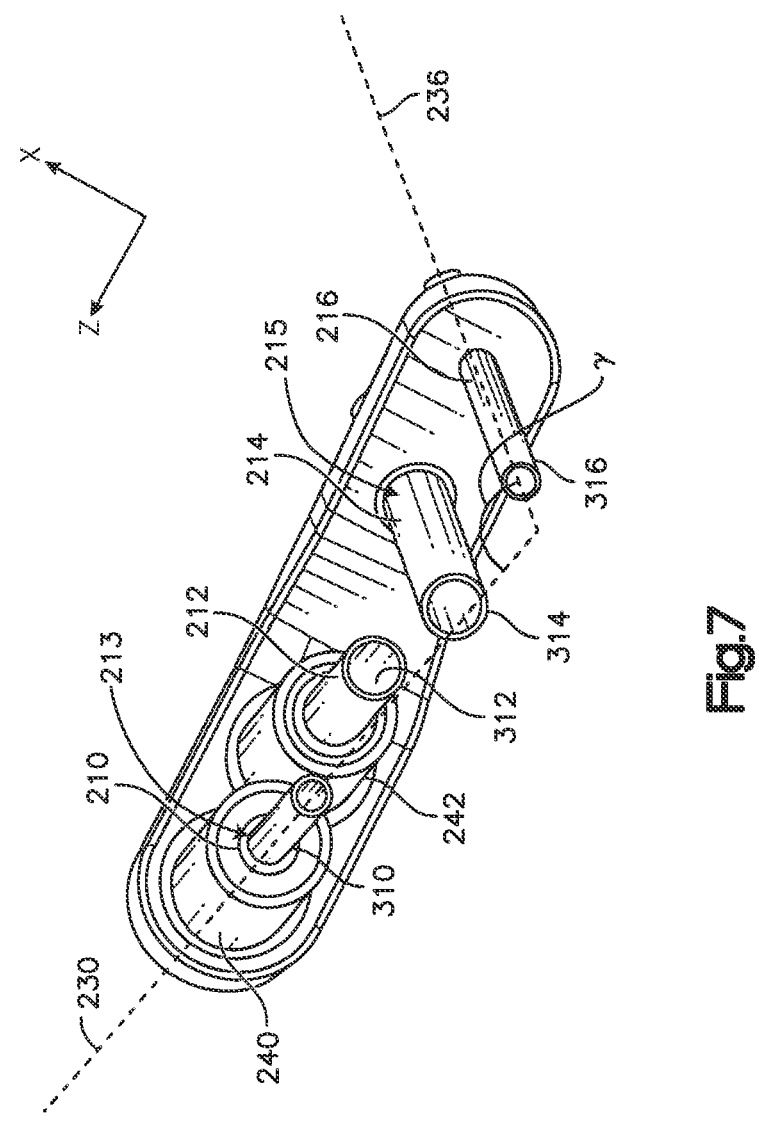
FIG. 7 shows a third angle between cannula of the alignment guide.

FIGS. 5-7 shows the assembled alignment guide 200. The first end portion 204 can define a position and orientation of a first set of cannula (e.g., cannula 210, 212). The second end portion 208 can define a position and orientation of a second set of cannula (e.g., the third and fourth cannula 214 and 216). The first set of cannula and the second set of cannula can be offset from each other and/or angled with respect to each other.

FIG. 5 shows an angle α between the axis 230 of the first cannula 210 and the axis 236 of the fourth cannula 216. The angle α defines the relative orientation angle between the first set of cannula on the first end 204 and the second set of cannula on the second end 208. The angle α can be defined in an z-x plane in a Cartesian coordinate system (having x, y, and z axes). The cannula first 210 can include a point PA. Alternatively, the point PA can be any fixed position along the first cannula 210. The point PA can have an x, y, and z coordinate location in a Cartesian coordinate system (having x, y, and z axes). The cannula 216 can include a point PB. Alternatively, the point PB can be any fixed position along the fourth cannula 216. The point PB can have an x, y, and z coordinate location in the Cartesian coordinate system. The points PA and PB can define a relative position of the axes 230, 236 in the Cartesian coordinate system.

FIG. 6 shows an angle β between the axis 230 of the first cannula 210 and the axis 236 of the fourth cannula 216. The angle β defines the relative orientation angle between the first set of cannula on the first end 204 and the second set of cannula on the second end 208 in a y-x plane. FIG. 7 shows an angle γ between the axis 230 of the first cannula 210 and the axis 236 of the fourth cannula 216. The angle γ defines the relative orientation angle between the first set of cannula on the first end 204 and the second set of cannula on the second end 208 in a y-z plane.

Together, the relative positions of the points PA and PB and at least two of the relative angles α, β, and γ can define the axis of the cannula on the alignment guide 200. Using the proper selection of the relative angles α, β, and/or γ, and/or the relative positions of the points PA and PB of the alignment guide 200 can be used to correctly align the bones in the patient's foot 100, as described further below.

Figure 8:
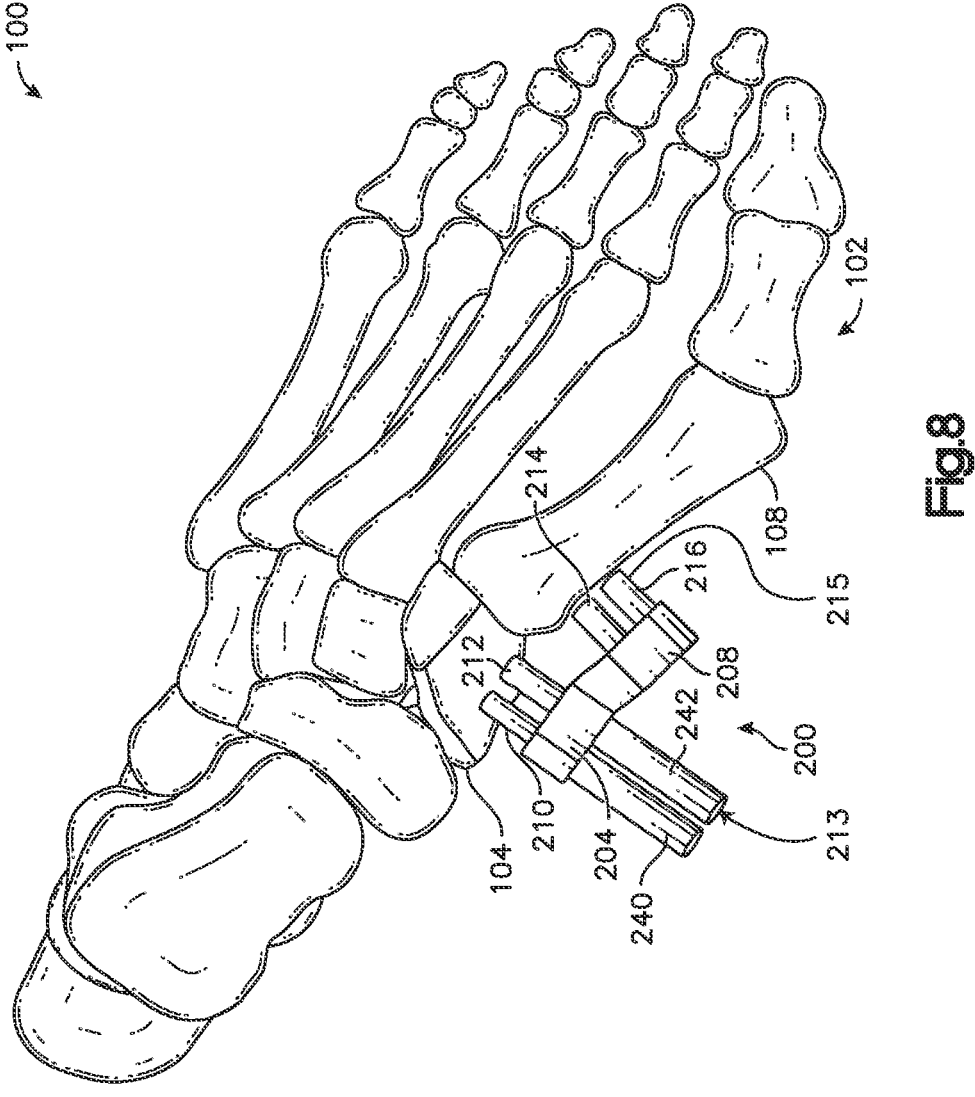
FIG. 8 shows an alignment guide aligned with a medial cuneiform bone and a metatarsal bone in the patient's foot.
Figure 9:
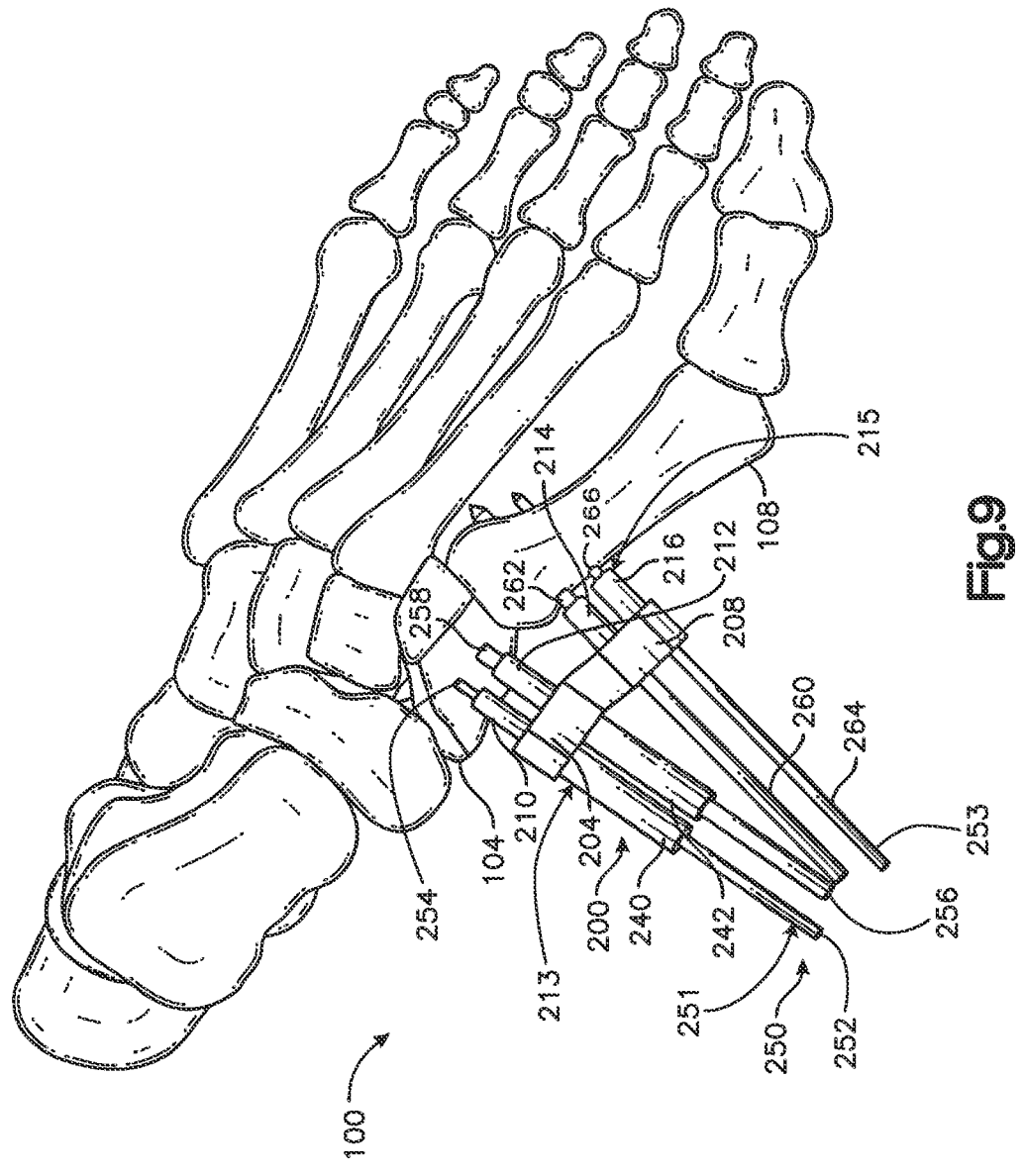
FIG. 9 shows insertion of a plurality of k-wires into the medial cuneiform bone and the metatarsal bone through the alignment guide.

As shown in FIG. 8, the alignment guide 200 can be aligned with the patient's foot 100. The first end portion 204 can be generally aligned with the medial cuneiform bone 104. The second end portion 208 can be generally aligned with the metatarsal 108. As shown in FIG. 9, a plurality of temporary fixation elements such as k-wires 250 can be extended through respective cannula of the alignment guide 200. At least one of the k-wires can extend through a respective cannula and into the respective medial cuneiform 104, and at least another of the k-wires can extend through a respective cannula of the alignment guide 200 and into the metatarsal bone 108.

At least one proximal temporary fixation device, such as at least one proximal k-wire, can be inserted through the at least one proximal cannula of the alignment guide 200 and into the cuneiform bone 104. For instance, a first k-wire 252 can be driven through the cannula 210 and into the medial cuneiform 104. The first k-wire 252 can be inserted at a first insertion point 254 on the medial cuneiform bone 104. A second k-wire 256 can be driven through the cannula 212 and into the medial cuneiform bone 104. The second k-wire 256 can be inserted through the medial cuneiform bone 104 at a second insertion point 258. The first and second k-wires 252 and 256 can be referred to as first and second proximal k-wires respectively. The first and second insertion points 254 and 258 can be referred to as proximal insertion points.

At least one distal temporary fixation device, such as at least one distal k-wire, can be inserted through the at least one distal cannula of the alignment guide 200 and into the metatarsal 108. A third k-wire 260 can be driven through the cannula 214 and into the metatarsal 108. The third k-wire 260 can intersect and be inserted into the metatarsal 108 at a third insertion point 262. A fourth k-wire 264 can be driven through the fourth cannula 216 and into the metatarsal 108. The fourth k-wire 264 can be inserted into the metatarsal 108 at a fourth insertion point 266. The third and fourth k-wires 260 and 264 can be referred to as first and second distal k-wires respectively. The third and fourth insertion points 262 and 266 can be referred to as first and second distal insertion points respectively. The alignment guide 200 can be positioned such that the first and second cannulas 210 and 212 and the third and fourth cannulas 214 and 216, and thus the first and second k-wires 252 and 256 and the third and fourth k-wire 260 and 264, extend medially from the medial cuneiform bone 104 and the first metatarsal 108, respectively. Alternatively, the alignment guide 200 can be positioned such that the first and second cannulas 210 and 212 and the third and fourth cannulas 214 and 216, and thus the first and second k-wires 252 and 256 and the third and fourth k-wire 260 and 264, extend superiorly from the medial cuneiform bone 104 and the first metatarsal 108, respectively, as described below with respect to the alignment guide 300 (see FIGS. 11A-14G).

The first and second k-wires 252, 256 can be parallel with each other, based on the parallel cannula 210, 212. The third and fourth k-wires 260, 264 can be parallel with each other, based on the cannula 214, 216. One or more of the insertion points 254, 258, 262, 266 (e.g., at least one on each bone 104, 108) can be in predetermined locations on the patient's foot. The lengths of the extensions 218, 219 and/or the tubes 240, 242 can provide greater stability to the k-wires 250 that are received therein. Diameters of the k-wires 250 can be sized according to the diameters of the respective cannula of the alignment guide 200 to ensure accurate insertion at angles into the bone 104, 108. Moreover, the k-wires 250 can be matched to the correct cannula based on different diameter sizes.

The first and second k-wires 252 and 256 can be referred to as proximal k-wires 251, and the third and fourth k-wires 260 and 264 can be referred to as distal k-wires 253 that are disposed distal of the proximal k-wires 251. The first and second cannulas 210 and 212 of the alignment guide 200 can be referred to as proximal cannulas of the alignment guide. The third and fourth cannulas 214 and 216 of the alignment guide can be referred to as distal cannulas of the alignment guide 200 that are disposed distal of the proximal cannulas of the alignment guide 200. The proximal k-wires 251 are configured to be inserted into respective ones of the proximal cannulas 213 and into the cuneiform bone 104. The distal k-wires 253 are configured to be inserted into respective ones of the distal cannulas and into the metatarsal 108. While the system can include two proximal k-wires 251 and two distal k-wires 253 in one example, it should be appreciated that the system can include any number of proximal and distal k-wires including at least one. Thus, at least one proximal k-wire 251 can be inserted through at least one proximal cannula 213 and into the cuneiform bone 104, and at least one distal k-wire 253 can be inserted through at least one distal cannula 215 and into the metatarsal 108.

Figure 10A:
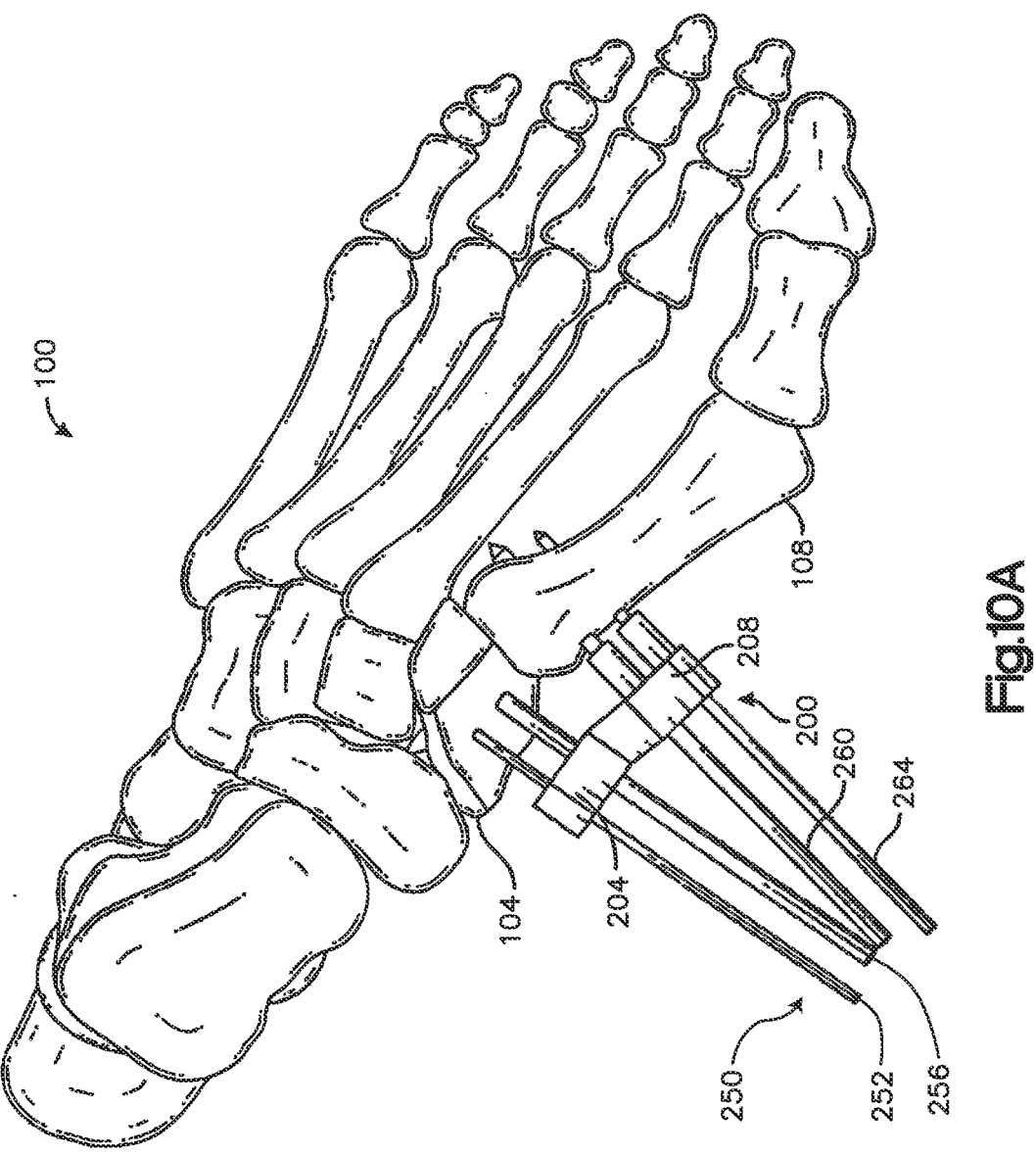
FIG. 10A shows the removal of tubes of the alignment guide.
Figure 10B:
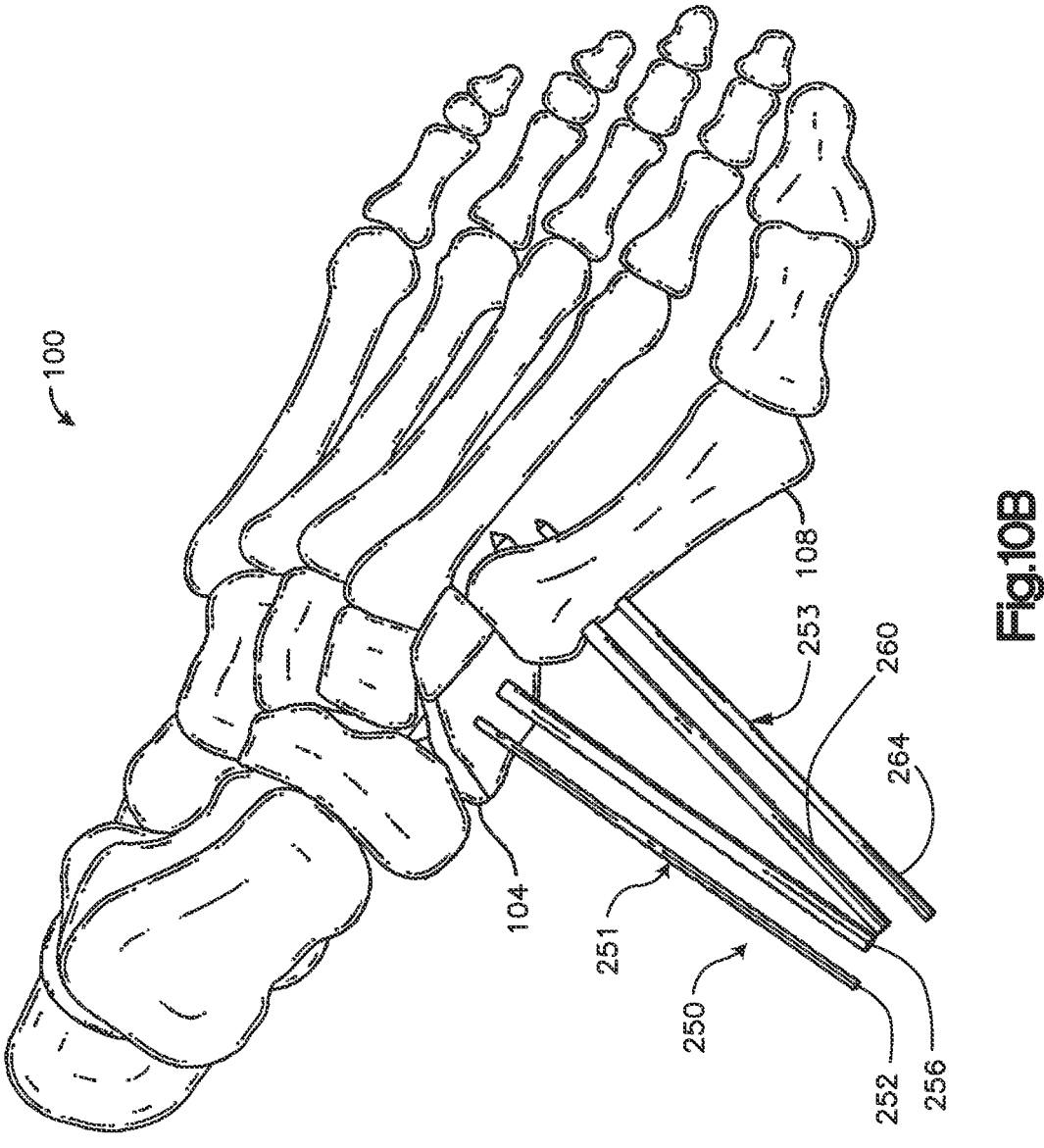
FIG. 10B shows the removal of the alignment guide from the k-wires.

FIG. 10A-10B show removal of the tubes 240, 242 from the first end 204 of the alignment guide 200. The first and second tubes 240, 242 are removed from the first end portion 204 to allow the alignment guide 200 to subsequently be removed from the plurality of k-wires 250 inserted within the medial cuneiform bone and metatarsal bone 108, also referred to as the proximal k-wires 251. FIG. 10B shows the removal of the alignment guide 200 from the k-wires 250. In certain circumstances, without a removable or otherwise deconstructable element, it can be difficult for a user to remove the alignment guide 200 from the plurality of k-wires 250 because of the misalignment between the first and second ends 204, 208. Once the first and second tubes 240 and 242 have been removed, the openings 210*a* and 212*a* (see FIG. 4) have respective sizes greater than those of the proximal k-wires 251, thereby providing clearance between the alignment guide 200 and the proximal k-wires 251. Thus, the alignment guide 200 can ride along the distal k-wires 253 as it is removed, while the clearance allows the alignment guide 200 to be removed from the proximal k-wires 252.

Referring now to FIGS. 11A-14E in general, an alignment guide 300 can be constructed in accordance with an alternative embodiment. The alignment guide 300 can include a guide body 301 and an insert 311 that is configured to be supported by the guide body 301. The guide body 301 can be formed of a rigid material, and in particular can be formed from a solid block of material. Thus, the guide body 301 can define a unitary monolithic one-piece structure. Similarly, the insert 311 can be formed of a rigid material, and in particular can be formed from a solid block of material. Thus, the insert 311 can define a unitary monolithic one-piece structure. As will now be described, the alignment guide 300 can define at least one proximal cannula and at least one distal cannula that are configured to receive respective temporary fixation elements, such as k-wires, that are secured to bones or bone segments, such as the medial cuneiform bone 104 and the first metatarsal 108, respectively at a predetermined relative position. For instance, the at least one proximal cannula can be defined by the guide body 301, and the at least one distal cannula can be defined by the insert 311. Alternatively, the at least one distal cannula can be defined by the guide body 301, and the at least one proximal cannula can be defined by the insert 311. While k-wires are described and shown, it should be appreciated that the temporary fixation elements can be alternatively constructed in any manner as desired. For instance, the temporary fixation elements can define pins, nails, or the like.

Referring now to FIGS. 11A-12J in particular, the alignment guide 300 can include a guide body 301 that defines a bone-facing surface 303 and an outer surface 305 opposite the bone-facing surface 303. The alignment guide has a first or proximal end portion 304 and a second or distal end portion 308. The second end portion 308 extends distally from the first end portion 304.

The alignment guide 300 can include at least one first or proximal cannula, such as a first cannula 310 and a second cannula 312 that extend through the guide body 301 from the outer surface 305 to the bone-facing surface 303. The first and second cannulas 310 and 312 can be referred to as first and second proximal cannulas. In one example, the first and second cannulas 310 and 312 can extend through the first end portion 304. The first and second cannulas 310 and 312 can be arranged such that the second cannula 312 is offset from the first cannula 310 in the distal direction. The first and second cannulas 310 and 312 can extend through the guide body 301 along respective first and second central axes 330 and 332. In one example, the central axes 330 and 332 can be parallel to each other as they extend in a direction from the outer surface 305 to the bone-facing surface 303 (also referred to as a bone-facing direction). Alternatively, the central axes 330 and 332 can diverge from each other as they extend in the bone-facing direction. Alternatively still, the central axes 330 and 332 can converge toward each other as they extend in the bone-facing direction. The cannulas 310 and 312 can be chamfered at either or both of the outer surface 305 and the bone-facing surface 303. The central axes 330 and 332 can be spaced apart from each other along a first direction a distance 307 that is based on a length of the cuneiform bone 104. Therefore, the system can include a kit of alignment guides 300 having different distances 304 as desired. Although the at least one proximal cannula is shown and described as including two cannulas, more or fewer cannulas can be defined by the at least one proximal cannula.

As will be described in more detail below, the first and second cannulas 310 and 312 can each be sized and configured to receive respective first and second k-wires 252 and 256 (see FIG. 14E). The first and second cannulas 310 and 312 can define different diameters therethrough. The first cannula 310 can have a greater diameter than the second cannula 312. Alternatively, the second cannula 312 can have a greater diameter than the first cannula 310. In other implementations, the first and second cannulas 310 and 312 can define the same diameters therethrough. In other implementations, either or both of the first and second cannulas 310 and 312 can define varying diameters therethrough.

It should be appreciated that in one example, the first and second cannulas 310 and 312 can be defined by the guide body 301. In another example described above with respect to the alignment guide 200, the first and second cannulas 310 and 312 can be defined by respective removable tubes of the alignment guide 300 that are inserted into respective apertures of the guide body 301. In both examples, it can be said that the alignment guide 300 defines the first and second cannulas 310 and 312.

The alignment guide 300 can further define at least one second or distal cannula such as third and fourth cannulas 314 and 316. The third and fourth cannulas 314 and 316 can also be referred to as first and second distal cannulas. In particular, the alignment guide 300 can define a receiving aperture 313 that extends through the guide body 301 along the bone-facing direction. For instance, the aperture 313 can extend through the second end portion 308 of the guide body 301. The aperture 313 can be sized and configured to receive the insert 311. In particular, the insert 311 can be removably inserted into the aperture 313. The aperture 313 can be open to a medial side of the second end portion 308 at a side opening 315 that can extend laterally into the second end portion 308. Further, the aperture 313 can extend from the outer surface 305 to the bone-facing surface 303. Respective ends 371 that define the proximal and distal ends of the opening 315 can be disposed outboard of the cannulas of the insert 311, as will now be described.

Figures 13A, 13B:
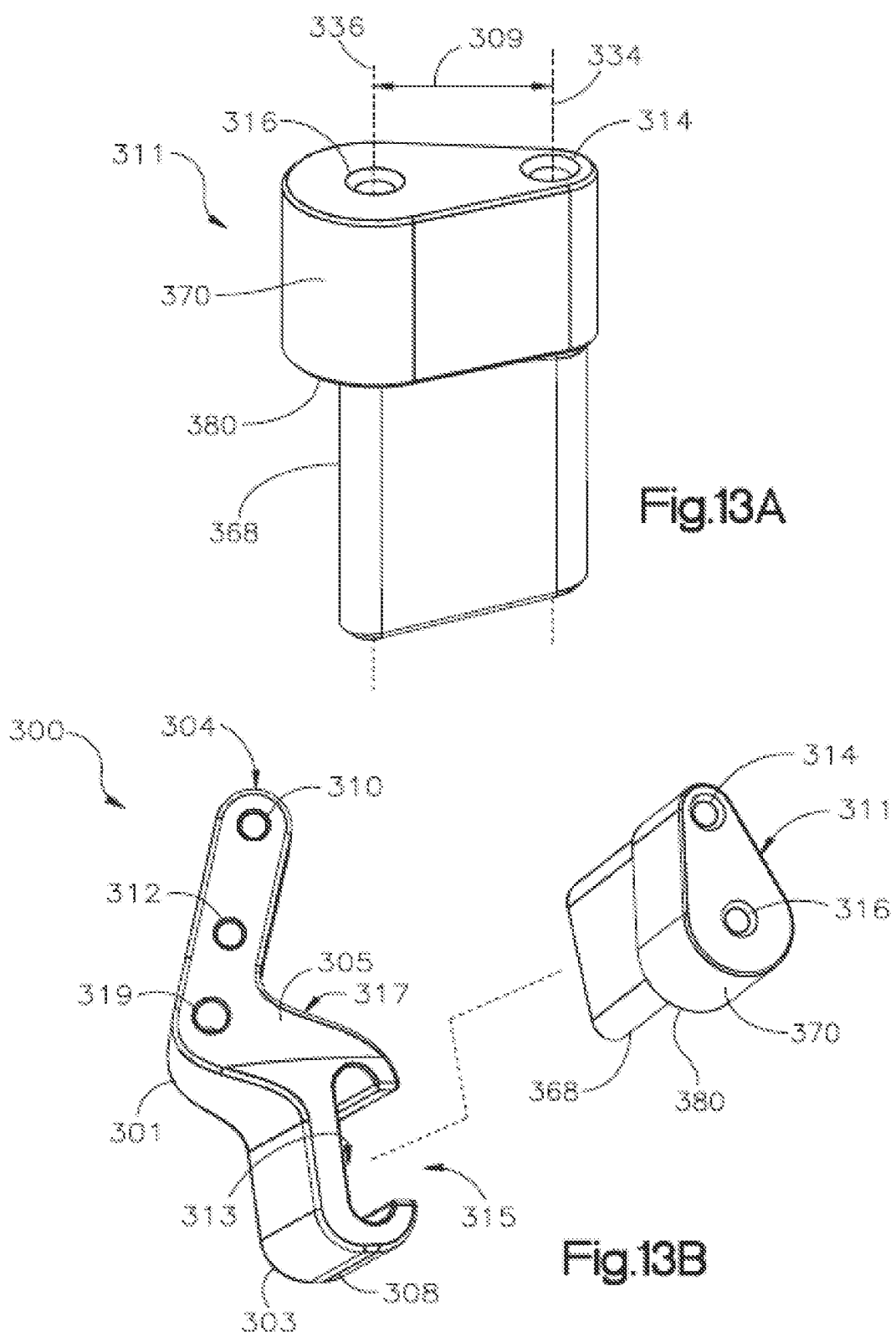
FIG. 13A is a perspective view of the insert of FIG. 11A.
FIG. 13B is an exploded perspective view of the guide body and the insert of FIG. 11A.

Referring now to FIGS. 13A-13B, the insert 311 can define an insert portion 368 and a seat portion 370. The insert portion defines a bone-facing surface 371 of the insert 311, and the seat portion 370 can define an outer surface 373 of the insert 311 that is opposite the bone-facing surface 371. The insert can define third and fourth cannulas 314 and 316 that extend from the outer surface 373 to the bone-facing surface 371. The third and fourth cannulas 314 and 316 can be referred to as first and second distal cannulas, respectively, when the aperture 313 that receives the insert 311 extends through the second end portion 308. Although the insert 311 is illustrated and described as defining two cannulas, the insert 311 can define more or fewer cannulas as desired.

The third and fourth cannulas 314 and 316 can extend along respective third and fourth central axes 334 and 336, respectively, through the insert 311. The third and fourth cannulas 314 and 316 can define different diameters therethrough. The third cannula 314 can have a greater diameter than the fourth cannula 316. Alternatively, the fourth cannula 316 can have a greater diameter than the third cannula 314. In other implementations, the third and fourth cannulas 314 and 316 can define the same different diameters therethrough. In other implementations, either or both of the third and fourth cannulas 314 and 316 can define varying diameters therethrough.

In one example, the central axes 334 and 336 can extend parallel to each other as they extend in a direction from the outer surface 373 to the bone-facing surface 371 (also referred to as a bone-facing direction). Alternatively, the central axes 334 and 336 can diverge from each other as they extend in the bone-facing direction. Alternatively still, the central axes 334 and 336 can converge toward each other as they extend in the bone-facing direction. The axes 334 and 336 can be spaced apart a longitudinal distance 309 along a second direction. The distance 309 can be based on a length of the metatarsal bone 108. The second direction can be different than the first direction along which the first and second axes 330 and 332 are spaced from each other. The orientation and position of the cannulas 310, 312, 314, and 316 can be selected to correct a deformity, such as a bunion as described above. The kit of alignment guides 300 can have different distances 309 as desired. The opening 315 to the aperture 313 can have a longitudinal distance greater than the distance 309 so as to accommodate the distal k-wires upon removal of the guide body 301 from the patient's foot 100. Although the at least one distal cannula is shown and described as including two cannulas, more or fewer cannulas can be defined by the at least one distal cannula. The cannulas 314 and 316 can be chamfered at either or both of the outer surface 373 and the bone-facing surface 371.

Figure 11A:
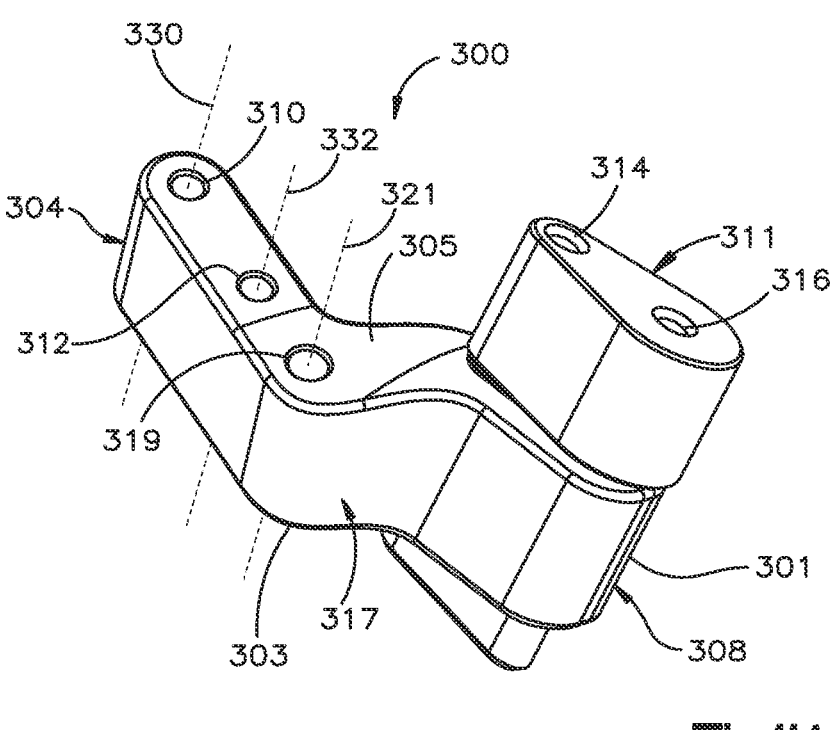
FIG. 11A is a perspective view of an alignment guide including a guide body and an insert in accordance with an alternative embodiment.

The insert portion 368 of the insert 311 can define a shoulder 380. In particular, the seat portion 370 can have a cross-sectional dimension perpendicular to the bone-facing direction that is greater than a corresponding cross-sectional dimension of the aperture 313. Accordingly, the seat portion 370 is sized so that it is not insertable into or through the aperture 313 of the guide body 301 in the bone-facing direction. The insert portion 368 is sized for insertion through the aperture 313 in the bone-facing direction. Therefore, the extent of the seat portion 370 that extends out with respect to the insert portion 368 in a direction perpendicular to the bone-facing direction can define the shoulder 380. The shoulder 380 can extend partially or fully about the insert portion 368 along a direction that is orthogonal to a direction along which the insert portion 368 extends from the seat portion 370. During operation, as shown at FIG. 11A, the insertion portion 368 can be inserted through the aperture 313 until the seat portion 370, and in particular the shoulder 380, abuts the outer surface 305 of the guide body 301, thereby limiting a depth of insertion of the insert 311 through the aperture 313. The aperture 313 can be inwardly tapered as it extends from the outer surface 305 to the bone-facing surface 303, or can be substantially constantly dimensioned in cross-section from the outer surface 305 to the bone-facing surface 303 as desired. The insert 311 can be similarly dimensioned in cross-section so as to substantially match the cross-sectional dimension of the aperture 313. When tapered, the taper can fix the depth of insertion of the insert 311 through the aperture 313. In other examples, the guide body 301 can include a floor portion that extends into or across aperture 313, which can define a seat for the insert 311 so as to fix the depth of insertion of the insert through the aperture 313.

The guide body 301 and the insert 311 can be fabricated in accordance with any suitable method as desired. In one example, the guide body 301 can be made by a rapid-prototyping or CNC machining method to include the aperture 313 and the first and second cannulas 310 and 312 in respective predetermined positions and orientations to correct a deformity of the foot using the methods described herein. As another example, a plurality of blank guide bodies 301 can be fabricated the aperture 313, and the first and second cannulas 310 and 312 can be subsequently drilled or otherwise formed as desired.

Figure 11B:
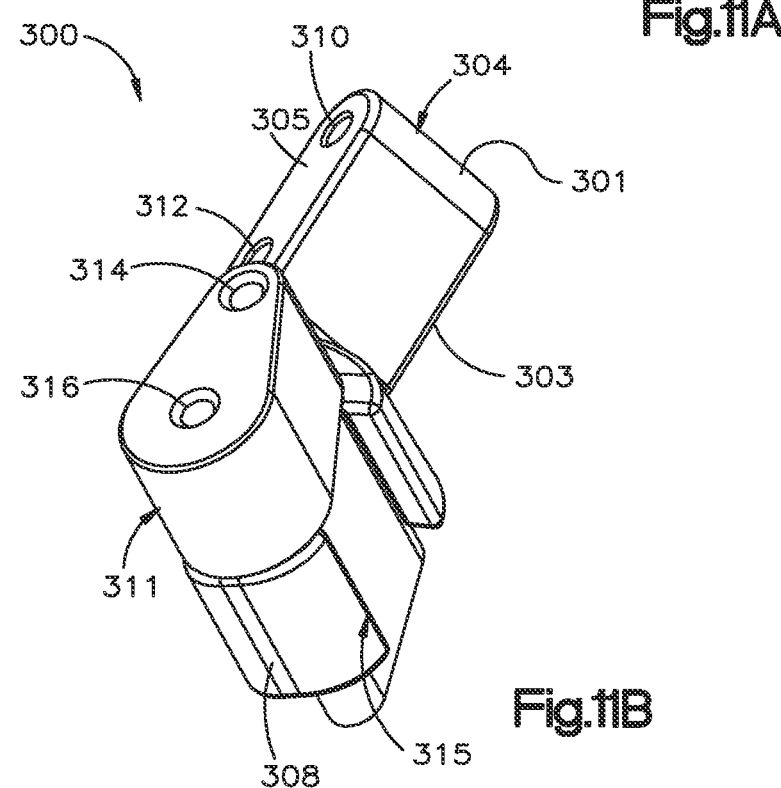
FIG. 11B is another perspective view of the alignment guide illustrated in FIG. 11A.
Figure 12A:
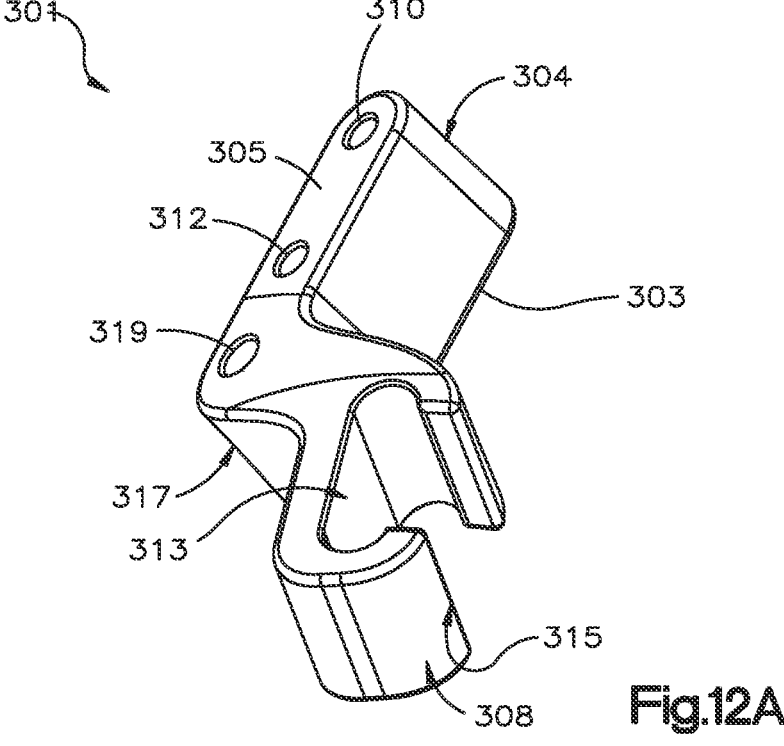
FIG. 12A is a perspective view of the guide body of FIG. 11A.
Figure 12B:
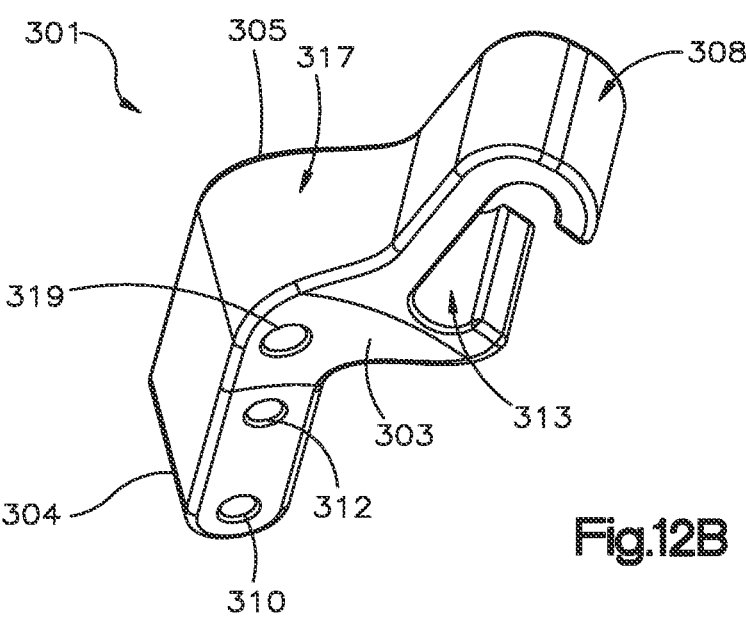
FIG. 12B is another perspective view of the guide body of FIG. 11A.
Figure 12C:
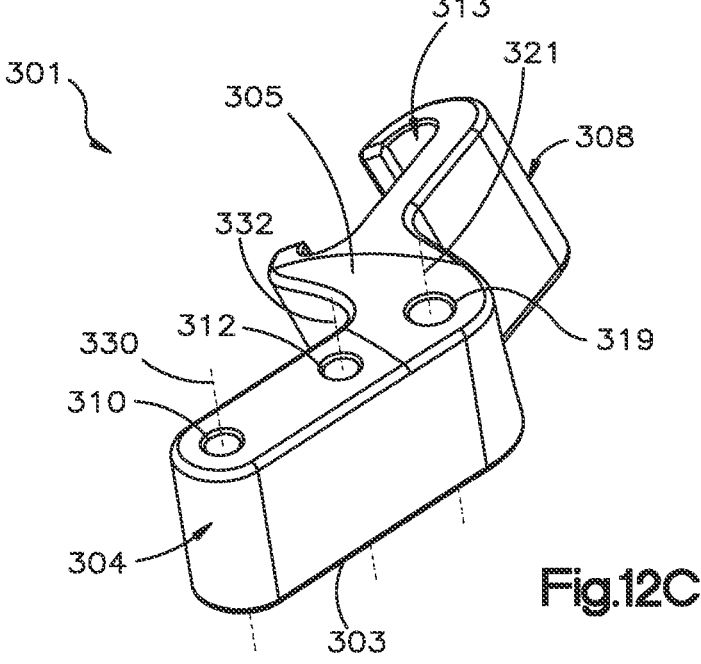
FIG. 12C is another perspective view of the guide body of FIG. 11A.
Figure 12D:
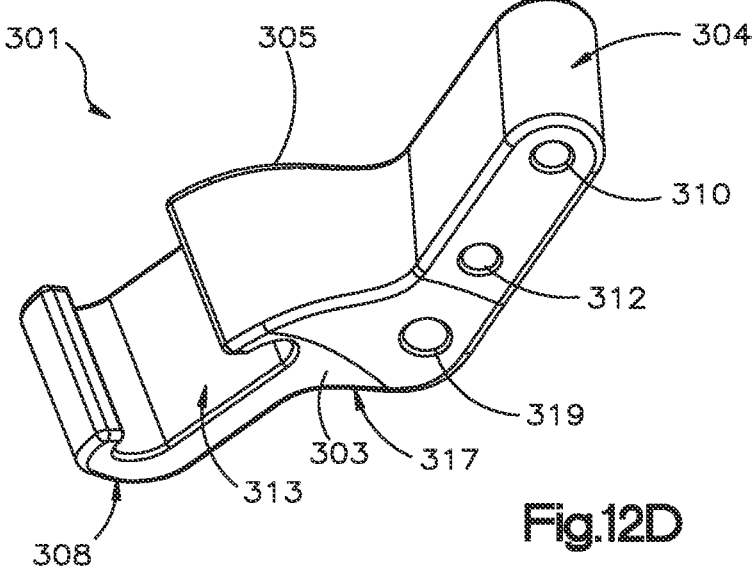
FIG. 12D is another perspective view of the guide body of FIG. 11A.
Figures 12E, 12F:
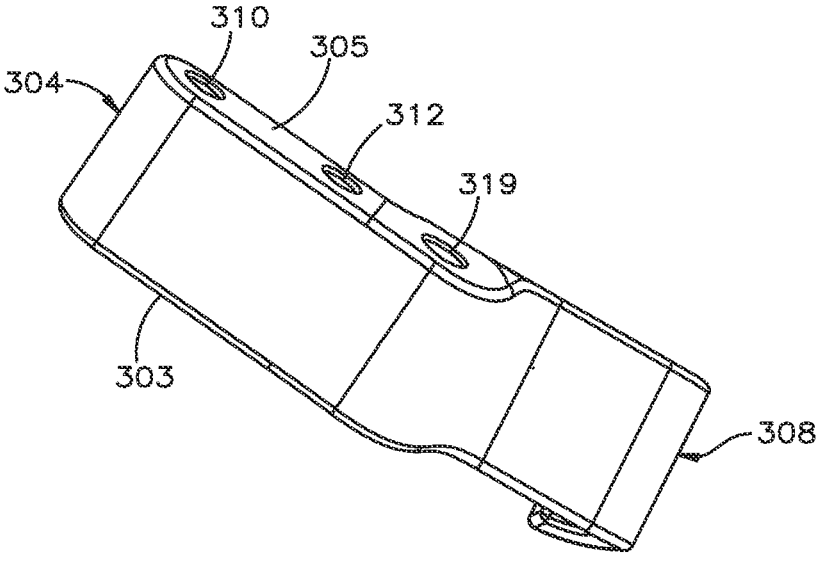
FIG. 12E is a side elevation view of the guide body of FIG. 11A.
FIG. 12F is another side elevation view of the guide body of FIG. 11A.
Figures 12G, 12H:
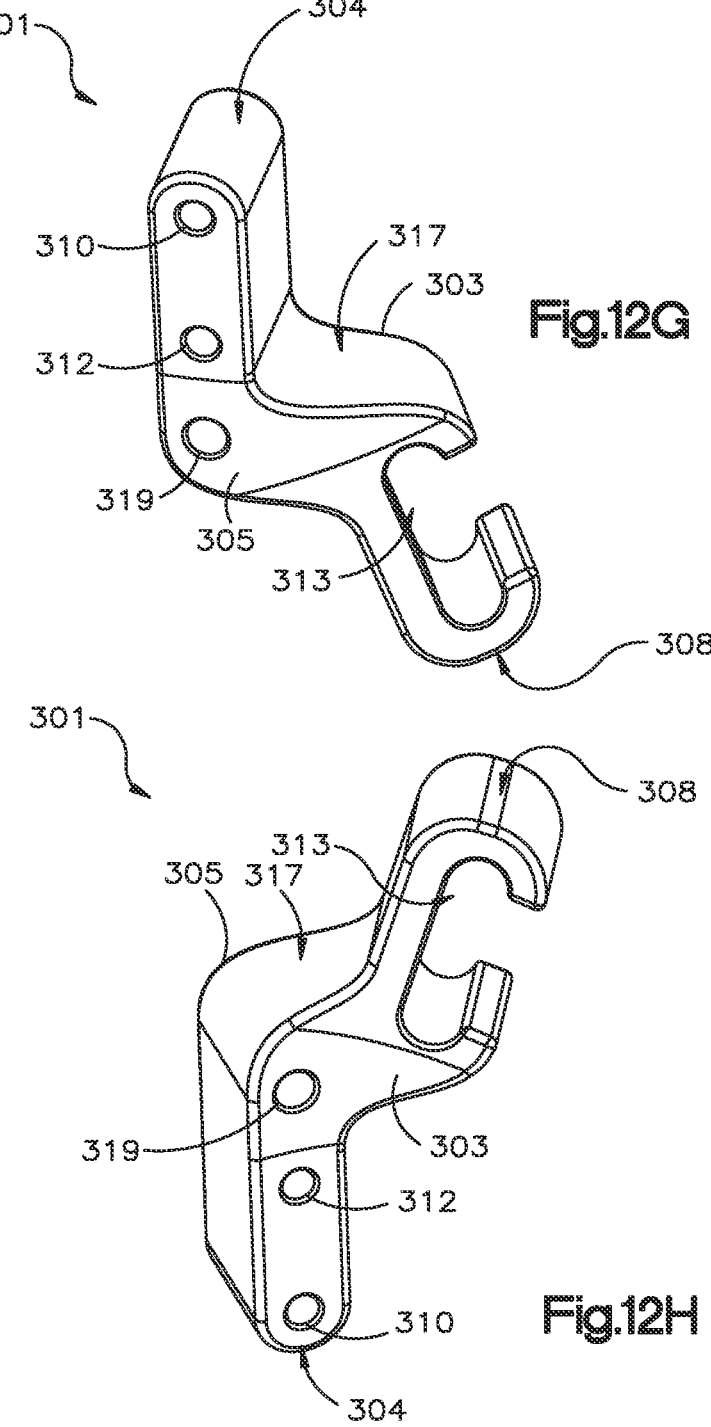
FIG. 12G is a top plan view of the guide body of FIG. 11A.
FIG. 12H is a bottom plan view of the guide body of FIG. 11A.
Figures 12I, 12J:
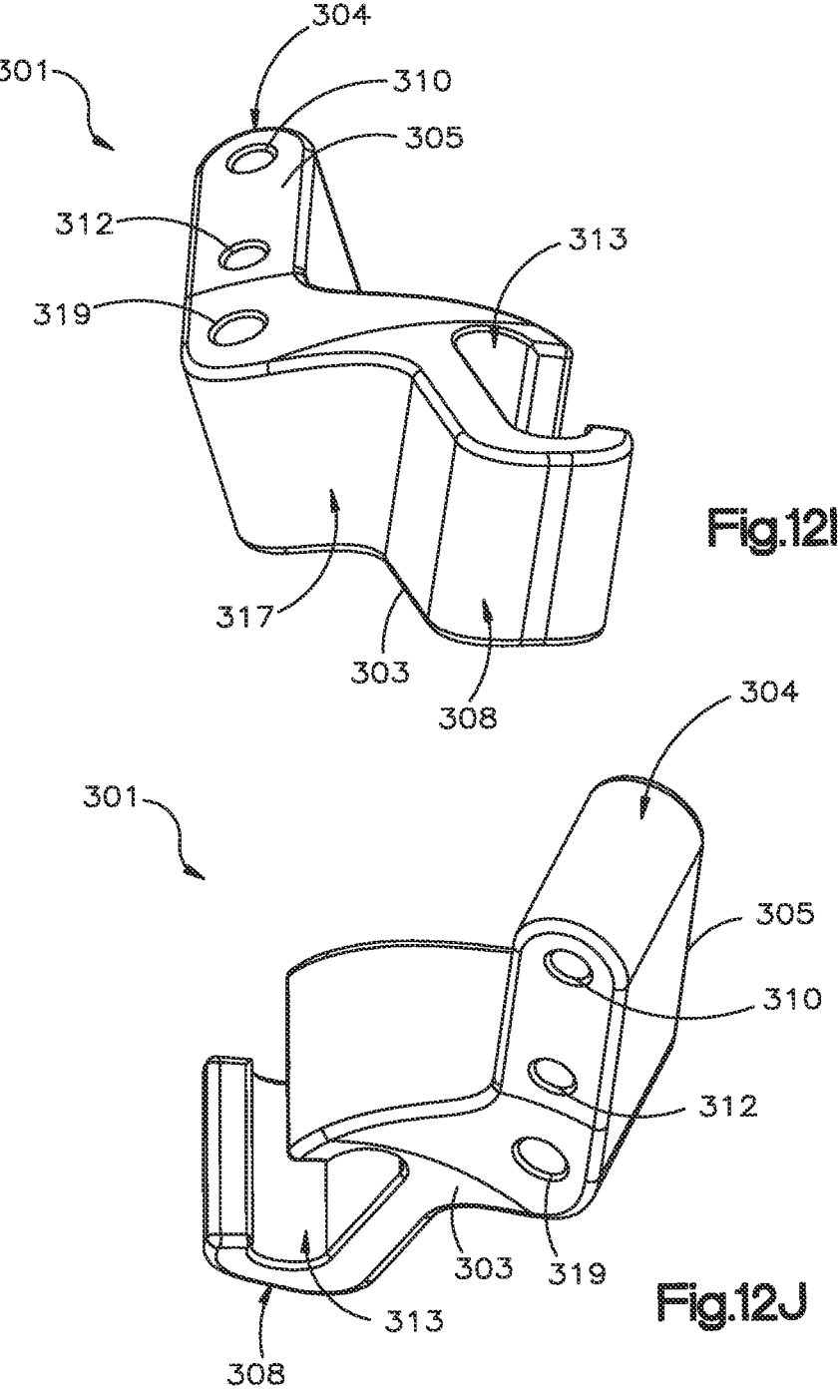
FIG. 12I is a front elevation view of the guide body of FIG. 11A.
FIG. 12J is a rear elevation view of the guide body of FIG. 11A.

Referring also to FIGS. 11A-11B, the insert 311 can be inserted through the aperture 313 such that seat portion 370 sits atop the outer surface 305 of the guide body 301. The insert portion 368 can extend through the guide body 301 to the bone-facing surface 371 which can be offset with respect to the bone-facing surface 303 of the guide body 301 in the bone-facing direction. The insert portion 386 can have a height along the bone-facing direction that is greater than the height of the guide body 301 at the aperture 313. The height of the insert portion 386 can be measured from the shoulder 380 to the bone-facing surface 371 of the insert 311. The height of the guide body 301 can be measured from the outer surface 305 to the bone-facing surface 303 of the guide body 301. As will be described in more detail below, the height of the insert portion can be sized such that the bone-facing surface 371 at the insert portion 368 abuts the metatarsal 108 when the bone-facing surface 303 at the first end portion 304 abuts the cuneiform bone 104.

It should be appreciated that as described above with respect to the alignment guide 200, the alignment guide 300 can define the angle α between the central axis 330 of the first cannula 310 and the axis 236 of the fourth cannula 316 (see FIG. 5), the angle β between the axis 330 of the first cannula 310 and the axis 236 of the fourth cannula 316 (see FIG. 6), and the angle γ between the axis 330 of the first cannula 310 and the axis 236 of the fourth cannula 316 (see FIG. 7). It should further be appreciated that the system can include a plurality of inserts that define different values of at least one of the angles α, β, and γ as desired.

Referring again to FIGS. 12A-12J, the second or distal end portion 308 of the guide body 301 can be offset with respect to the first or proximal end portion 304 in the medial direction. In particular, the guide body 301 can include an intermediate portion 317 that extends from the first end portion 304 to the second end portion 308. In one example, the intermediate portion 317 extends from the distal end of the first end portion 304 to the proximal end of the second end portion 308. In one example, the first and second end portions 304 and 308 and the intermediate portion 317 can be monolithic with each other so as to define a one-piece unitary body. Alternatively, either or both of the first and second end portions 304 and 308 can be separate from the intermediate portion 317 and attached to the intermediate portion 317 in any suitable manner as desired.

The guide 300 can further include a joint alignment cannula 319 that extends through the guide body 301 at a location between the proximal cannulas and the aperture 313. The joint alignment cannula 319 is configured to receive a joint alignment member #that is configured to be driven into a joint 369 that is defined by medial cuneiform bone 104 and the first metatarsal 108 (see FIG. 14D), thereby aligning the alignment guide 300 with the body 301 with the joint 369, which can define a tarsometatarsal joint in some examples. The position of the joint alignment cannula 319 can set a spacing of the first end portion 304 of the guide body 301 relative to the medial cuneiform bone 104 and set a spacing of the second end portion 308 relative to the metatarsal 108 (see FIG. 14E).

In one example, the joint alignment cannula 319 can extend through the intermediate portion 317. Thus, the joint alignment cannula 319 can be disposed distal of the first and second cannulas 310 and 312. The joint alignment cannula 319 can extend from the outer surface 305 to the inner surface 303 along a respective central axis 321. In one example, the central axis 321 can lie on a common plane with the first and second central axes 330 and 332. The central axis 321 can be oriented parallel with the first and second central axes 330 and 332. Alternatively, the central axis 321 can be angularly offset with respect to the first and second central axes 330 and 332 within the common plane. The joint alignment cannula 319 can have a diameter that is different than the diameter of either or both of the first and second cannulas 310 and 312. For instance, the diameter of the joint alignment cannula 319 can be greater than the diameter of either or both of the first and second cannulas 310 and 312. Thus, a k-wire that fits through the joint alignment cannula 319 can be sized too big to fit through either of the first and second cannulas 310 and 312. Alternatively, the diameter of the joint alignment cannula 319 can be equal to the diameter of the first and second cannulas 310 and 312.

The first end portion 304 can define a position and orientation of a first set of cannula (e.g., cannulas 310 and 312). The second end portion 308 and the insert 311 can define a position and orientation of a second set of cannula (e.g., the third and fourth cannula 314 and 316). The first set of cannula and the second set of cannula can be offset from each other and/or angled with respect to each other as described herein.

Figure 14A:
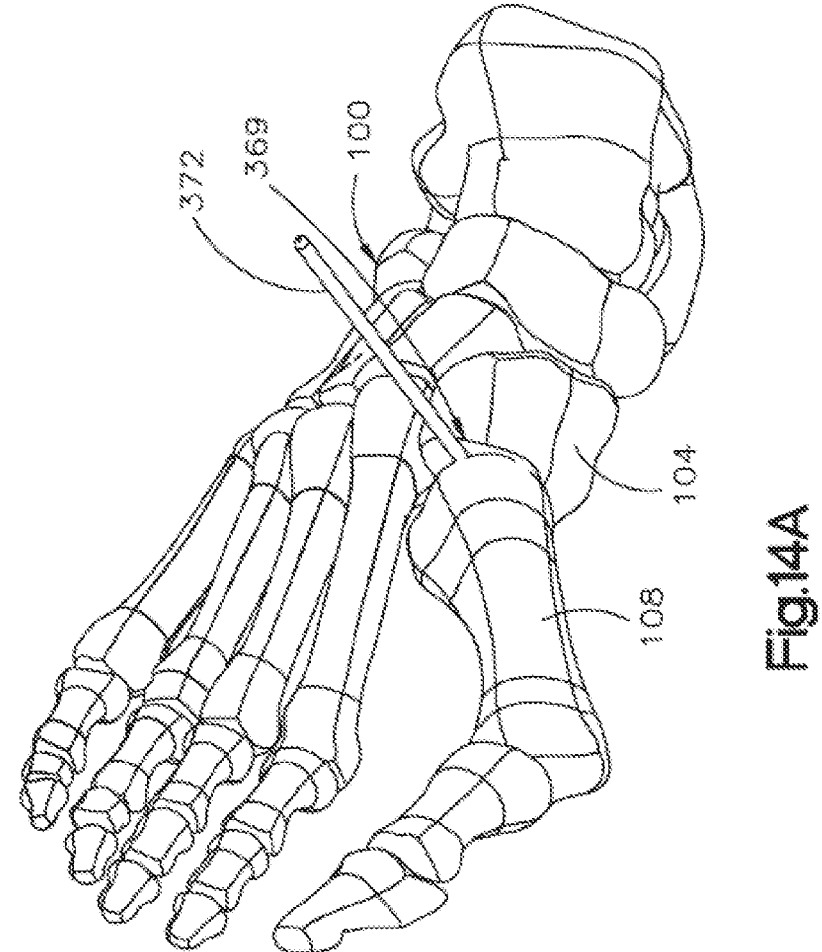
FIG. 14A is a perspective view showing insertion of a joint alignment member into a tarsometatarsal (TMT) joint.
Figure 14B:
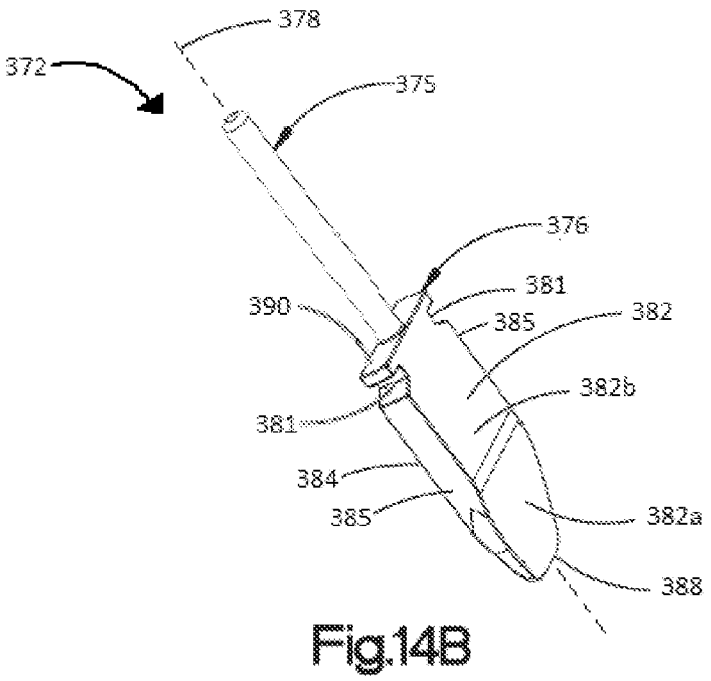
FIG. 14B is a perspective view of the joint alignment member of FIG. 14A.

During operation, referring to FIG. 14A-14B, a joint alignment member 372 can be inserted into a joint 369 that is defined by medial cuneiform bone 104 and the first metatarsal 108. The joint alignment member 372 can be configured as a joint paddle having a paddle portion 376 and a shaft 375 that extends out from the paddle portion 376 along a central axis 378 that can also define a central axis of the paddle portion 376. The joint alignment member 372 can be inserted into the joint 369 along a predetermined trajectory that is parallel to the joint 369. Thus, the joint alignment member 372 can be driven along a direction from the dorsal side to the plantar side, such that a central axis 378 of the joint alignment member 372 extends along a declination angle of the joint 369. The joint 369 can be referred to as the tarsometatarsal (TMT) joint. The trajectory along which the joint alignment member is inserted into the joint 369 can further be an inferior direction, or a combination of inferior and lateral directions. Thus, the shaft 375 can extend out from the paddle portion 376 in the superior direction alone or in combination with the medial direction. Any suitable imaging source, such as x-ray, can confirm that the joint alignment member 372 is parallel with the joint. If not, the joint alignment member 372 can be manipulated and repositioned, or removed and reinserted until it has been confirmed to be oriented parallel to the joint 369. As will be appreciated from the description below, the joint alignment member 372 can be configured to align the alignment guide 300 with the tarsometatarsal joint 369 between the medial cuneiform bone 104 and the metatarsal 108.

The shaft 375 and paddle portion 376 can be a single monolithic structure, or can be detachable from each other as desired. The paddle portion 276 can define first and second major surfaces 382 and 384 that are opposite each other along a first select direction that is perpendicular to the central axis 378. The central axis 378 can be angularly offset with respect to the central axes of the third and fourth k-wires with respect to a view from the frontal plane when the alignment guide 300 is installed over the shaft 375 and the k-wires 260 and 264 (see also FIG. 14E). The paddle portion 276 can further include first and second sides 385 that each extend from the first major surface 382 to the second major surface 384. The first and second sides 385 can be opposite each other along a second direction that is perpendicular to each of the first select direction and the central axis 378. The paddle portion 276 can be inserted into the joint 369 such that one of the major surfaces 382 faces the cuneiform bone 104, and the other of the major surfaces 382 and 384 faces the metatarsal bone 108. The joint alignment member 372 can be reversible, such that the paddle portion 376 can be inserted into the joint 369 in a first orientation or a second orientation. In the first orientation, the first major surface 382 faces the cuneiform bone 104 and the second major surface 384 faces the metatarsal 108. In the second orientation, the first major surface 382 faces the metatarsal 108, and the second major surface 384 faces the cuneiform bone 104. In other examples, the joint alignment member 372 can be keyed so as to be insertable into the joint 369 in only one of the first and second orientations, and not in the other of the first and second orientations.

The paddle portion 376 can define a leading end 388 with respect to insertion into the joint 369, and a trailing end 390 opposite the leading end 388. The leading end 388 can be spaced from the trailing end 390 in a leading direction along the central axis 378. The shaft 375 can extend out from the trailing end 390. The first major surface 382 can define a first leading portion 382a and a first trailing portion 382b. The first leading portion 382a can extend from the first trailing portion 382b in the leading direction. Similarly, the second major surface 384 can define a second leading portion 384a and a second trailing portion 384b. The second leading portion 384a can extend from the second trailing portion 384b in the leading direction. At least respective portions up to respective entireties of the first leading portion 382a and the second leading portion 384a can be tapered toward each other as they extend in the leading direction to the leading end 388. The taper can assist with insertion of the paddle portion 376 into the joint 369. The paddle portion 376 can further include first and second notches 381 that extend into the sides 385 inwardly along the second select direction toward the central axis 378.

The first and second trailing portions 382*b* and 384*b* can be oriented substantially parallel to each other. Further, the first and second trailing portions 382*b* and 384*b* can be spaced from each other along the first select direction any suitable distance between from approximately 1 mm to approximately 4 mm, such as from approximately 2 mm to approximately 3 mm. In one example, the distance can be approximately 2.5 mm. Thus, the paddle portion 376 can keep the joint 369 in tension when the paddle portion 376 is inserted into the joint 369. In particular, one of the first and second trailing portions 382*b* and 384*b* can face and bear against the cuneiform bone 104, and the other of the first and second trailing portions 382*b* and 384*b* can face and bear against the metatarsal 108.

Figure 14C:
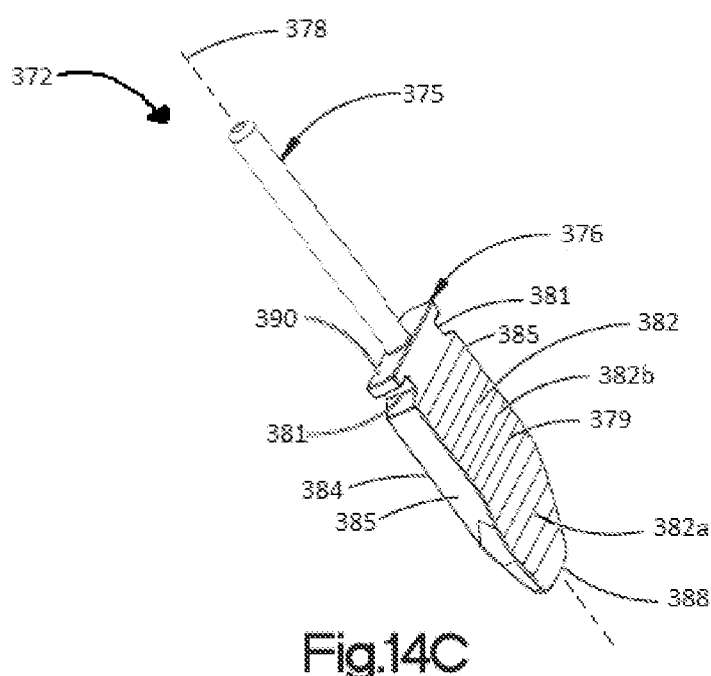
FIG. 14C is a perspective view of a joint alignment member constructed in accordance with another example.

In one example, the first and second major surfaces 382 and 384 can be smooth and untextured. Further, each of the first and second leading portions 382*a* and 384*a* and each of the first and second trailing portions 282*b* and 284*b* can be planar or alternatively shaped as desired. The paddle portion 376 can be inserted smoothly into the joint 369. Referring now to FIG. 14C, in another example, the paddle portion 376 can include one or more cutting teeth 379, such as a plurality of cutting teeth 379, or can otherwise have surface roughening. The cutting teeth 379 or surface roughening can be defined by either or both of the first leading portion 382*a* and the first trailing portion 382*b*. The cutting teeth 379 can further be defined by either or both of the second leading portion 384*a* and the second trailing portion 384*b*. Thus, the cutting teeth 379 can be disposed at respective portions of the first and second major surfaces 382 and 384 that contact the medial cuneiform 104 and the metatarsal bone 108 when the paddle portion 376 is inserted into the joint 376. The cutting teeth 379 can have any shape and size as desired. For instance, the cutting teeth 379 can be oriented along the second select direction. The cutting teeth 379 can be parallel to each other or angularly offset from each other as desired.

During operation, the joint alignment member 372 is driven distally such that the leading end 388 is inserted into the joint 369. The joint alignment member 372, and in particular the leading end 388 can be inserted into the joint 369 by translating the joint alignment member 372 distally without undergoing rotation. As the first and second major surfaces 382 and 384 are inserted into the joint 369, the cutting teeth 379, if present, cut into either or both of the distal end of the medial cuneiform 104 and the proximal end of the first metatarsal 108 that define the joint 369. It should be appreciated that once the joint alignment member 372 has been inserted into the joint 369, the paddle portion 376 maintains the joint 369 in tension. Thus, the distal end of the medial cuneiform bone 104 and the proximal end of the first metatarsal 108 apply a compressive retention force onto the joint alignment member 372, and in particular onto the paddle portion 376, that retains the joint alignment member 372 in the joint 369 along the desired predetermined trajectory.

Figure 14D:
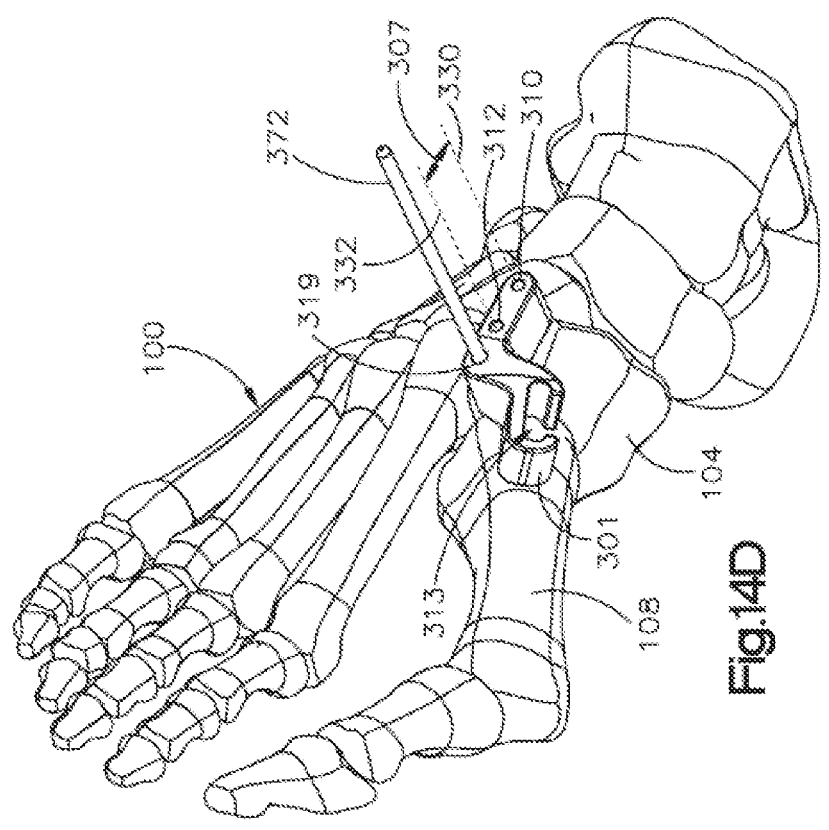
FIG. 14D is a perspective view showing insertion of a guide body illustrated in FIG. 11A onto the joint alignment member shown in FIG. 14A.

Next, referring to FIG. 14D, the alignment guide 300 can be placed adjacent the joint alignment member 372 such that the joint alignment cannula 319 is aligned with the shaft 375. The alignment guide 300 is then brought toward the patient's foot 100, which causes the shaft 375 to be inserted into the joint alignment cannula 319. Otherwise stated, the joint alignment cannula 319 can be driven over the joint alignment member shaft 375 as the alignment guide 300 is brought toward the patient's foot. The first and second cannulas 310 and 312 have a predetermined spacing with respect to the joint alignment cannula 319, Accordingly, when the joint alignment member 372 is disposed in the joint

369, the first and second cannulas 310 and 312 are aligned with the medial cuneiform bone 104, and the insert-receiving aperture 313 is aligned with the first metatarsal 108.

Figure 14E:
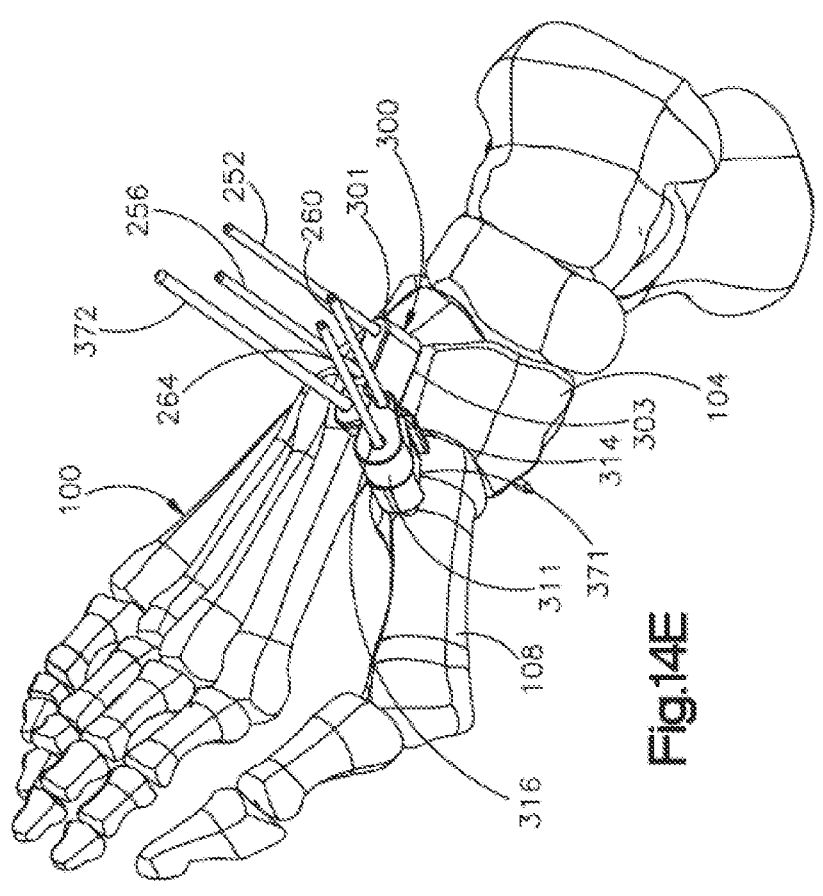
FIG. 14E is a perspective view showing the insert of FIG. 11A inserted into the guide body of FIG. 14D, and k-wires driven through the alignment guide and into the patient's foot.

Next, referring to FIGS. 14D-14E, the insert 311 can be received in the aperture in the manner described above. The alignment guide 300 can be positioned such that the first and second cannulas 310 and 312 are aligned with the medial cuneiform bone 104, and the third and fourth cannulas 314 and 316 are aligned with the first metatarsal 108. The alignment guide 300 can be placed against the patient's foot 100 such that the bone-facing surface 303 of the guide body 301 is disposed adjacent to or abuts the medial cuneiform bone 104, and the bone-facing surface 371 of the insert 311 is disposed adjacent to or abuts the first metatarsal 108. A plurality of temporary fixation elements such as k-wires 250 can be extended through respective cannula of the alignment guide 300 and into the patient's foot 100. In particular, at least one of the k-wires can extend through a respective cannula of the alignment guide 300 and into the respective medial cuneiform 104, and at least another of the k-wires can extend through a respective cannula of the alignment guide 300 and the first metatarsal bone 108.

At least one proximal temporary fixation device, such as at least one proximal k-wire, can be inserted through the at least one proximal cannula of the alignment guide 300 and into the medial cuneiform bone 104. For instance, a first k-wire 252 can be driven through the first cannula 310 and into the medial cuneiform 104. The first cannula 310 can be sized to guide the first k-wire 252 along the first central axis 330 as it is driven into the medial cuneiform bone 104. A second k-wire 256 can be driven through the cannula 312 and into the medial cuneiform bone 104. The second cannula 312 can be sized to guide the second k-wire 256 along the second central axis 332 as it is driven into the medial cuneiform bone 104. The first and second k-wires 354 and 356 can be referred to as first and second proximal k-wires respectively. The second cannula 312 and the second k-wire 256 can be disposed distal of the first cannula 310 and the first k-wire 252. The first and second k-wires 252 and 256 can be referred to as proximal k-wires.

At least one distal temporary fixation device, such as at least one distal k-wire, can be inserted through the at least one distal cannula of the alignment guide 300 and into the metatarsal 108. For instance, a third k-wire 260 can be driven through the third cannula 314 and into the first metatarsal 108. The third cannula 314 can be sized to guide the third k-wire 260 along the third central axis 334 (see FIG. 13A) as it is driven into the first metatarsal 108. A fourth k-wire 264 can be inserted through the fourth cannula 316 and into the first metatarsal 108. The fourth cannula 316 can be sized to guide the fourth k-wire 264 along the fourth central axis 336 (see FIG. 13A) as it is driven into the first metatarsal 108. The fourth cannula 316 and the fourth k-wire 264 can be disposed distal of the third cannula 314 and the third k-wire 260. The third and fourth k-wires 260 and 264 can be referred to as first and second distal k-wires respectively that are disposed distal of the proximal k-wires. The first and second k-wires 252 and 256 can be on opposite sides of the joint 369 with respect to the third and fourth k-wires 260 and 264.

The alignment guide 300 can be positioned such that the first and second cannulas 310 and 312 and the third and fourth cannulas 314 and 316, and thus the first and second k-wires 252 and 256 and the third and fourth k-wire 260 and 264, extend superiorly from the medial cuneiform bone 104 and the first metatarsal 108, respectively. Alternatively, the alignment guide 300 can be positioned such that the first and second cannulas 310 and 312 and the third and fourth cannulas 314 and 316, and thus the first and second k-wires 252 and 256 and the third and fourth k-wire 260 and 264, extend medially from the medial cuneiform bone 104 and the first metatarsal 108, respectively.

The first and second k-wires 252 and 256 can be oriented parallel with each other, as defined by their trajectories along the respective first and second central axes 330 and 332. Similarly, the third and fourth k-wires 260 and 264 can be oriented parallel with each other, as defined by their trajectories along the respective third and fourth central axes 334 and 336. Each of the k-wires 350 can be driven into the respective medial cuneiform bone 104 or the first metatarsal bone 108 at respective insertion points that can be predetermined on the patient's foot.

Figure 14F:
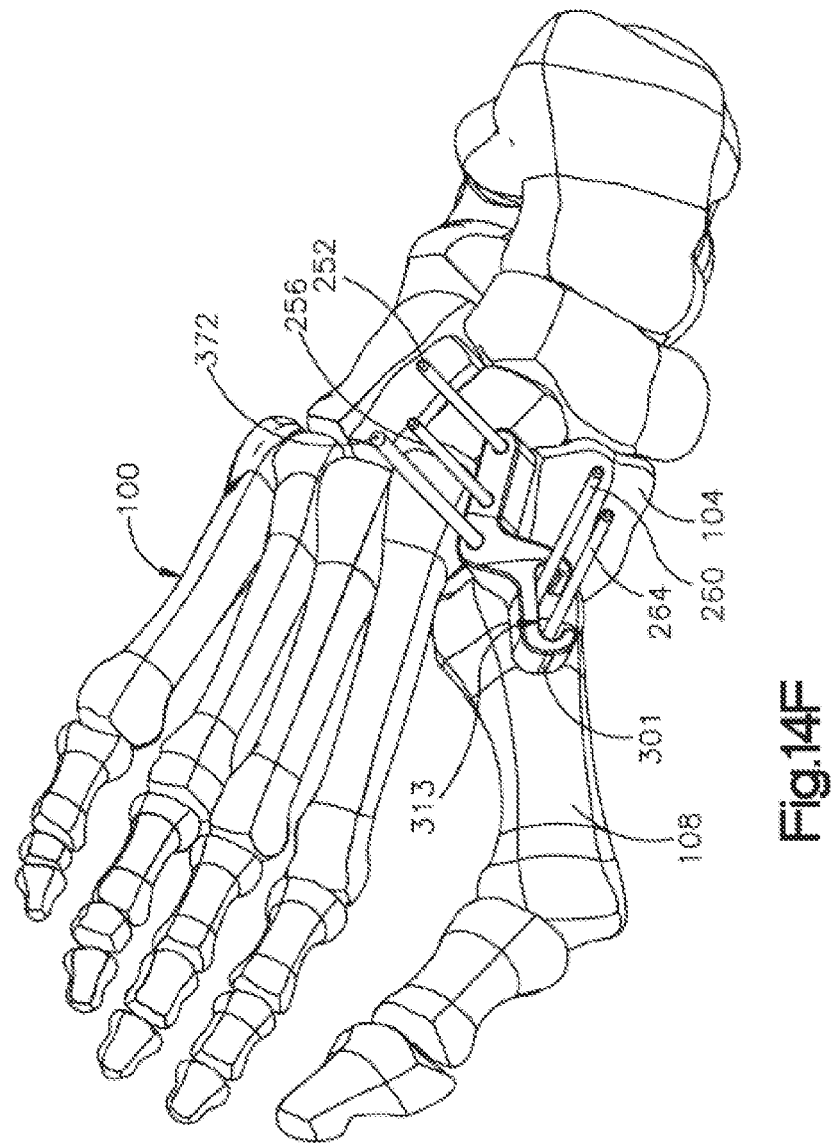
FIG. 14F is a perspective view showing the insert removed from the guide body.
Figure 14G:
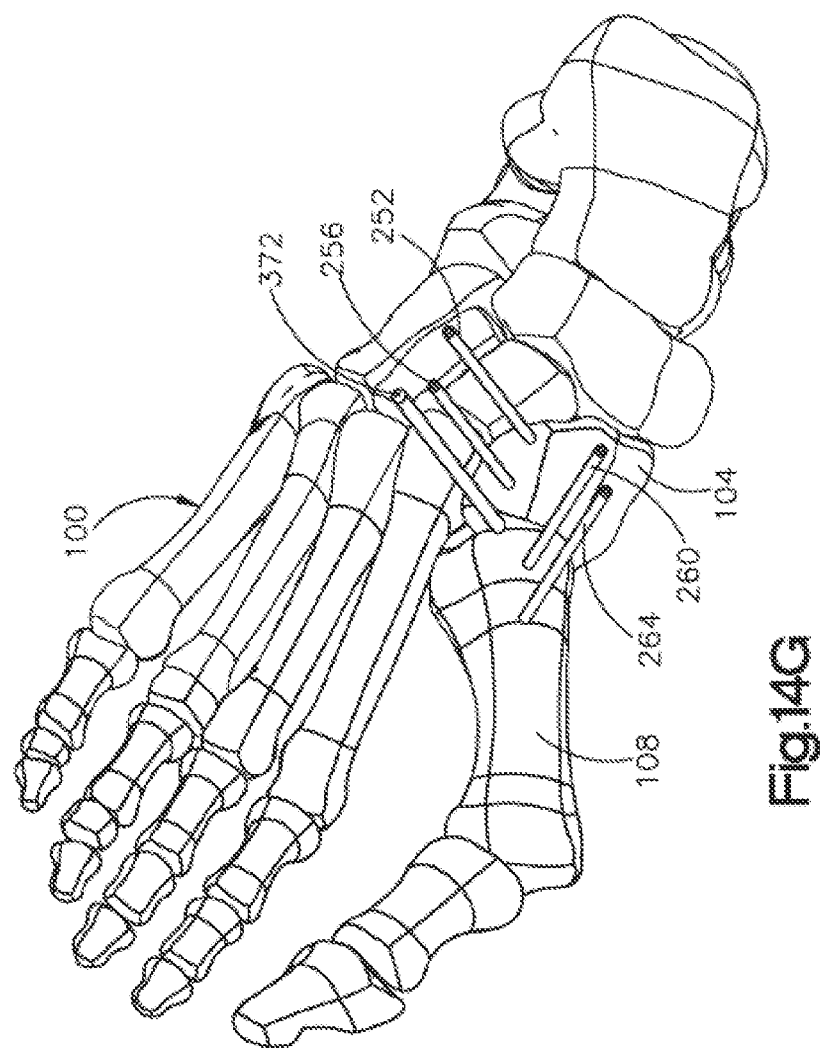
FIG. 14G is a perspective view of the guide body removed from the patient's foot.

Referring now to FIGS. 14F-14G, once the k-wires 252, 256, 260, and 264 have been driven into the patient's foot, the alignment guide 300 can be removed. First, as shown at FIG. 14F, the insert 311 can be removed from the third and fourth k-wires 260 and 264 by moving the insert 311 away from the guide body, and thus away from the patient's foot 100, along the k-wires 260 and 264 until the k-wires 260 and 264 have been removed from the insert 311. Next, as shown at FIG. 14G, the guide body 301 can then be removed from the k-wires 252, 256, 260, and 264 by moving the guide body 301 away from the patient's foot 100. It should be appreciated that once the insert 311 is removed, the third and fourth k-wires 260 and 264 extend through the aperture 313, such that clearance exists between the guide body 301 and the third and fourth k-wires 260 and 264. In this regard, it is recognized that the first and second central axes 330 and 332 of the first and second k-wires 252 and 256 are angularly offset from the third and fourth central axes 334 and 336 of the third and fourth k-wires 260 and 264. The guide body 301 is removed from the first and second cannulas 310 and 312 along the respective first and second central axes 330 and 332, and aperture 313 provides the clearance that allows the second end portion 308 to be removed from the third and fourth k-wires 260 and 264. In some examples the third and fourth k-wires can extend out the opening 315 during removal of the guide body 301 from the patient's foot. It should be appreciated that the joint alignment member 372 can be removed from the joint 369 after the proximal and distal k-wires have been driven into the patent's foot 100. The joint alignment member 372 can be removed from the joint 369 before or after removal of the alignment guide 300.

Figure 15A:
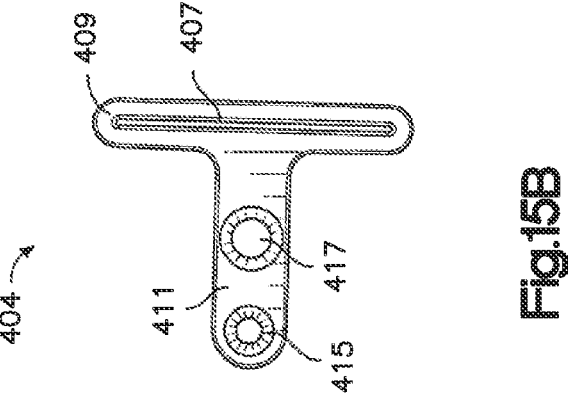
FIG. 15A shows a perspective view of a resection guide.
Figure 15B:
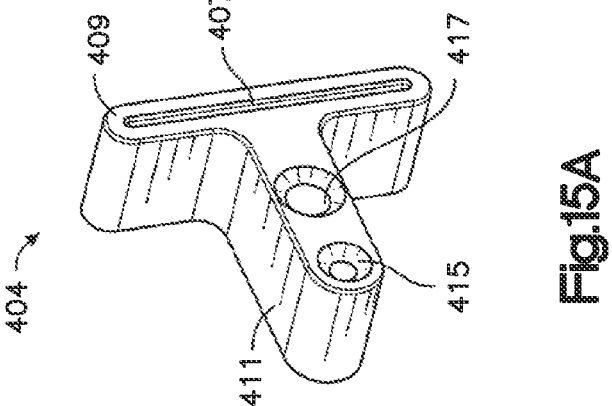
FIG. 15B shows a front view of the resection guide.

Referring now to FIGS. 15A-15B, once the alignment guide 200 or 300 has been removed, the patient's foot 100 can be aligned. In particular, the system for correcting alignment in the patient's foot 100 can include a resection guide 404. The resection guide 404 can align a resecting tool (not shown), such as a saw, a broach, or the like, with an end of the medial cuneiform bone 104 and/or an end of the metatarsal bone 108, respectively.

The resection guide 404 can include a cannulated portion 411. The cannulated portion 411 can include one or more apertures 415, 417. The resection guide 404 can include a plane portion 409. The plane portion can include a slot 407 for aligning the resecting tool. The apertures 415, 417 can interact with one or more k-wires (e.g., k-wires 250) or pins to align the plane portion 409 with the desired target location for the resection tool.

The plane portion 409 (e.g., a plane defining the slot 407) can be generally perpendicular with the cannulated portion 411 (e.g., an axis between the apertures 415, 417). In other implementations, the plane portion 409 can be angled with respect to the cannulated portion 411.

The apertures 415, 417 can extend through the cannulated portion 411. The apertures 415, 417 can be sized to align with the k-wires or pins. The slot 407 can extend through the plane portion 409. The slot 407 can have a height and thickness sized to accommodate the cutting portion of the resection tool. The slot 407 can have a depth sufficient to maintain alignment of the resection tool with the desired target location.

Depending on a planned corrected configuration of the first cuneiform bone 104 with the metatarsal 108, it may be necessary to remove material from one or both inner ends of the cuneiform bone 104 and the metatarsal 108. The angle between the cuneiform bone 104 and the metatarsal 108 can be adjusted in the corrected configuration. The lengths of one or both of the cuneiform bone 104 and the metatarsal 108 can also be adjusted in the corrected configuration. Each of these adjustments can contribute to the correction of the deformity in the patient's foot 100.

Figure 16A:
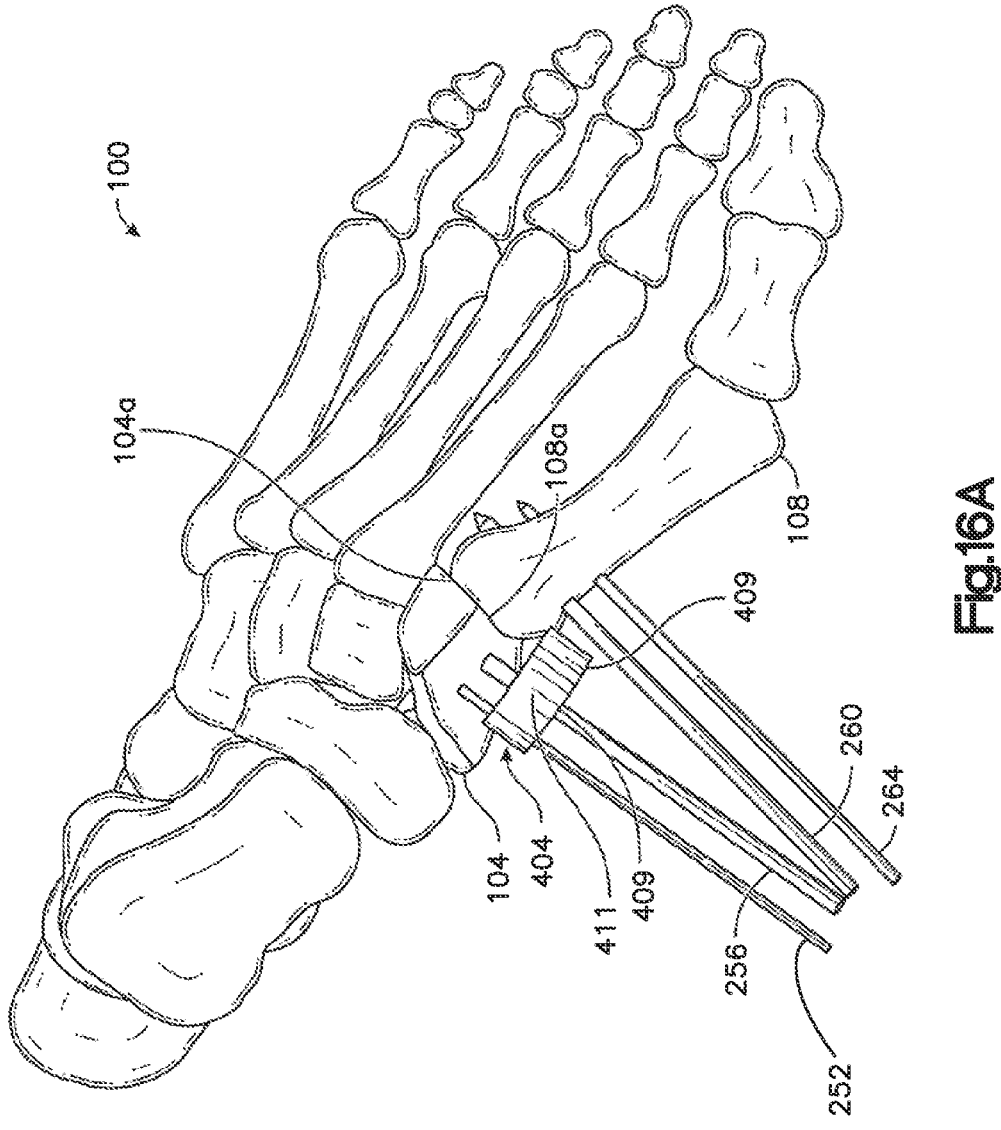
FIG. 16A shows the alignment guide removed.
Figure 16B:
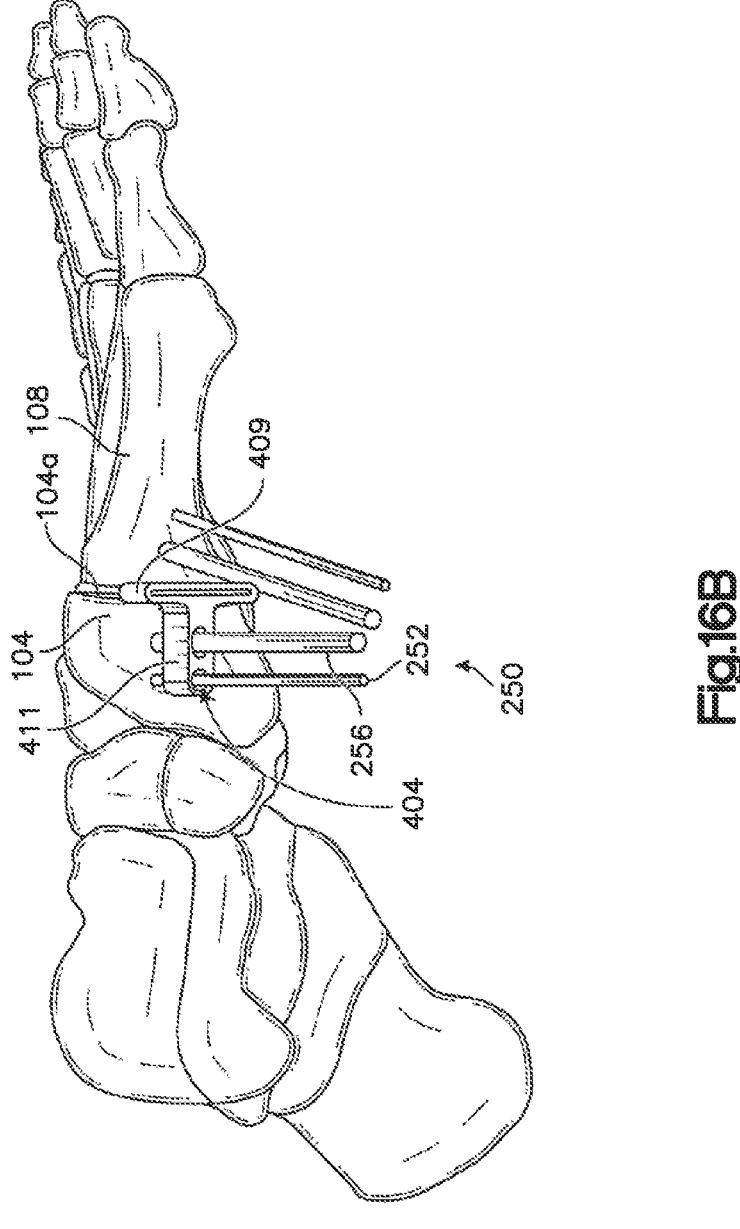
FIG. 16B shows installation of a first resection guide.

Accordingly, FIGS. 16A-16B show usage of the first resection guide 404 to align a resection tool with a first inner end of the first cuneiform bone 104. The cannulated portion 411 can be received over the first and second k-wire 252, 256 on the apertures 415, 417, respectively. This can align the plane portion (e.g., the slot 407) with the end of the first cuneiform bone 104. A resection plane 104a can be cut into the first cuneiform bone 104 using a resecting tool through the slot 407. The resection plane 104a can be aligned with the first and second k-wire 252, 256.

Figure 17:
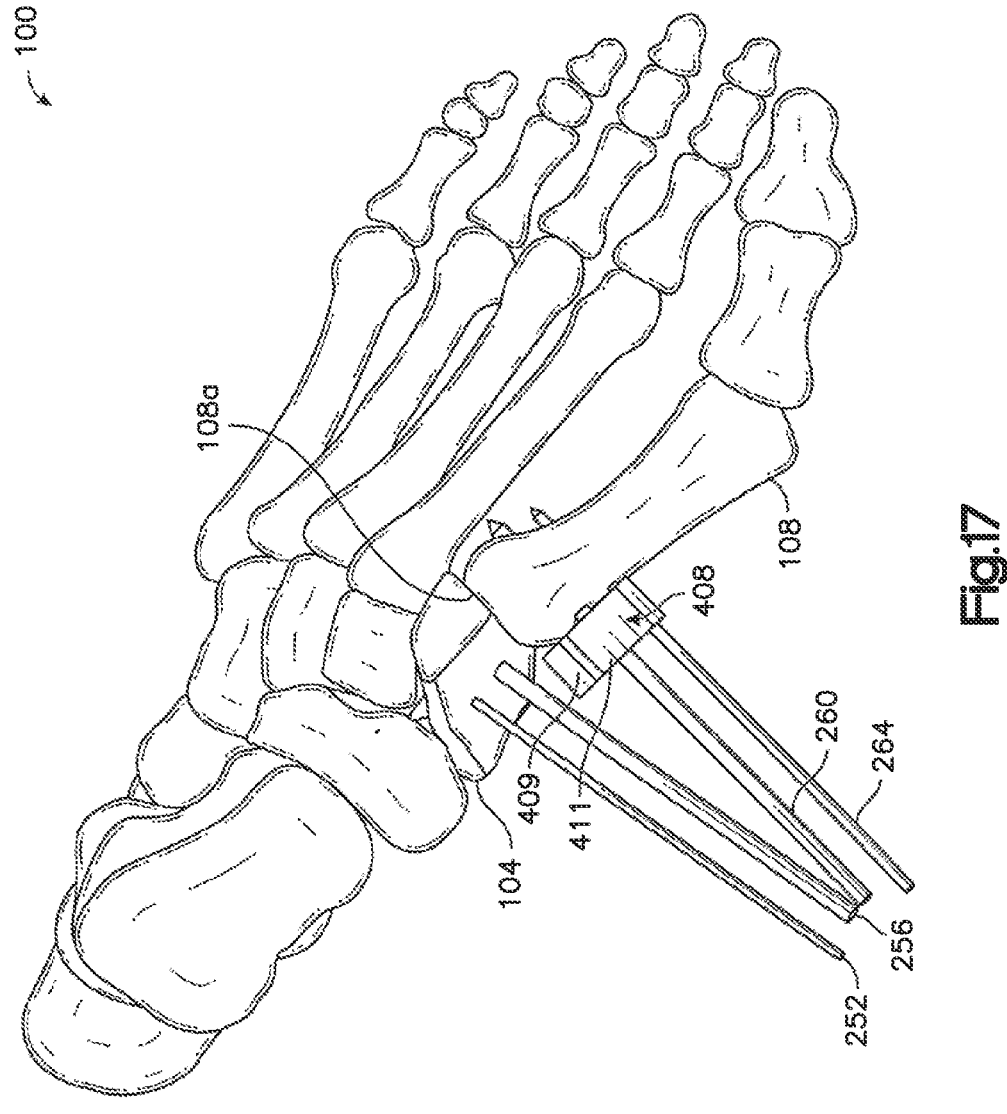
FIG. 17 shows the installation of a second resection guide.

FIG. 17 shows usage of a second resection guide 408 to align a resection tool with a first inner end of the metatarsal bone 108. The second resection guide 408 can include the same components as the resection guide 404 (e.g., a plane portion 409 and a cannulated portion 411).

The cannulated portion 411 of the second resection guide 408 can be received over the third and fourth k-wires 260, 264 on apertures 415, 417, respectively. The third and fourth k-wires can align the plane portion 409 and a slot 407 with the end of the metatarsal bone 108. A resection plane 108a can be cut into the metatarsal bone 108 using a resecting tool through the slot 407. The resection plane 108a can be aligned with the third and fourth k-wires 260, 264. In some implementations, the resection guide 404 can be used to form the resection plane 108a instead of the section resection guide 408.

Figures 18A, 18B, 18C:
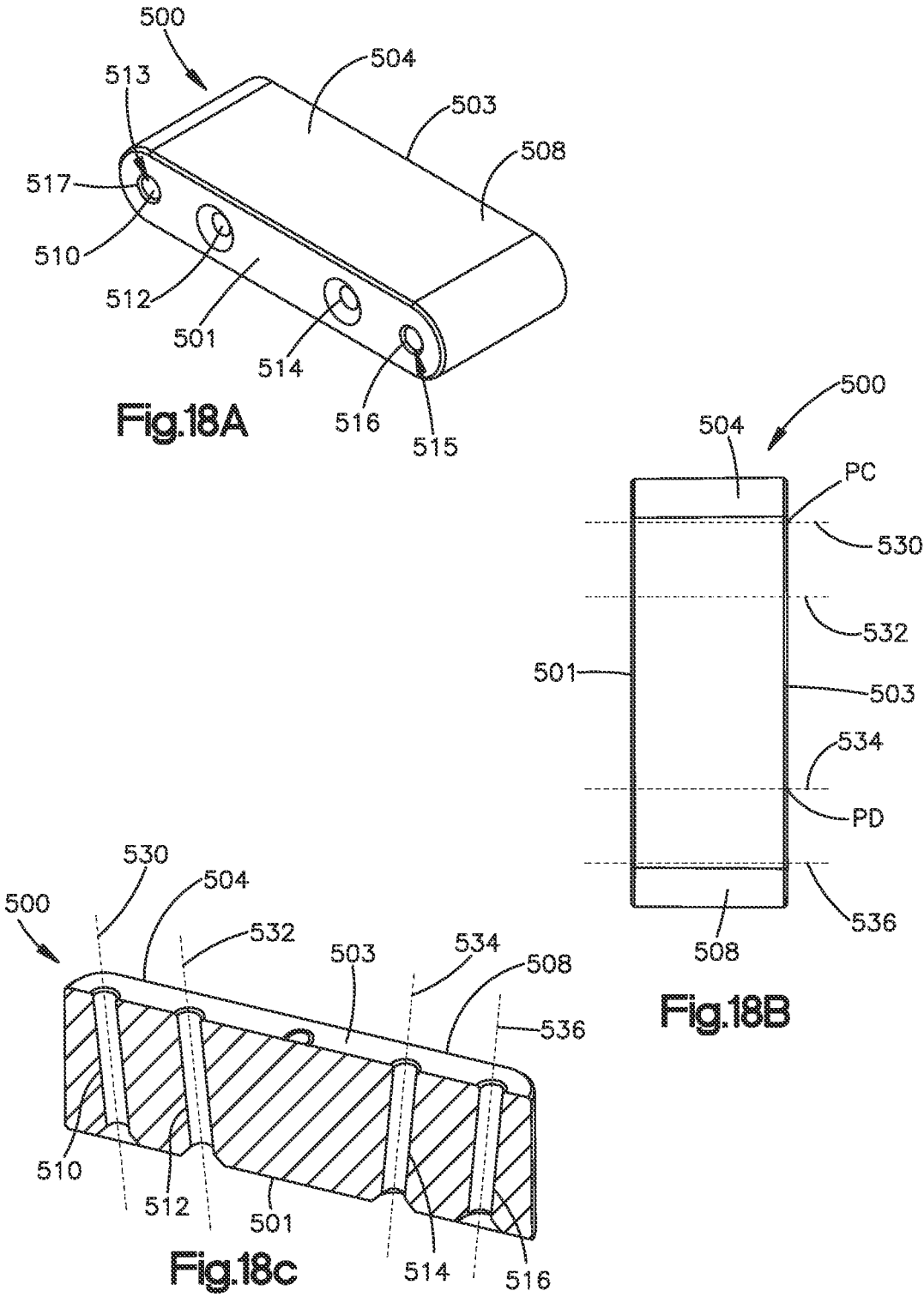
FIG. 18A shows a perspective view of the correction guide.
FIG. 18B shows a top view of the correction guide.
FIG. 18C is a cross-sectional view of a correction guide in another example.
Figure 19A:
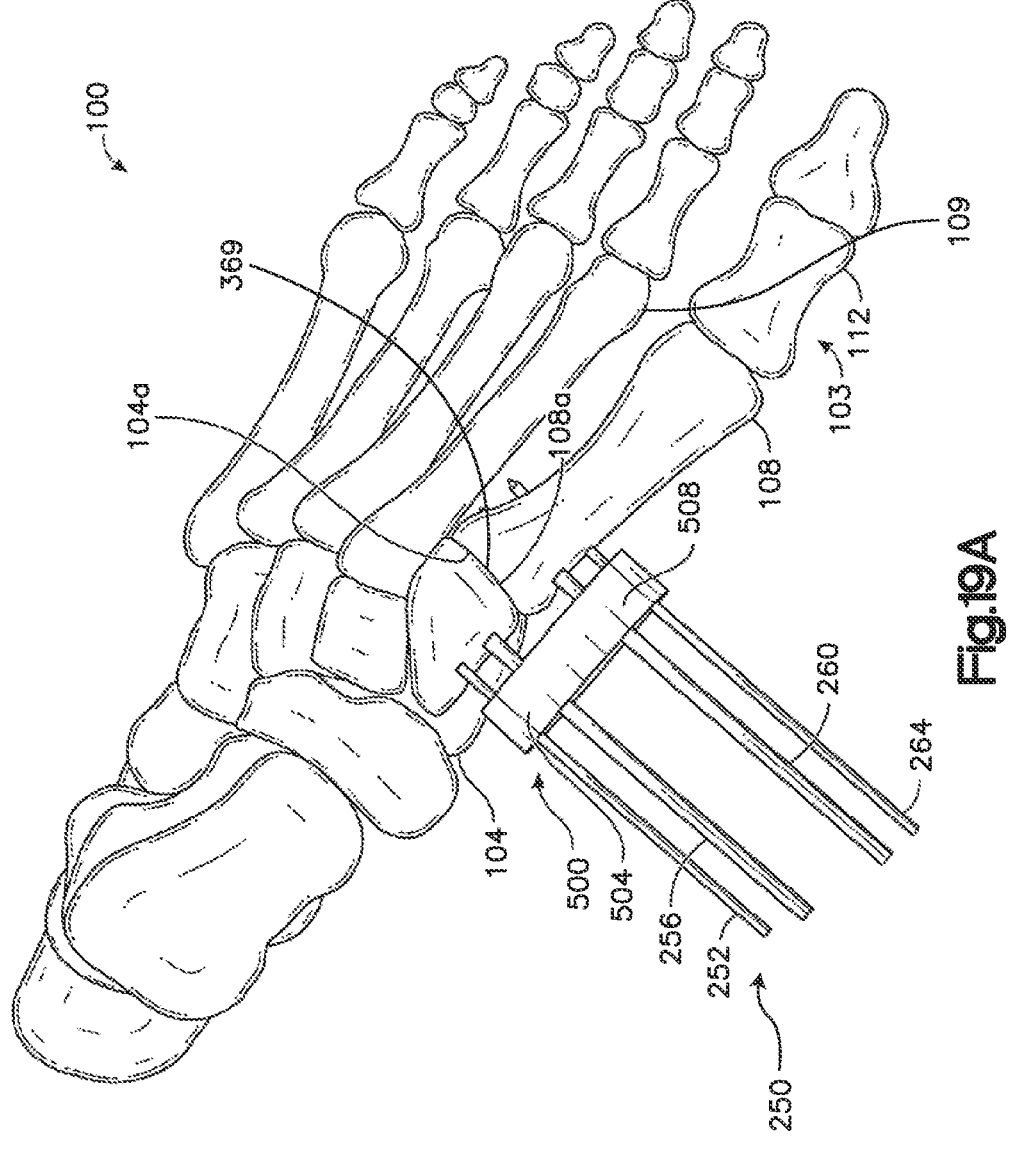
FIG. 19A shows a correction guide assembled over the plurality of k-wires to align the medial cuneiform bone and the metatarsal bone of the patient's foot into a corrected configuration.
Figure 19B:
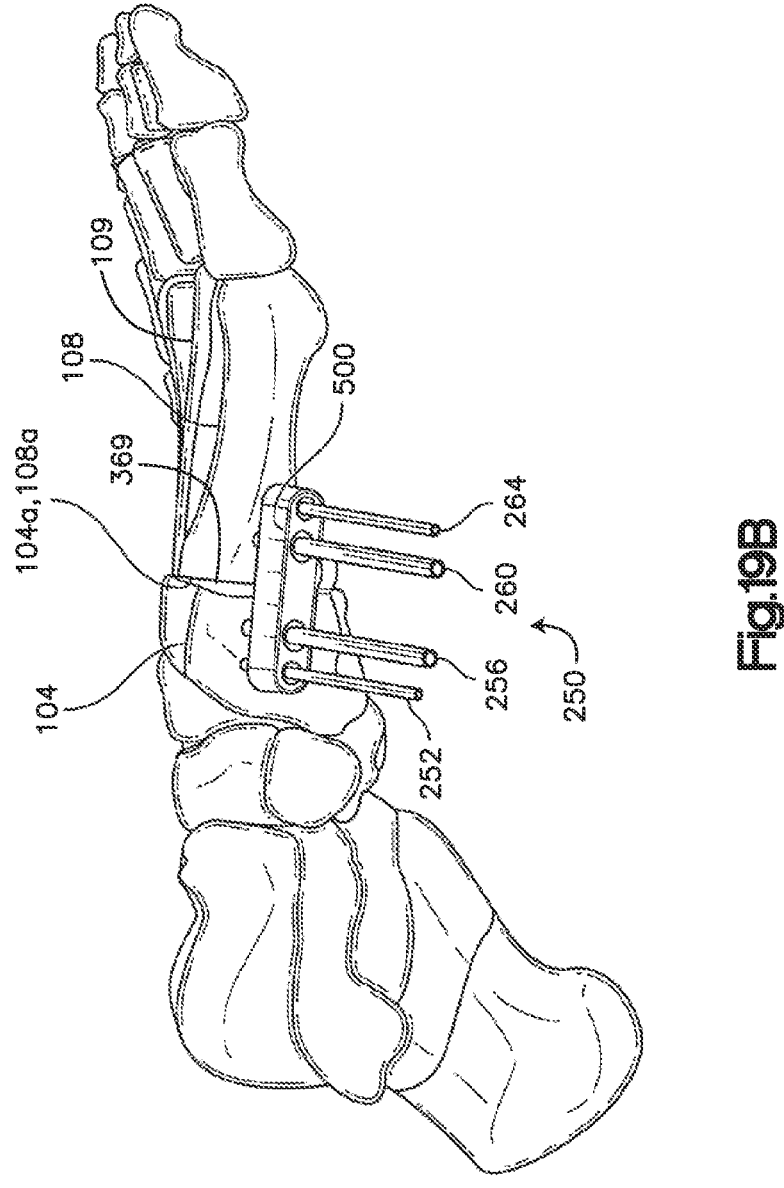
FIG. 19B is another view showing the correction guide of FIG. 19A assembled over the plurality of k-wires to align the medial cuneiform bone and the metatarsal bone of the patient's foot into a corrected configuration.

As shown in FIGS. 18A-18B, the system for correcting alignment in the patient's foot 100 can include a correction guide 500. The correction guide 500 can align the bones in the patient's foot 100 from the initial or deformed configuration into a corrected configuration 103 that is different than the initial or deformed configuration, as shown in FIGS. 19A-19B, and reduces the deformity that is defined by the first metatarsal 108. In particular, the correction guide can cause the first metatarsal 108 to move from the initial configuration to the corrected configuration by rotating the first metatarsal 108 relative to the medial cuneiform 108 and/or translating the first metatarsal 108 relative to an adjacent second metatarsal 109. The correction guide 500 can define an inner bone-facing surface 501 and an opposite outer surface 503. The correction guide 500 can include a first end portion 504. The correction guide 500 can include at least one proximal cannula 513 such as first and second cannulas 510 and 512 that extend through the correction guide 500, and in particular through the first end portion 504. The first and second cannulas 510 and 512 can correspond to the first and second k-wires 252 and 256, respectively, which have been previously driven at least into or through the medial cuneiform bone 104. The first and second cannulas 510 and 512 can extend along respective first and second central axes 530 and 532, respectively. The first and second central axes 530 and 532 can be parallel to each other, or can alternatively be oriented at any suitable angle relative to each other as desired.

The correction guide 500 can include a second end portion 508 that extends distally with respect to the first end portion 504. The inner and outer surfaces 501 and 503 can be defined by the first end portion 504 and the second end portion 508. In one example, the first and portion 504 and the second end portion 508 can define a single monolithic unitary structure. Thus, the first and second end portions 504 and 508 can be positionally fixed with respect to each other. The first end portion 504 can be referred to as a proximal end portion, and the second end portion 508 can be referred to as a distal end portion. The correction guide 500 can include at least one distal cannula 515 such as third and fourth cannulas 514 and 516 that extend through the correction guide 500, and in particular through the second end portion 508. The third and fourth cannulas 514 and 516 can correspond to the third and fourth k-wires 260 and 264, respectively, which have been previously driven at least into or through the metatarsal bone 108. The third and fourth cannulas 514 and 516 can extend along respective third and fourth central axes 534 and 536, respectively. The third and fourth central axes 534 and 536 can be parallel to each other, or can alternatively be oriented at any suitable angle relative to each other as desired.

The first and second cannulas 510 and 512 can be referred to as proximal cannulas 513 of the correction guide 500, and the third and fourth cannulas 514 and 516 can be referred to as distal cannulas 515 of the correction guide that are spaced distally from the proximal cannulas 513. The proximal k-wires 251 are configured to be driven into cuneiform bone 104 in the manner described above, and inserted into respective ones of the proximal cannulas 513. The distal k-wires 253 are configured to be driven into the metatarsal 108 in the manner described above, and inserted into respective ones of the distal cannulas 515. While the system can include two proximal k-wires 251 and two distal k-wires 253 in one example, it should be appreciated that the system can include any number of proximal and distal k-wires including at least one. Thus, at least one proximal k-wire 251 can be inserted through at least one proximal cannula 513 and into the cuneiform bone 104, and at least one distal k-wire 253 can be inserted through at least one distal cannula 515 and into the metatarsal 108.

The proximal and distal cannulas 513 and 515, respectively, extend through the correction guide from the outer surface 503 to the inner surface 501. The first cannula 510 can extend through the outer surface 503, such that the first central axis 530 extend through a point PC. The point PC can have a position (x, y, z) in the Cartesian coordinate plane. Similarly, the fourth cannula 516 can extend through the outer surface 503, such that the fourth central axis 536 extend through a point PD that has a respective position (x, y, z) in the Cartesian coordinate plane. The points PC and PD can define a relative position of the first and fourth central axes 530 and 536 in the Cartesian coordinate system.

As shown in FIGS. 19A-19B, the correction guide 500 can be received on the k-wires 250. The at least one proximal k-wire 251 can be received within a respective at least one proximal cannula 513, and the at least one distal k-wire 253 can be received within a respective at least one distal cannula 513. The at least one proximal and distal k-wires 251 and 253 can be positioned in the cannulas of the correction guide 500 after having been driven into either of the alignment guides 200 and 300 and after subsequent removal of the alignment guide. It is recognized that the k-wires 251 and 253 extend medially from the medial cuneiform 104 and the first metatarsal 108 as shown in FIGS. 19A-19B. Alternatively, the k-wires 251 and 253 can extend superiorly from the medial cuneiform 104 and the first metatarsal 108 as described above.

The first and second central axes 530 and 532 can have a predetermined angular relationship with respect to the third and fourth central axes 534 and 536 from a view from the frontal plane. In one example shown at FIG. 18B, the predetermined angular relationship can be a parallel relationship, such that the first and second central axes 530 and 532 are oriented parallel with the third and fourth axis 534 and 536. Thus, the first and second central axes 530 and 532 can be aligned within the same plane as the third and fourth central axis 534 and 536. In other words, a common plane can include each of the first and second central axes 530 and 532 along with the third and fourth central axes 534 and 536. Alternatively, the first and second central axes 530 and 532 can be angularly offset with respect to the third and fourth central axes 534 and 536 with respect to a view from the frontal plane.

The correction guide 500 can align the metatarsal bone 108 relative to the medial cuneiform bone 104 as it is advances on the k-wires 250. In particular, the first and second proximal k-wires 252 and 256 are received by the first and second proximal cannulas 510 and 512, respectively, and the third and fourth distal k-wires 260 and 264 are received by the third and fourth distal cannulas 514 and 516, respectively. The first and second k-wires 252 and 256 can be oriented along the first and second central axes 530 and 532, respectively, and the third and fourth k-wires 260 and 264 can be oriented along the third and fourth central axes 534 and 536, respectively. The correction guide 500 thus causes the proximal k-wires to move to thereby assume the predetermined angular relationship with the distal k-wires. As the at least one distal k-wire moves relative to the at least one proximal k-wire, the at least one distal k-wire causes the first metatarsal 108 to correspondingly move with respect to the medial cuneiform bone 104 and the second metatarsal bone 109. Thus, the correction guide 500 can cause the distal k-wires to rotate in the frontal plane, which in turn causes the metatarsal 108 to rotate in the frontal plane with respect to the cuneiform bone 104 in a direction of rotation. The direction of rotation can be in the counterclockwise direction in the frontal plane (that is, from a view of the frontal plane in the proximal direction). The correction guide 500 can therefore orient the distal k-wires 260 and 264, and thus the metatarsal bone 108 and the proximal phalanx 112, into the corrected configuration 103. Re-orientation of the metatarsal 108 relative to the medial cuneiform bone 104 can include rotation and/or translation of the metatarsal 108 in the Cartesian coordinate system (e.g., in three orthogonal planes). The degree of rotation and/or translation of the metatarsal 108 can be determined based on the angles $\alpha$, $\beta$, and/or $\gamma$, and/or any differences in the relative positions of the axes between the alignment guide 200 and the correction guide 500 (e.g., any differences in the relative positions defined by points A, B and points C, D). In one example, the correction guide 500 can cause the at least one distal k-wire 253 to rotate in the frontal plane, for instance in a clockwise direction with respect to a view from the frontal plane. Thus, the metatarsal 108 similarly rotates in the clockwise direction in the frontal plane. Because the first and second central axes 530 and 532 can be oriented parallel with respect to the third and fourth central axes 534 and 536, the correction guide 500 does not compress or distract the TMT joint 369 as it receives the proximal and distal k-wires 251 and 253.

The corrected configuration 103 can include one or more corrections to the alignment of the bones of the patient's foot 100. For example, the metatarsal 108 can be generally aligned with the proximal phalanx 112 of the great toe. The corrected configuration 103 can reduce or eliminate the bunion and/or hallux valgus deformity. The resected face 104a of the medial cuneiform bone 104 can be abutted against the resected face 108a of the metatarsal bone 108. This abutment can promote the union or fusion of the metatarsal 108 with the medial cuneiform bone 104. Proper abutment can require translation of the metatarsal 108 relative to the medial cuneiform bone 104.

Referring now to FIG. 18C, in another example the predetermined angular relationship between the first and second axes 530 and 532 and the third and fourth central axes 534 and 536 can be an angular offset with respect to each other. For instance, the first and second central axes 530 and 532 can converge toward the third and fourth central axes 534 and 536 as they extend in a direction from the outer surface 503 to the inner surface 501. In particular, the first and second central axes 530 and 532 can converge toward the third and fourth central axes 534 and 536 can converge toward each other along a longitudinal direction that includes the distal direction and proximal direction that is opposite the distal direction. In one example, the first and second central axes 530 and 532 can be aligned with each other and with the third and fourth central axes 534 and 536, for instance along the distal direction. Thus, the first and second central axes 530 and 532 can be coplanar with the third and fourth central axes 534 and 536, such that a common plane includes each of the central axes 530, 532, 534, and 536. During use, the correction guide 500 can compress the TMT joint 369 as it receives the proximal and distal k-wires 251 and 253 and is driven toward the cuneiform bone 104 and the metatarsal 108. In this regard, the correction guide 500 can be configured for a combination of realignment and compression of the cuneiform bone 104 and the metatarsal 108, and thus can be referred to as a "realignment and compressor block" (e.g., a RAC block).

While the first and second k-wires 252, 256 can be received within the first and second cannula 510 and 512, respectively, on the first end 504 of the correction guide 500, and the third and fourth k-wires 260 and 264 can be received within the third and fourth cannula 514 and 516, respectively, on the second end 508 of the correction guide 500, it should be appreciated that any number of k-wires in the cuneiform bone 104 and the metatarsal bone 108 can be inserted through respective cannulas of the correction guide as desired.

Figure 20:
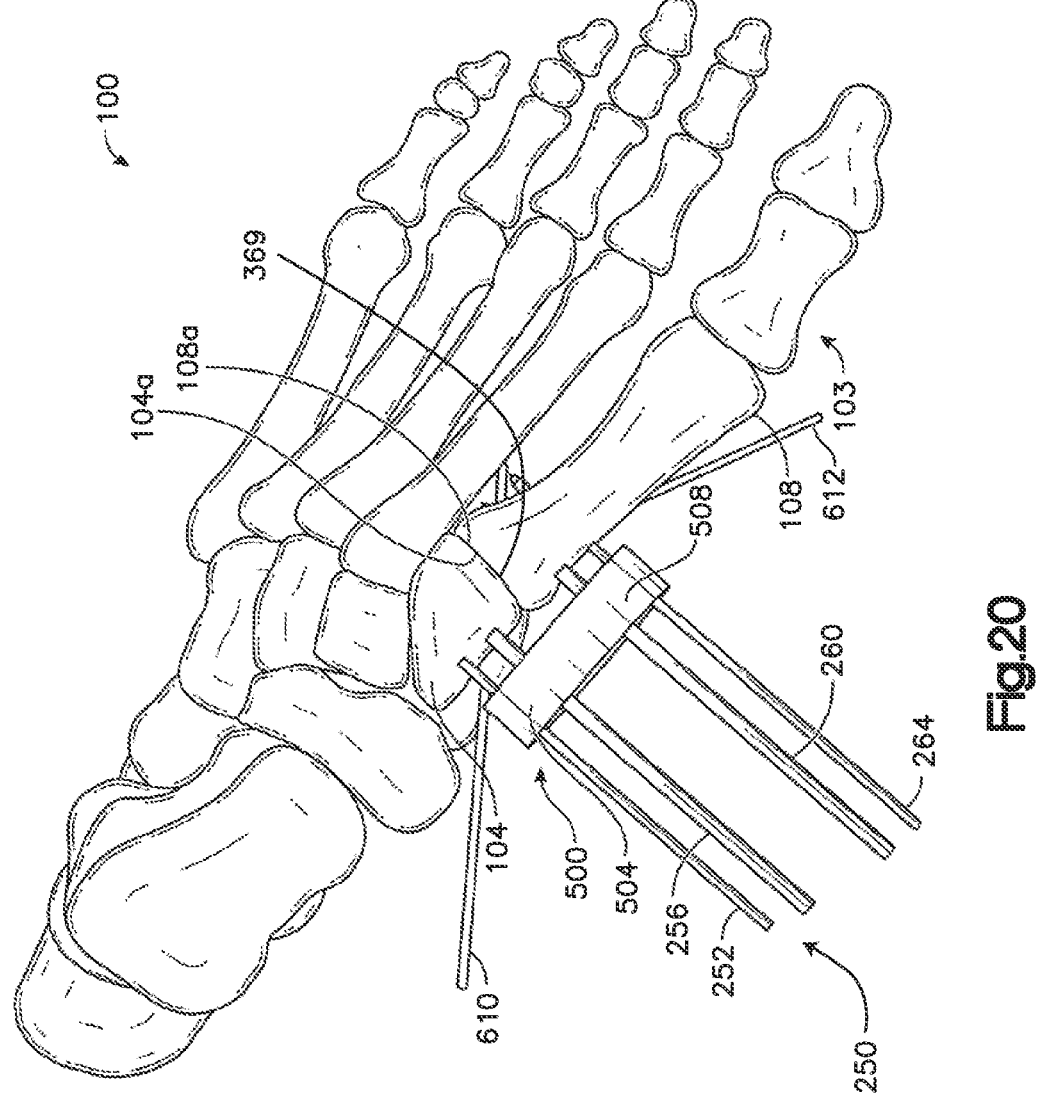
FIG. 20 shows the insertion of first and second fixing k-wires into the medial cuneiform bone and the metatarsal bone.

As shown in FIG. 20, the medial cuneiform bone 104 can be fixed temporarily or permanently relative to the metatarsal 108 in the corrected configuration 103. A first or proximal fixing k-wire 610 can be inserted into the medial cuneiform bone 104 and the metatarsal bone 108. The first fixing wire 610 can extend through the resection faces 104a, 108a. A second or distal fixing k-wire 612 can be inserted through the metatarsal 108 and into the medial cuneiform bone 104. The second fixing k-wire 612 can be inserted through the resection planes 104a, 108a. In other implementations, any temporary or permanent fixing means can be used for connecting the medial cuneiform bone 104 with the metatarsal bone 108 in the corrected configuration. For example, the medial cuneiform bone 104 and the metatarsal bone 108 can be screwed together, braced together, adhered together or otherwise connected together on a temporary or permanent basis.

Figure 21:
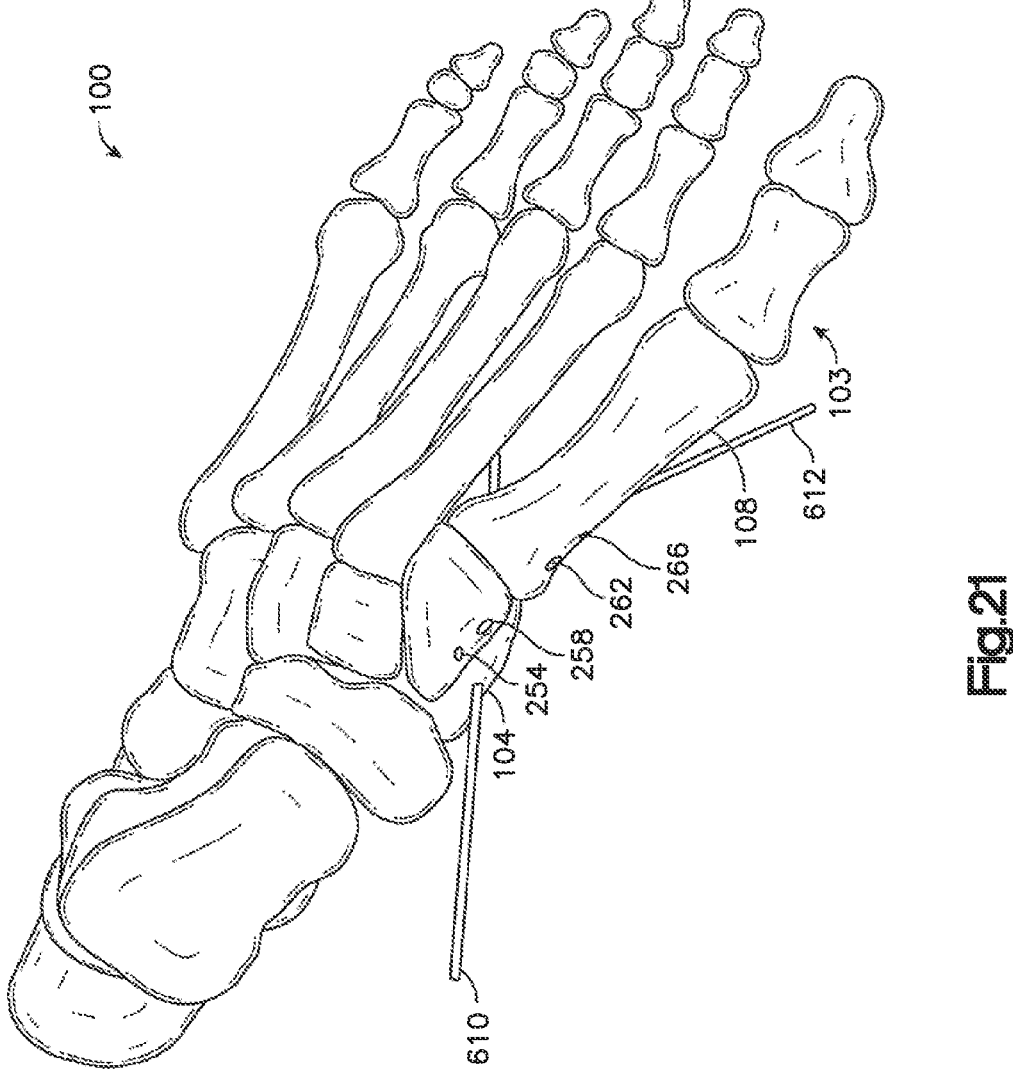
FIG. 21 shows the patient's foot with the plurality of k-wires removed.

As shown in FIG. 21, with the medial cuneiform bone 104 and the metatarsal bone 108 fixed in the corrected configuration 103, the correction guide 500 can be removed from the plurality of the k-wires 250. The plurality of k-wires 250 can be removed from the medial cuneiform bone 104 and/or the metatarsal bone 108.

Figure 22:
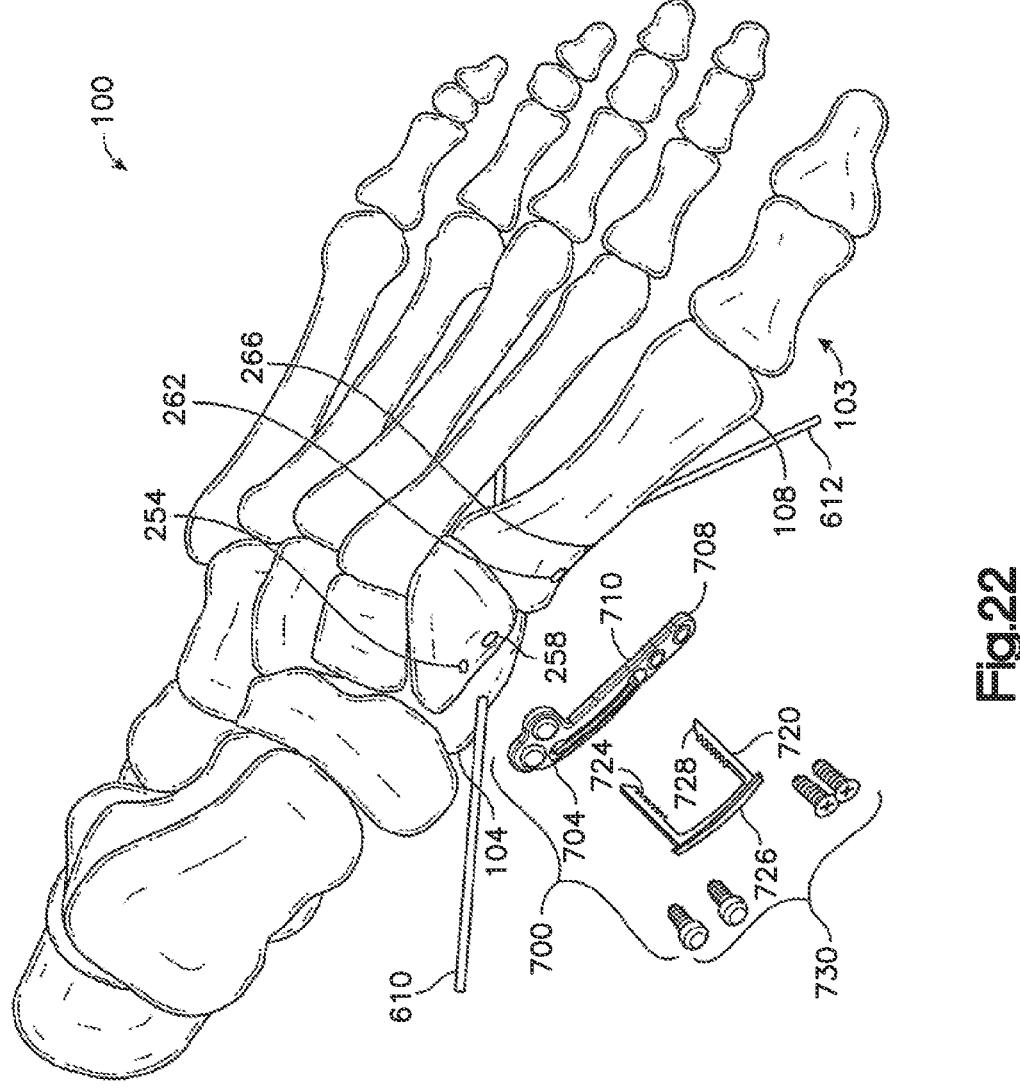
FIG. 22 shows an exploded view of a bone plate assembly aligned with the medial cuneiform bone and the metatarsal bone in the corrected configuration.
Figure 25:
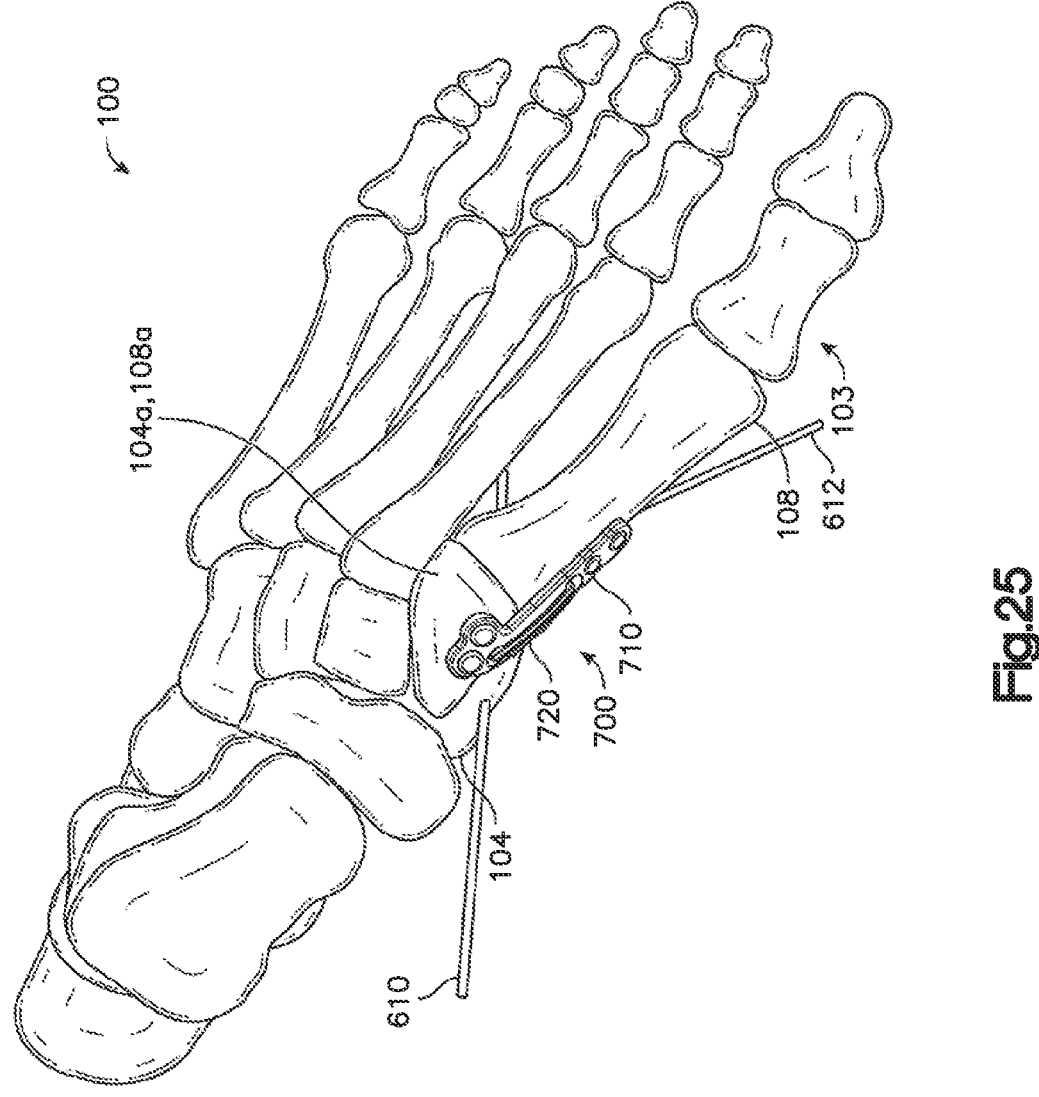
FIG. 25 shows the bone plate assembly assembled with the medial cuneiform bone and metatarsal bone in the corrected configuration.
Figure 26:
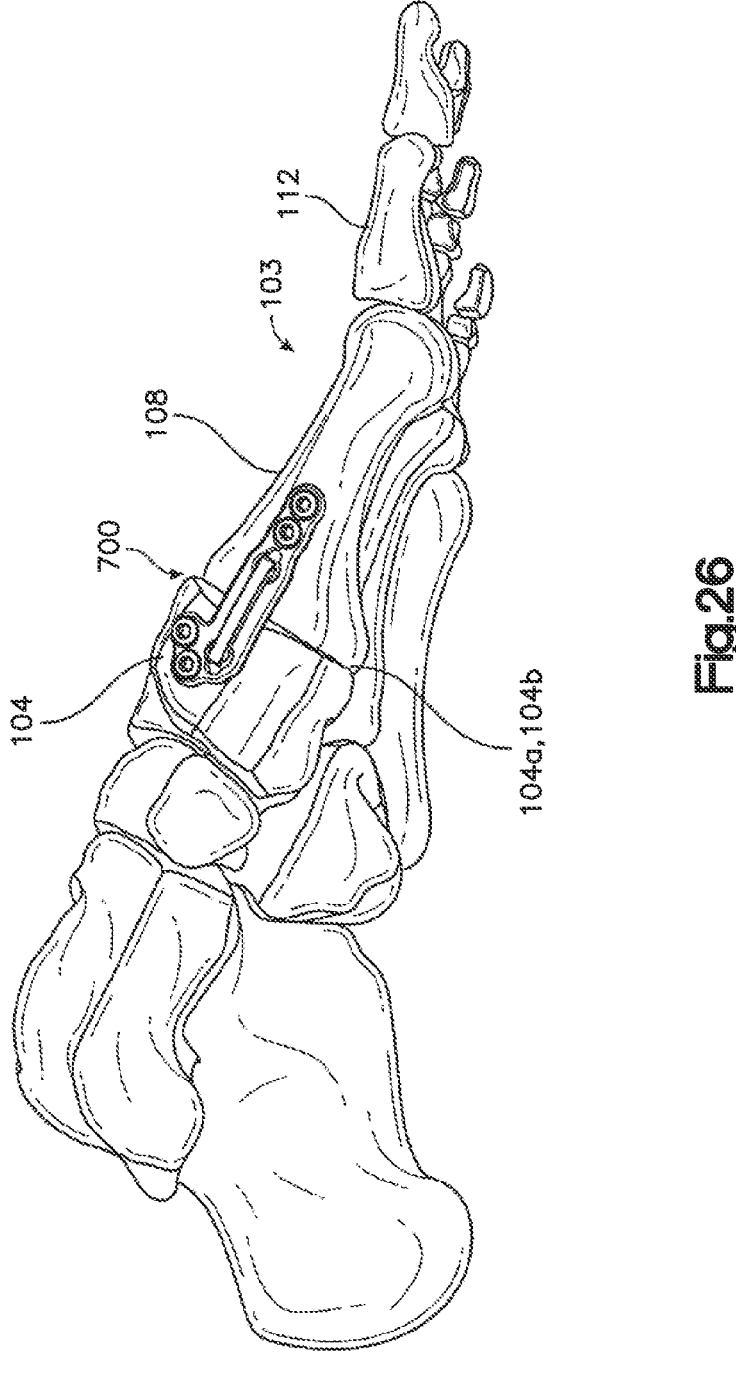
FIG. 26 shows a side view of the patient's foot in the corrected configuration.
Figure 28A:
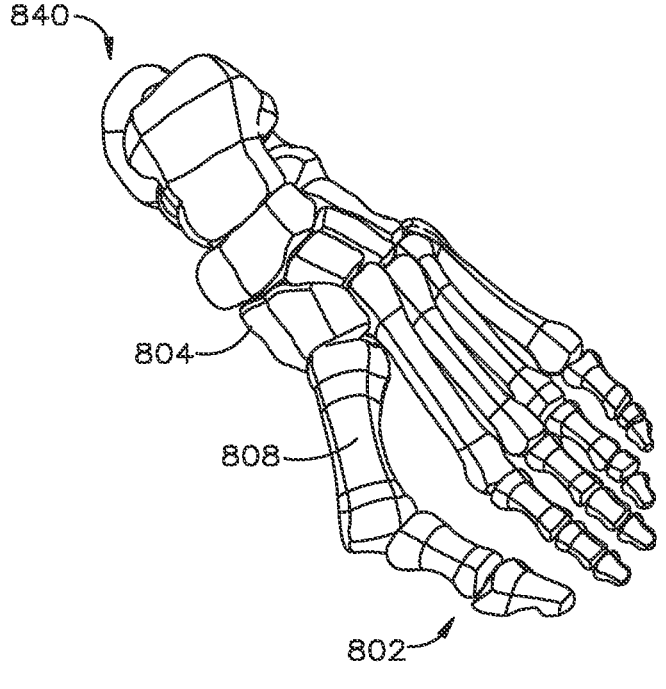
FIG. 28A shows the virtual model in a virtual deformed configuration.
Figure 28B:
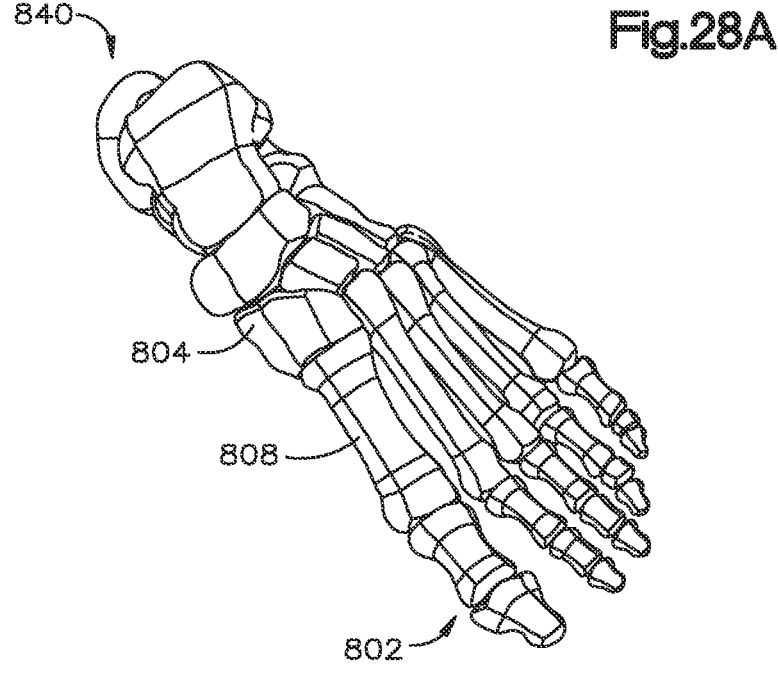
FIG. 28B shows the virtual model adjusted into a virtual corrected configuration.
Figures 28C, 28D:
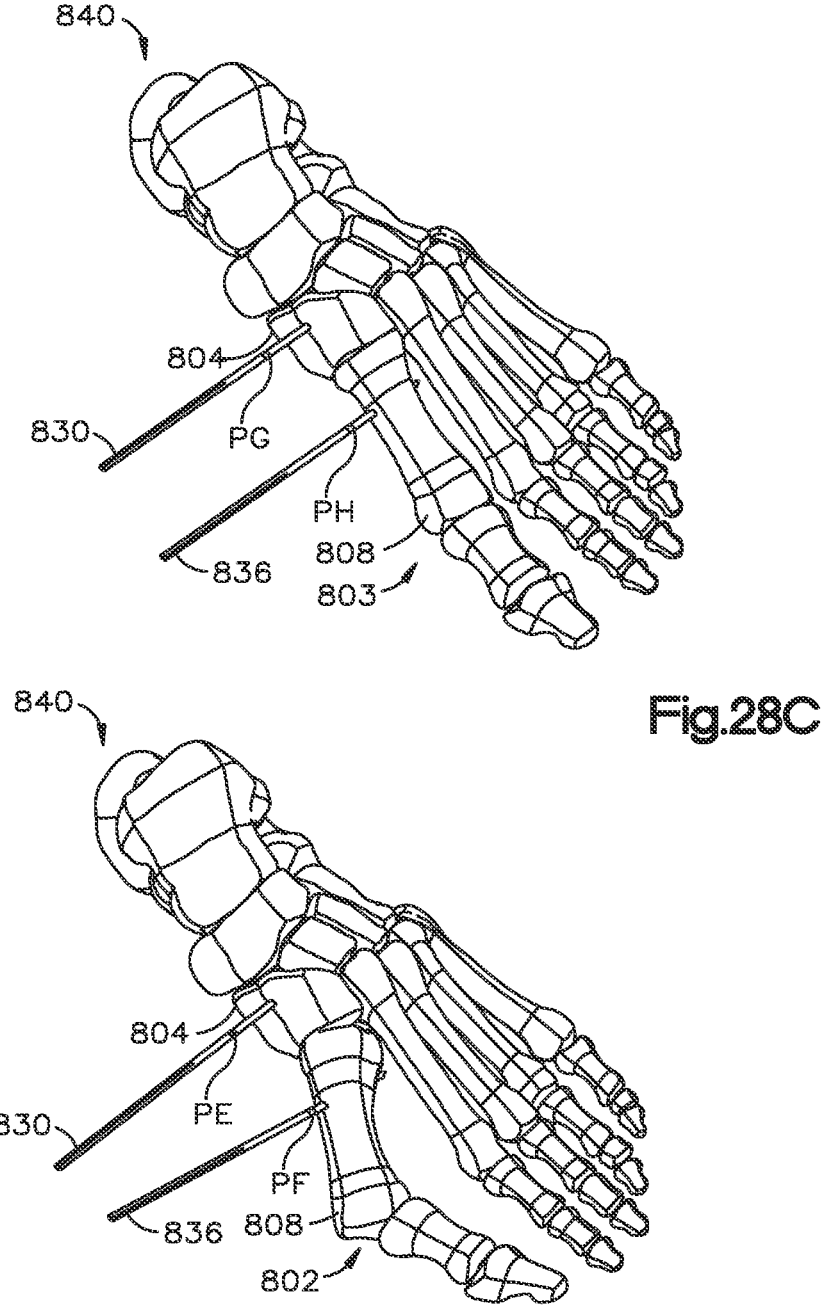
FIG. 28C shows fixing two virtual axes in a first virtual bone and a second virtual bone, respectively, in the virtual corrected configuration.
FIG. 28D shows the virtual model returned to the virtual deformed configuration with the resultant orientation of the two virtual axes defining a correction factor for the virtual model.

As shown in FIG. 22, the system for correcting alignment in the patient's foot 100 can include a bone plate assembly 700. The bone plate assembly 700 attach the medial cuneiform bone 104 and the metatarsal 108, as shown in FIGS. 25-26. The bone plate assembly 700 can include a bone plate 710. The bone plate 710 can include a first end 704 and a second end 708. The bone plate assembly 700 can include a bone clip 720. The bone clip 720 can couple between the medial cuneiform bone 104 and the metatarsal bone 108. The bone clip 720 can include a first prong 724 and second prong 728 connected by a transverse member 726. The bone plate assembly 700 can include a plurality of fasteners 730 such as bone screws, pins or other fasteners known in the field of orthopedics.

Figure 23:
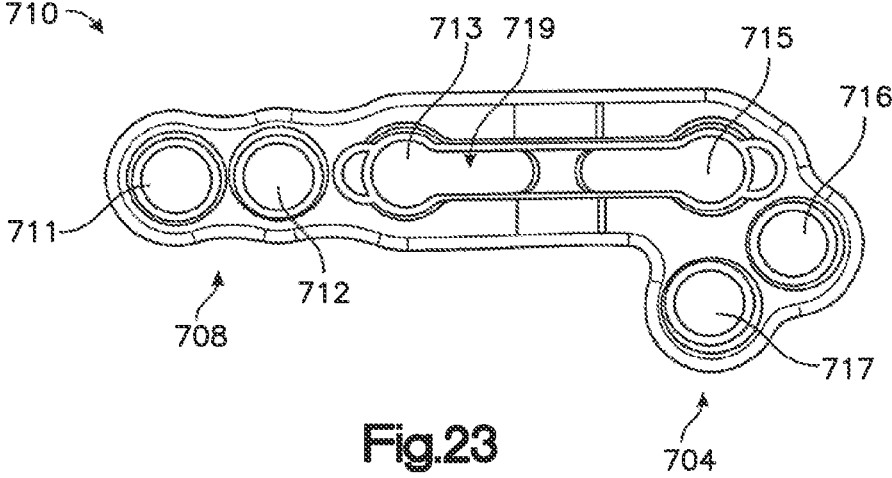
FIG. 23 shows a top view of a bone plate.
Figure 24:
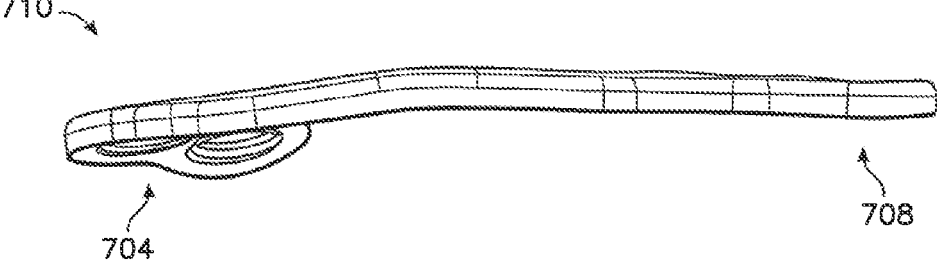
FIG. 24 shows a side view of the bone plate.

FIGS. 23-24 show further detail of the bone plate 710. The bone plate 710 can be contoured to fit against the medial cuneiform bone 104 and the metatarsal bone 108. The bone plate 710 can be made out of titanium, aluminum, steel, other suitable materials in the orthopedic field.

The first end 704 of the bone plate 710 can have a plurality of apertures 715, 716, 717. The apertures 716, 717 can be sized to receiver the fasteners 730. The aperture 715 can be sized to receive the prong 724 of the clip 720. The second end 708 of the bone plate 710 can have a plurality of apertures 711, 712, 713. The apertures 711, 712 can be sized to receive the fasteners 730. The aperture 713 can be sized to receive the prong 728 of the clip 720. The clip 720 can include a recess 719 for receiving, or at least partially receiving, the transverse member 726 of the clip 720. This can reduce the overall profile of the assembled bone plate assembly 700.

FIGS. 25-26 show the bone plate assembly 710 assembled with the patient's foot 100. The first end 704 of the bone plate 710 can be attached with the medial cuneiform bone 104 by the fasteners 730. The fasteners 730 can extend through the apertures 716, 717 and into the medial cuneiform bone 104. The second end 708 of the bone plate 710 can be attached with the metatarsal bone 108. The fasteners 730 can extend through the apertures 711, 712 and into the metatarsal bone 108. In some implementations, the fasteners 730 can be received within respective intersection points 254, 258, 262, and/or 266 of the k-wires 250. Alternatively, the fasteners can form new holes in the bones of the patient's foot.

The clip 720 can span across the joint between the medial cuneiform bone 104 and the metatarsal bone 108. The first prong 724 can be received within aperture 715 and into the metatarsal bone 108. The second prong 728 can be received through the aperture 713 and into the medial cuneiform bone 104. In certain implementations, the prongs 724, 728 can be received within the respective intersections 258, 262. The prongs 724, 728 can include a plurality of serrated edges for enhanced engagement features for attaching within the bones in the patient's foot 100.

In certain implementations, different alignment guides 200 can be used depending on the intended fixation means for the medial cuneiform bone 104 with the metatarsal bone 108. The different alignment guides 200 can include cannula that align the k-wires 250 at different points in the bone to match apertures in the different fixation means.

Virtual Modelling of Correction Factor

FIG. 27 describes a process 800 for designing an alignment guide that customized to a patient's unique anatomy. Although described herein in the context of a patient's foot, the process 800 can be used for other parts of a patient's body. The process 800 is further illustrated in FIGS. 28A-28D. At step 812, a virtual model 840 of a patient's foot is created. The virtual model 840 can be based on a scan of a patient's foot including a deformity, such as a bunion and/or Hallux valgus. The scan used to create or render the virtual model 840 can be based on a CT, PET, X-ray, ultrasound, MRI, or other type of medical imaging scan.

The virtual model 840 can include virtual representations of the bones of the patient's foot. The virtual model 840 can include a virtual deformed configuration 802 of the patient's bones. The virtual model 840 can include a virtual first bone 804 and a virtual second bone 808. The virtual first bone 804 can correspond to a medial cuneiform bone in the patient's foot and the virtual second bone 808 can correspond to a metatarsal.

The virtual model 840 can be displayed to a user through a graphical user interface (e.g., on a computer). The virtual model 840 can be manipulable by a user. In some implementations, the virtual model 840 can approximate the natural connections (e.g., ligaments, cartilage, and/or muscles) between bones in the patient's foot. Accordingly, movements of one virtual bone can alter the location of connected virtual bones. In other implementations, the virtual bones of the model 840 can be freely moved and manipulated by a user. Accordingly, feasible re-positioning of the bones and resultant movements of connected virtual bones can be approximated based on the skill and knowledge of a user.

At step 814, a user adjusts the configuration of first and second virtual bones 804, 808 into a virtual corrected configuration 803. The virtual corrected configuration 803 can include correction of one or more deformities of the patient's foot. Adjustment into the virtual corrected configuration 803 can include changing relative angles and positions between the first and second virtual bones 804, 808. Moreover, the virtual corrected configuration 803 can include one or more overlapping portions of the first and second virtual bones 804, 808. One or more virtual resection planes 804a, 808a, can be identified by a user to remove overlapping portions of the first and second virtual bones 804, 808 or otherwise adjust the lengths and dimensions thereof.

At step 816, a first virtual axis 830 is added to intersect the first virtual bone 804. A second virtual axis 836 is added to intersect the second virtual bone 808. The first virtual axis 830 is fixed relative to the first virtual bone 804. The second virtual axis 836 is fixed relative to the second virtual bone 808. The first and second virtual axes 830, 836 can be aligned with the virtual model 840 at a location that is easily accessible during surgery of the patient's foot.

The first and second virtual axes 830, 836 are parallel with each other. Advantageously, the first and second virtual axes 830, 836 can be aligned with one or more of the virtual resection planes 804a, 808a. The first virtual axis 830 extends through a point PG located in a virtual Cartesian coordinate system. The second virtual axis 836 extends through a point PH located in the virtual Cartesian coordinate system.

At step 818, the first and second virtual bones 804, 808 are returned to the original deformed configuration 802 of the model 840. The first and second virtual axes 830, 836 are rotated to different angles and/or translated relative to each other into the deformed configuration 802 from the corrected configuration 803. In the deformed configuration 802, the first and second virtual axes 830, 836 can be defined as vectors passing through respective point PE and PF, respectively, within the virtual Cartesian coordinate system.

At step 820, the relative positions of the first and second virtual axes 830, 836 in the deformed configuration 802 can be used to define a correction factor for an alignment guide. The relative positions can include relative angles in two or more of the virtual Cartesian coordinate system planes (e.g., z-x, z-y, x-y). The relative angles can correspond to the α, β, and/or γ angles in the alignment guide (e.g., alignment guide 200 or the like). The relative positions of the first and second virtual axes 830 and 836 can be based on the respective points PE and PF. The points PE and PF can correspond to the respective points PA and PB of the alignment guide (e.g., alignment guide 200 or the like). Thus, the dimensions of the virtual model 840 can be used to form the correction factor of an alignment guide for use in surgery on the patient's foot.

Furthermore, the relative positions of the first and second virtual axes 830, 836 in the corrected configuration 803 can be used to define dimensions of a correction guide. The points PG and PH can correspond to the respective points PC and PD of the correction guide (e.g., correction guide 500 or the like). The first and second virtual axes 830, 836 in the corrected configuration 803 can correspond to the parallel axes of the cannula in the correction guide.

Furthermore, the relative positions of the first and second virtual axes 830, 836 in the deformed configuration 802 can be used to define dimensions of a resection guide. The dimensions can include an orientation of a slot (e.g., slot 407) in the resection guide. The slot can be aligned parallel with one or more of the resection planes 804a, 808a. The resection guide can also include one or more apertures aligned with the first and/or second virtual axes 830, 836 in the deformed configuration 802.

As an alternative to creating the model 803, a user (e.g., a surgeon) could describe the angles (α, β, and/or γ) and/or translations needed to correct the deformities in the patient's foot 100. This description can be based on a user's knowledge and experience and/or in conjunction with viewing a scan of the patient's foot 100. The user-provided information can indicate the alignment guide 200 needed during in surgery. For example, a user can be provided a kit with multiple alignment guides and select among a predetermined set of alignment guides 200 that each correct different, but commonly seen deformations in a patient's foot. In certain implementations, the alignment guide 200 can include multiple sets of cannula that correspond to different correction factors.

Manufacturing of Lapidus System

Figure 29:
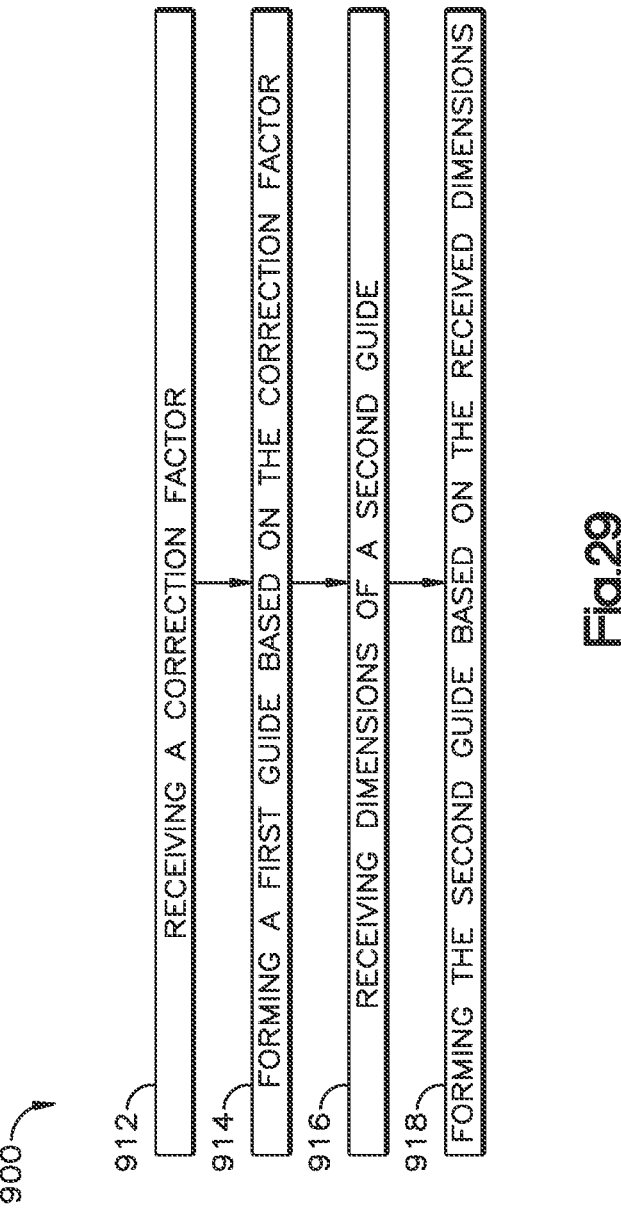
FIG. 29 shows a method of manufacturing an alignment guide based on the correction factor.

Referring to FIG. 29, process 900 is a method of manufacturing a system for correcting alignment in the patient's foot 100 based on a correction factor. At step 912, a manufacturer can receive a correction factor. The correction factor can define one or more dimensions of an alignment guide (e.g., alignment guide 200). The correction factor can be a CAD model, in some implementations. The dimensions can include orientation and positioning of one or more cannula therethrough. For example, the correction factor can be based on the process 800 described above and/or user-provided information. The correction factor can be customized to an individual patient's foot. Alternatively, the correction factor can be one of a standard set of commonly used correction factors.

At step 914, the manufacturer can form the alignment guide based on the correction factor. For example, the manufacture can 3D print the alignment guide.

At step 916, the manufacturer can receive dimensions for creating a correction guide. The dimensions for the correction guide can be based on the process 800 described above or otherwise customized to an individual patient's foot.

At step 918, the manufacturer can form the correction guide based on the received dimensions. For example, the manufacture can 3D print the correction guide.

It is further appreciated that in some instances the final configuration 103 (see FIG. 19A) of the metatarsal 108 and/or the proximal phalanx 112 with respect to the cuneiform bone 104 as produced by the correction guide 500 may be undesirable or otherwise sub-optimal as determined during the surgical procedure. Accordingly, once the bones in the patient's foot 100 have been repositioned to the corrected configuration 103, it may be desirable to further positionally adjust the metatarsal 108 with respect to the cuneiform bone 104 to an adjusted configuration 105 (see FIGS. 31B and 32B).

Alternative Component Structures

Figure 30A:
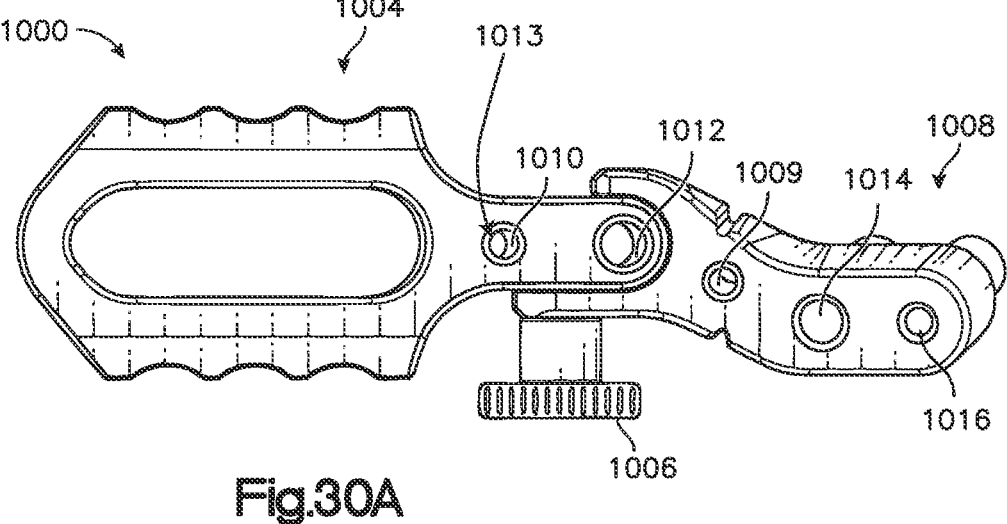
FIG. 30A shows a side view of another implementation of an alignment guide.
Figure 30B:
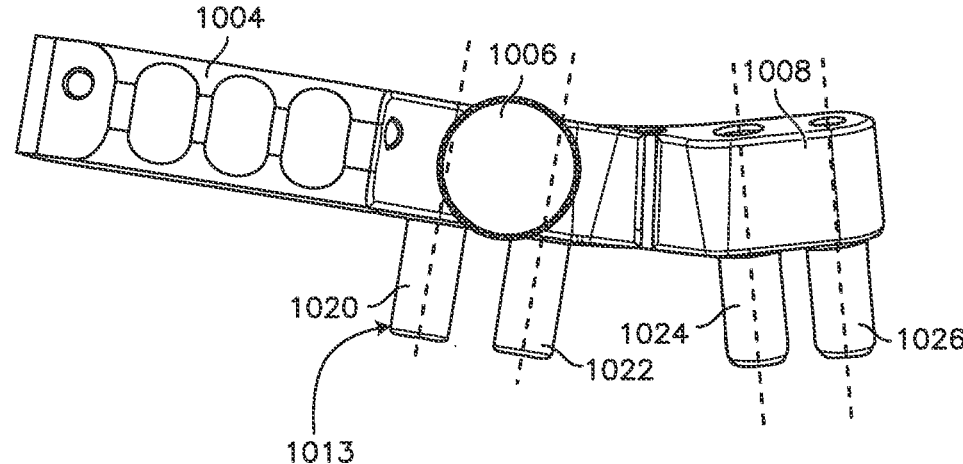
FIG. 30B shows a top view of the alignment guide of FIG. 30A.

FIGS. 30A-30B illustrate another possible configuration for an alignment guide 1000. The alignment guide 1000 can include the same features and functionalities of the alignment guide 200 described above, including some of the differences noted below. The alignment guide 1000 can include a first portion 1004 and a second portion 1008. The first portion 1004 can be releasably connectable with the second portion 1008. The first portion 1004 can include a handle 1004a. The handle portion 1004a can include an aperture therethrough. The handle portion 1004a can function to enable a user to easily hold the alignment guide 1000 in place during use. The first portion 1004 of the alignment guide 1000 can include at least one proximal cannula 1013, such as first and second cannulas 1010 and 1012 extending therethrough. The cannulas 1010 and 1012 can extend through the first portion 1004. The cannulas 1010 and 1012 can extend along respective central axes 1020 and 1022. The central axes 1020 and 1022 can be parallel to each other. The cannulas 1010 and 1012 can be referred to as first and second proximal cannulas.

The second portion 1008 can include at least one distal cannula 1015, such as third and fourth cannulas 1014 and 1016. The cannulas 1014 and 1016 can extend through the second portion 1008. The cannulas 1014 and 1016 can extend along central axes 1024 and 1026, respectively. The central axes 1014 and 1016 can be parallel with each other. The axes 1020 and 1022 can be nonparallel with the axes 1024 and 1026. The cannulas 1014 and 1016 can be referred to as first and second distal cannulas, respectively, that are disposed distal of the proximal cannula 1013.

The alignment guide 1000 can include a centering cannula 1009 that can receive a k-wire that extends into the TMT joint between the medial cuneiform bone 104 and the metatarsal 108, thereby aligning a predetermined location of the alignment guide 1000 with the tarsometatarsal joint. Accordingly, the at least one proximal cannula 1013 can be aligned with the medial cuneiform bone 104, and the at least one distal cannula 1015 can be aligned with the metatarsal 108. The centering cannula 1009 can be disposed between the at least one proximal cannula 1013 and the at least one distal cannula 1015. The centering cannula 1009 can be disposed in an intermediate portion that extends between the first and second portions 1004 and 1008, or can be disposed in either of the first and second portion 1004 and 1008.

Figure 31:
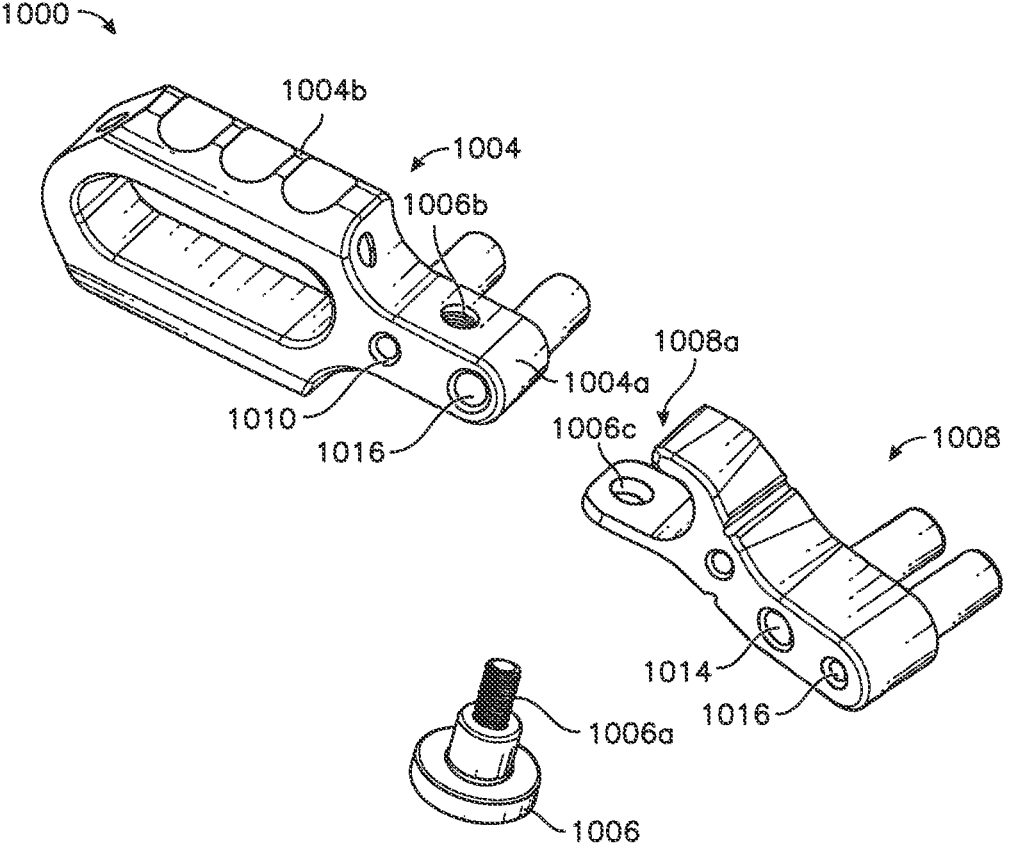
FIG. 31 shows an exploded view of the alignment guide of FIG. 30A.

As shown in FIG. 31, the first portion 1004 can be connectable with the second portion 1008 by an attachment mechanism 1006. The attachment mechanism 1006 can be a thumbscrew. As a thumbscrew, the attachment mechanism 1006 can include a threaded end 1006a. The attachment mechanism 1006 can extend through an aperture 1006b in the first portion 1004. The attachment mechanism 1006 can extend through an aperture 1006c in the second portion 1008. At least one of the apertures 1006b, 1006c can be internally threaded to couple with the threaded end 1006a. Accordingly, the first and second portions 1004, 1008 can be coupled together by the attachment mechanism 1006.

The second portion 1008 can include a recess 1008a. The first portion 1004 can include a projection portion 1004b. The projection portion 1004b can be received within the recessed portion 1008a. The recess/protrusion arrangement can enhance the stability of the coupling between the first portion 1004 and the second portion 1008.

Figure 32A:
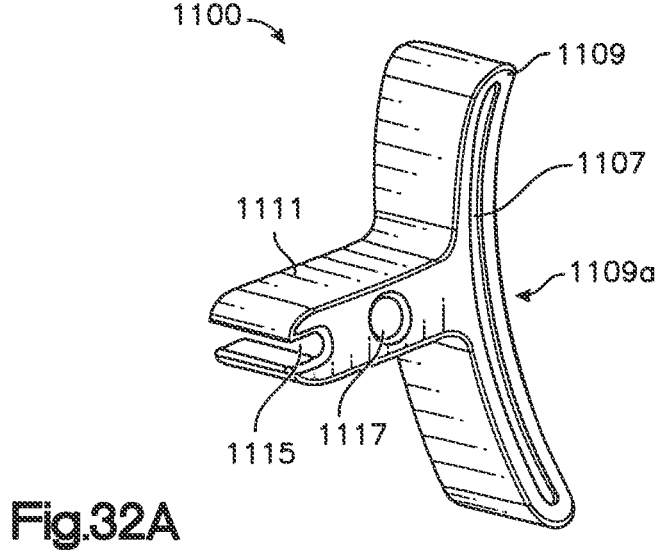
FIG. 32A shows a perspective view of another implementation of a resection guide.
Figure 32B:
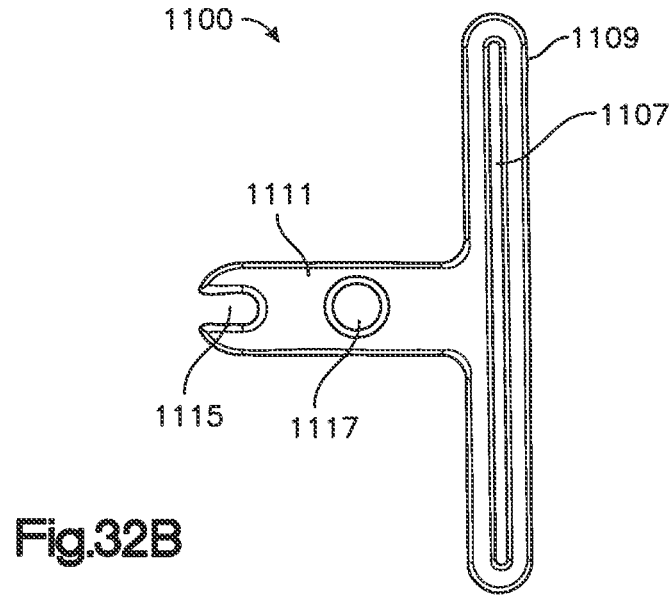
FIG. 32B shows a front view of the resection guide of FIG. 32A.

FIGS. 32A-32B show another implementation of a resection guide 1100. The resection guide 1100 can be structured similarly to the resection guide 404 described above, including some of the differences noted herein. The resection guide 1100 can include a first portion 1111. The first portion 1111 can include one or more apertures 1115 and 1117 extending therethrough. The first portion 1111 can be coupled with a planar portion 1109. The planar portion 1109 can include a slots 1107 therein. The slot 1107 can be sized to allow a resection tool to extend therethrough for resecting a bone of a patient's body (e.g., the patient's foot 100). In some implementations, the planar portion 1109 can include a curved shape to allow the slot 1107 to be placed closer to and/or in contact with the patient's body. This can reduce error associated with the process of resecting a bone.

Figure 33:
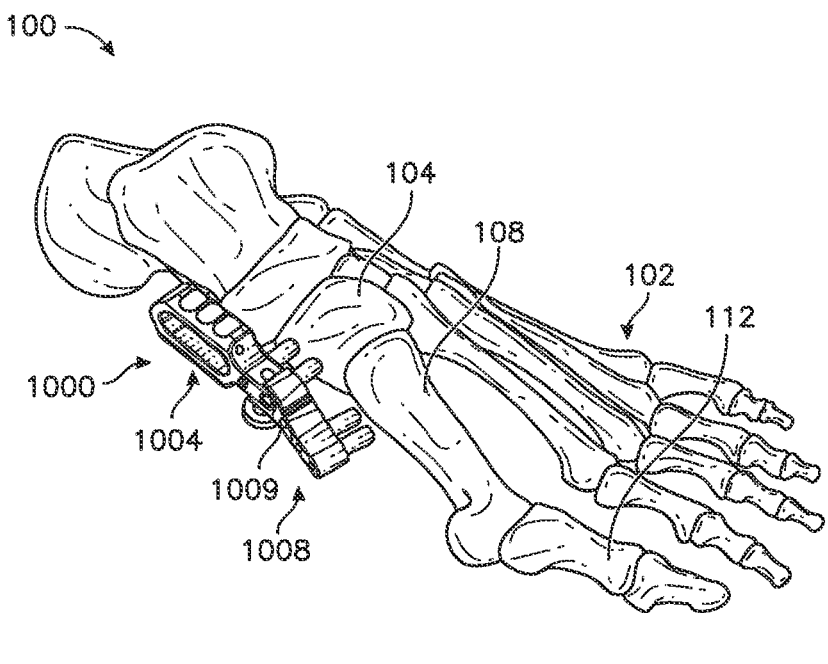
FIG. 33 shows alignment of the alignment guide of FIG. 30A with a patient's foot.
Figure 34:
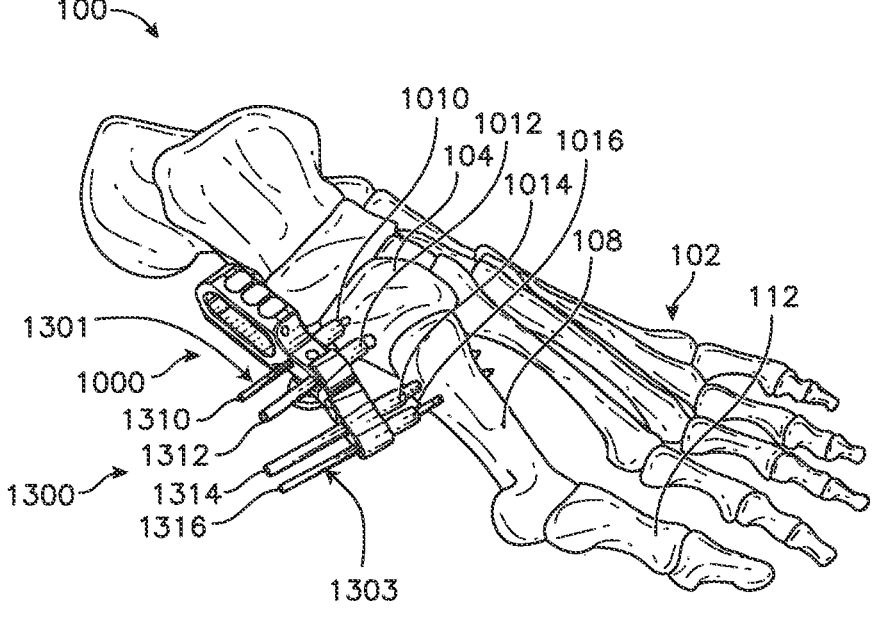
FIG. 34 shows insertion of a plurality of k-wires into a medial cuneiform bone and a metatarsal bone through the alignment guide.

FIG. 33 shows one method of using the alignment guide 1000 in a procedure for correcting alignment between two bones in a patient's body. The alignment guide 1000 can be used to correct alignment of a medial cuneiform bone 104 and a metatarsal bone 108 in a patient's foot 100. The process shown in FIGS. 33-38 is similar to and can include any of the steps and details described above in the process shown in FIGS. 1-26.

The centering cannula 1009 can align the alignment guide 1000 at the tarsometatarsal joint between the medial cuneiform bone 104 and the metatarsal 108. A k-wire (not shown) can extend through the centering cannula 1009 and into the space between the medial cuneiform bone 104 and the metatarsal 108. The first end 1004 of the alignment guide 1000 can be generally aligned with the medial cuneiform bone 104. The second end 1008 of the alignment guide 1000 can be generally aligned with the metatarsal 108. As shown further in FIG. 34, a plurality of temporary fixation element such as k-wires 1300 can be inserted through the respective cannula of the alignment guide 1000 and into the medial cuneiform bone 104 and the metatarsal bone 108. At least one proximal k-wire 1301 such as first k-wire 1310 can be inserted through the cannula 1010 and into the medial cuneiform bone 104. The at least one proximal k-wire 1301 can further include a second k-wire 1312 that can be inserted through the cannula 1012 and into the medial cuneiform bone 104. At least one distal k-wire 1303 such as a third k-wire 1314 can be inserted through the cannula 1014 and into the metatarsal 108. The at least one distal k-wire 1303 can further include a fourth k-wire 1316 that extends through the cannula 1016 into the metatarsal 108. The k-wires 1300 can extend along respective axes of the cannula of the alignment guide 1000. Accordingly, the alignment guide can define the intersection angles of the k-wires 1300.

The first and second k-wires 1310 and 1312 can be referred to as first and second proximal k-wires, and the third and fourth k-wires 1314 and 1316 can be referred to as first and second distal k-wires that are disposed distal of the proximal k-wires. The proximal k-wires are configured to be inserted into respective ones of the proximal cannulas 1013 and into the cuneiform bone 104. The distal k-wires are configured to be inserted into respective ones of the distal cannulas 1015 and into the metatarsal 108. While the system can include two proximal k-wires and two distal k-wires in one example, it should be appreciated that the system can include any number of proximal and distal k-wires including at least one. Thus, at least one proximal k-wire 1301 can be inserted through at least one proximal cannula 1013 and into the cuneiform bone 104, and at least one distal k-wire 1303 can be inserted through at least one distal cannula 1015 and into the metatarsal 108.

Figures 35, 36:
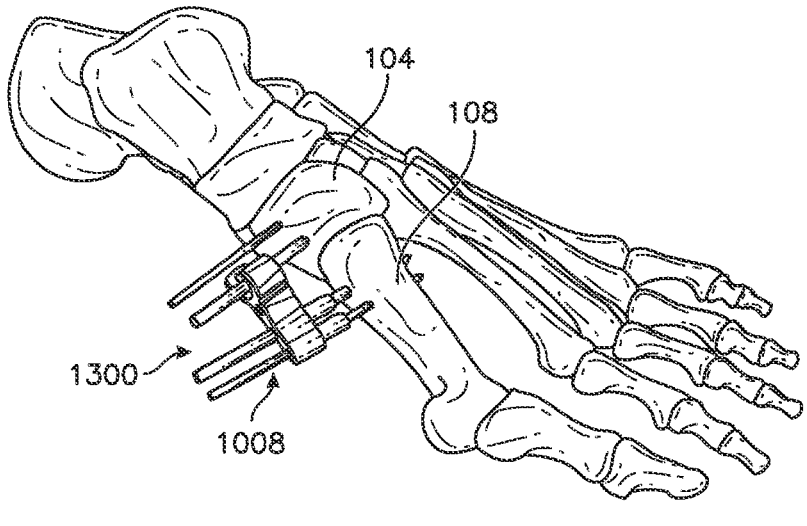
FIG. 35 shows a partial disassembly of the alignment guide.
FIG. 36 shows the alignment guide removed and the installation of the resection guide of FIG. 32A.

As shown in FIG. 35, the first portion 1004 of the alignment guide 1000 can be removed from the second portion 1008. The attachment mechanism 1006 can be removed from between the first portion 1004 and the second portion 1008. the first portion 1004 can be removed from the K wires 1300. The second portion 1008 can be removed from the k-wires 1300.

As shown in FIG. 36, the resection guide 1100 can be slid over the k-wires 1300. The planar portion 1109 can be aligned with one or both of the medial cuneiform bone 104 and/or the metatarsal 108. A resection tool 1400 can be inserted through the slot 1107 to form resection planes 104a, and/or 108a on the respective medial cuneiform bone 104 and metatarsal 108. As described above, this can facilitate alignment of the medial cuneiform bone 104 and the metatarsal 108 in a corrected configuration 103.

Figures 37, 38:
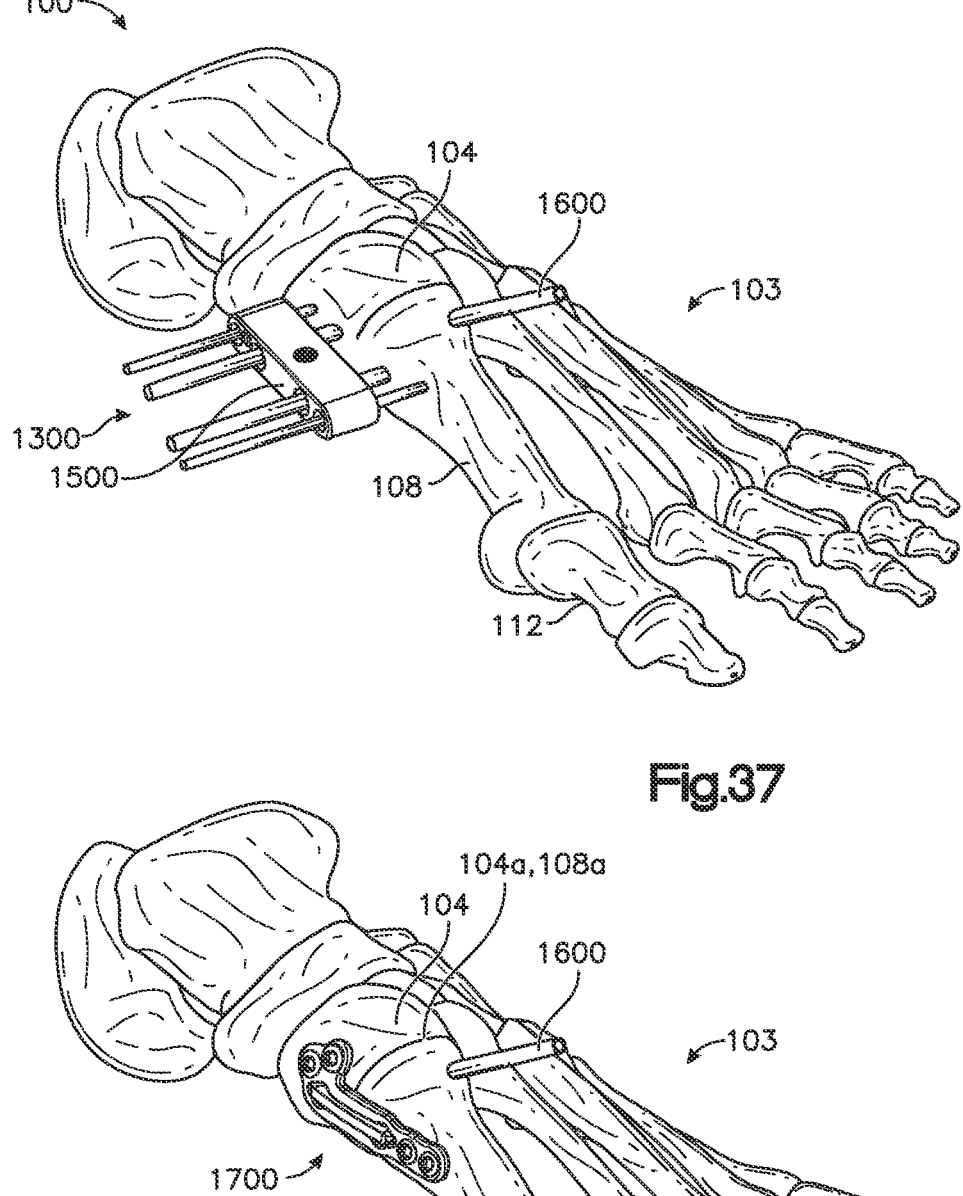
FIG. 37 shows a correction guide assembled over the plurality of k-wires to align the medial cuneiform bone and the metatarsal bone of the patient's foot into a corrected configuration and the insertion of a fixing k-wire.
FIG. 38 shows a bone plate assembly assembled with the medial cuneiform bone and metatarsal bone in the corrected configuration.

As shown in FIG. 37, a correction guide 1500 can be slid over the k-wires 1300. The correction guide 1500 can be constructed as described with respect to the correction guide 500 of FIGS. 18A-20. The correction guide 1500 can include a plurality of cannula extending along respective central axes that can be parallel with each other or can converge toward each other as described above. The k-wires 1300 can be received in the respective cannulas of the collection guide 1500. This can realign and adjust positions of the medial cuneiform bone 104, metatarsal 108 and/or the proximal phalanx 112 to define the corrected configuration 103 of the patient's foot 100.

In the corrected configuration 103, a fixing k-wire 1600 (or similar mechanism) can be inserted to fix the positions of the first metatarsal 108 and the medial cuneiform bone 104. As shown in FIG. 38, a bone plate assembly 1700, similar to the bone plate assembly 700, can be attached to the medial cuneiform bone 104 and the metatarsal 108 to maintain the relative positions of the two bones in the corrected configuration 103.

Certain Terminology

Terms of orientation used herein, such as "top," "bottom," "proximal," "distal," "longitudinal," "lateral," and "end," are used in the context of the illustrated example. However, the present disclosure should not be limited to the illustrated orientation. Indeed, other orientations are possible and are within the scope of this disclosure. Terms relating to circular shapes as used herein, such as diameter or radius, should be understood not to require perfect circular structures, but rather should be applied to any suitable structure with a cross-sectional region that can be measured from side-to-side. Terms relating to shapes generally, such as "circular," "cylindrical," "semi-circular," or "semi-cylindrical" or any related or similar terms, are not required to conform strictly to the mathematical definitions of circles or cylinders or other structures, but can encompass structures that are reasonably close approximations.

Conditional language, such as "can," "could," "might," or "may," unless specifically stated otherwise, or otherwise understood within the context as used, is generally intended to convey that certain examples include or do not include, certain features, elements, and/or steps. Thus, such conditional language is not generally intended to imply that features, elements, and/or steps are in any way required for one or more examples.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain examples require the presence of at least one of X, at least one of Y, and at least one of Z.

The terms "approximately," "about," and "substantially" as used herein represent an amount close to the stated amount that still performs a desired function or achieves a desired result. For example, in some examples, as the context may dictate, the terms "approximately," "about," and "substantially," may refer to an amount that is within less than or equal to 10% of the stated amount. The term "generally" as used herein represents a value, amount, or characteristic that predominantly includes or tends toward a particular value, amount, or characteristic. As an example, in certain examples, as the context may dictate, the term "generally parallel" can refer to something that departs from exactly parallel by less than or equal to 20 degrees. All ranges are inclusive of endpoints.

SUMMARY

Several illustrative examples of Lapidus procedure systems and methods have been disclosed. Although this disclosure has been described in terms of certain illustrative examples and uses, other examples and other uses, including examples and uses which do not provide all of the features and advantages set forth herein, are also within the scope of this disclosure. Components, elements, features, acts, or steps can be arranged or performed differently than described and components, elements, features, acts, or steps can be combined, merged, added, or left out in various examples. All possible combinations and subcombinations of elements and components described herein are intended to be included in this disclosure. No single feature or group of features is necessary or indispensable.

Certain features that are described in this disclosure in the context of separate implementations can also be implemented in combination in a single implementation. Conversely, various features that are described in the context of a single implementation also can be implemented in multiple implementations separately or in any suitable subcombination. Moreover, although features may be described above as acting in certain combinations, one or more features from a claimed combination can in some cases be excised from the combination, and the combination may be claimed as a subcombination or variation of a sub combination.

Any portion of any of the steps, processes, structures, and/or devices disclosed or illustrated in one example in this disclosure can be combined or used with (or instead of) any other portion of any of the steps, processes, structures, and/or devices disclosed or illustrated in a different example or flowchart. The examples described herein are not intended to be discrete and separate from each other. Combinations, variations, and some implementations of the disclosed features are within the scope of this disclosure.

While operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Additionally, the operations may be rearranged or reordered in some implementations. Also, the separation of various components in the implementations described above should not be understood as requiring such separation in all implementations, and it should be understood that the described components and systems can generally be integrated together in a single product or packaged into multiple products. Additionally, some implementations are within the scope of this disclosure.

Further, while illustrative examples have been described, any examples having equivalent elements, modifications, omissions, and/or combinations are also within the scope of this disclosure. Moreover, although certain aspects, advantages, and novel features are described herein, not necessarily all such advantages may be achieved in accordance with any particular example. For example, some examples within the scope of this disclosure achieve one advantage, or a group of advantages, as taught herein without necessarily achieving other advantages taught or suggested herein. Further, some examples may achieve different advantages than those taught or suggested herein.

Some examples have been described in connection with the accompanying drawings. The figures are drawn and/or shown to scale, but such scale should not be limiting, since dimensions and proportions other than what are shown are contemplated and are within the scope of the disclosed invention. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various examples can be used in all other examples set forth herein. Additionally, any methods described herein may be practiced using any device suitable for performing the recited steps.

For purposes of summarizing the disclosure, certain aspects, advantages and features of the inventions have been described herein. Not all, or any such advantages are necessarily achieved in accordance with any particular example of the inventions disclosed herein. No aspects of this disclosure are essential or indispensable. In many examples, the devices, systems, and methods may be configured differently than illustrated in the figures or description herein. For example, various functionalities provided by the illustrated modules can be combined, rearranged, added, or deleted. In some implementations, additional or different processors or modules may perform some or all of the functionalities described with reference to the examples described and illustrated in the figures. Many implementation variations are possible. Any of the features, structures, steps, or processes disclosed in this specification can be included in any example.

In summary, various examples of Lapidus procedure systems and related methods have been disclosed. This disclosure extends beyond the specifically disclosed examples to other alternative examples and/or other uses of the examples, as well as to certain modifications and equivalents thereof. Moreover, this disclosure expressly contemplates that various features and aspects of the disclosed examples can be combined with, or substituted for, one another. Accordingly, the scope of this disclosure should not be limited by the particular disclosed examples described above, but should be determined only by a fair reading of the claims.

While the above detailed description has shown, described, and pointed out novel features as applied to illustrative embodiments, it will be understood that various omissions, substitutions, and changes in the form and details of the devices or algorithms illustrated can be made without departing from the spirit of the disclosure. As will be recognized, certain embodiments described herein can be embodied within a form that does not provide all of the features and benefits set forth herein, as some features can be used or practiced separately from others. All changes which come within the meaning and range of equivalency of the claims are to be embraced within their scope.

What is claimed is:

1. A method for correcting alignment between a first bone and a second bone by fusing a joint between the first bone and the second bone, the method comprising:

inserting a joint alignment member into the joint with a shaft of the joint alignment member extending outwardly from the joint;

inserting the shaft of the joint alignment member into an alignment cannula of an alignment guide;

driving at least one first wire through at least one first cannula of a guide body of the alignment guide and into the first bone;

inserting an insert of the alignment guide into a receiving aperture of the guide body of the alignment guide;

driving at least one second wire through at least one second cannula of the insert of the alignment guide and into the second bone; and removing the alignment guide from the at least one first wire and the at least one second wire.

2. The method of claim 1, wherein the removing step comprises removing the insert from both the receiving aperture of the guide body and the at least one second wire.

3. The method of claim 2, further comprising removing the guide body from the at least one first wire after the insert is removed from the receiving aperture and the at least one second wire.

4. The method of claim 3, wherein the step of removing the guide body also removes the at least one second wire from the receiving aperture.

5. The method of claim 1, wherein the at least one first cannula comprises first and second cannulas, the at least one second cannula comprises third and fourth cannulas, the at least one first wire comprises first and second wires, and the at least one second wire comprises third and fourth wires.

6. The method of claim 5, wherein first and second central axes of the first and second cannula, respectively, are aligned with each other along a first direction, and third and fourth central axes of the third and fourth cannula, respectively, are aligned along a second direction different from the first direction.

7. The method of claim 6, wherein the first and second axes are parallel to each other, and the third and fourth axes are parallel to each other.

8. The method of claim 1, further comprising the step of resecting at least one of the first bone and the second bone at the joint.

9. The method of claim 8, further comprising the step of resecting each of the first bone and the second bone at the joint.

10. The method of claim 9, further comprising the step of inserting a resection guide over the first and second wires, and the step of resecting each of the first bone and the second bone at the joint comprises resecting the first bone with a resecting tool through a slot of the resection guide.

11. The method of claim 9, further comprising the step of inserting a resection guide over third and fourth wires, and the step of resecting each of the first bone and the second bone at the joint comprises resecting the second bone with a resection tool through a slot of the resection guide.

12. The method of claim 1, further comprising the step of inserting a correction guide over the at least one first wire and the at least one second wire so as to align the first and second bones in a corrected configuration.

13. The method of claim 12, further comprising the step of fixing the first bone with the second bone in the corrected configuration.

14. The method of claim 1, wherein the first bone is a cuneiform and the second bone is a metatarsal.

15. The method of claim 1, wherein step of inserting the joint alignment member comprises causing the shaft to project substantially along a superior direction.

16. The method of claim 1, wherein the step of inserting the shaft comprises inserting the shaft through the alignment cannula.

* * * * *